US010569000B2

(12) United States Patent
De los Reyes, V et al.

(10) Patent No.: US 10,569,000 B2
(45) Date of Patent: Feb. 25, 2020

(54) SYSTEM FOR ANALYZING VASCULAR REFILL DURING SHORT-PULSE ULTRAFILTRATION IN HEMODIALYSIS

(71) Applicant: Fresenius Medical Care Holdings, Inc., Waltham, MA (US)

(72) Inventors: Aurelio A. De los Reyes, V, Rizal (PH); Doris H. Fuertinger, Long Island City, NY (US); Franz Kappel, Graz (AT); Anna Meyring-Wosten, New York, NY (US); Stephan Thijssen, New York, NY (US); Peter Kotanko, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 532 days.

(21) Appl. No.: 15/309,727

(22) PCT Filed: May 29, 2015

(86) PCT No.: PCT/US2015/033225
§ 371 (c)(1),
(2) Date: Nov. 8, 2016

(87) PCT Pub. No.: WO2015/184287
PCT Pub. Date: Dec. 3, 2015

(65) Prior Publication Data
US 2017/0239409 A1    Aug. 24, 2017

Related U.S. Application Data

(60) Provisional application No. 62/005,744, filed on May 30, 2014.

(51) Int. Cl.
*A61M 1/16*      (2006.01)
*G16H 50/50*    (2018.01)
*G06F 17/13*    (2006.01)

(52) U.S. Cl.
CPC ........... *A61M 1/1613* (2014.02); *G06F 17/13* (2013.01); *G16H 50/50* (2018.01);
(Continued)

(58) Field of Classification Search
CPC . A61B 5/02028; A61B 5/026; A61B 5/14535; A61B 5/4875; A61B 2205/18;
(Continued)

(56) References Cited

U.S. PATENT DOCUMENTS

| | | | |
|---|---|---|---|
| 2006/0183988 A1* | 8/2006 | Baker, Jr. ................ | A61M 1/16 210/646 |
| 2007/0215545 A1* | 9/2007 | Bissler ............... | A61B 5/02416 600/336 |
| 2012/0150102 A1 | 6/2012 | Childers et al. | |

FOREIGN PATENT DOCUMENTS

| | | |
|---|---|---|
| CN | 203354985 U | 12/2013 |
| WO | WO 2012-054880 A2 | 4/2012 |

OTHER PUBLICATIONS

De Los Reyes et al., *J. Theoretical Biol.*, 390, 146-155 (2016).
(Continued)

*Primary Examiner* — Benjamin J Klein
(74) *Attorney, Agent, or Firm* — Leydig, Voit & Mayer, Ltd.

(57) ABSTRACT

A method includes: receiving measurements of a blood-related parameter corresponding to a patient undergoing hemodialysis; estimating a value of one or more hemodialysis treatment-related parameters by applying a vascular refill model based on the received measurements of the blood-related parameter, wherein the one or more hemodialysis treatment-related parameters are indicative of an effect of vascular refill on the patient caused by the hemodialysis; determining, based on the one or more estimated values of the one or more hemodialysis treatment-related parameters, a hemodialysis treatment-related operation; and
(Continued)

facilitating performance of the treatment-related operation. The vascular refill model is a two-compartment model based on a first compartment corresponding to blood plasma in the patient's body, a second compartment based on interstitial fluid in the patient's body, and a semi-permeable membrane separating the first compartment and the second compartment.

19 Claims, 13 Drawing Sheets

(52) U.S. Cl.
CPC . *A61M 2205/18* (2013.01); *A61M 2205/3334* (2013.01); *A61M 2205/3344* (2013.01); *A61M 2205/3379* (2013.01); *A61M 2205/3553* (2013.01); *A61M 2205/3584* (2013.01); *A61M 2205/50* (2013.01); *A61M 2205/502* (2013.01); *A61M 2230/005* (2013.01); *A61M 2230/20* (2013.01); *A61M 2230/207* (2013.01); *A61M 2230/30* (2013.01)

(58) Field of Classification Search
CPC .... A61B 2205/3306; A61B 2205/3334; A61B 2205/3344; A61B 2205/3379; A61B 2205/3553; A61B 2205/3584; A61B 2205/50; A61B 2205/502; A61B 2230/005; A61B 2230/20; A61B 2230/207; A61B 2230/30; A61M 1/1613; A61M 1/3609
See application file for complete search history.

(56) References Cited

OTHER PUBLICATIONS

Schneditz et al., *Kidney Int.*, 42, 1425-1433 (1992).
European Patent Application No. 15799738.8, Search Report (dated Jan. 11, 2018).
Banks et al., "Parameter Selection Methods in Inverse Problem Formation," in *Mathematical Modeling and Validation in Physiology, Lecture Notes in Mathematics*, Springer-Verlag, 43-73 (2013).
Banks et al., *J. Inv. Ill-Posed Problems*, 18, 25-83 (2010).
Batzel et al, "Merging Mathematical and Physiological Knowledge: Dimensions and Challenges," in in *Mathematical Modeling and Validation in Physiology, Lecture Notes in Mathematics*, Springer-Verlag, 3-19 (2013).
Bauer, *Clin. Nephrol.*, 16(3), 114-118 (1981).
Brennan et al., *Kidney Int.*, 17(3), 364-371 (1980).
Brenner et al., *Kidney Int.*, 2(1), 51-53 (1972).
Charney et al., *J. Med. Eng. Technol.*, 23(2). 45-52 (1999).
Cintrón-Arias et al., J. Inv. Ill-Posed Problems, 17 545-564 (2009).
Dvorak, Curr. Opin. Hematol., 17(3), 225-229 (2010).
Ebah et al., *Kidney Int.*, 84(5) 980-988 (2013).
Fauchald, *Kidney Int.*, 29(4), 895-900 (1986).
Gore et al., *Fed. Proc.*, 34(11), 2031-2037 (1975).
Guyton, *Circ. Res.*, 16, 452-460 (1965).
Harper et al., *Kidney Int.*, 61(4), 1416-1422 (2002).
Heldt et al., "Mathematical Modeling of Physiological Systems," in *Mathematical Modeling and Validation in Physiology, Lecture Notes in Mathematics*, Springer-Verlag, 21-41 (2013).
Iimura et al., *Nephron*, 74(1), 19-25 (1996).
Järhult et al., *Acta Physiol. Scand.*, 91(1), 32-41 (1974).
Johnson et al., *J. Applied Physiology*, 17, 503-508 (1962).
Koomans et al., *Kidney Int.*, 26(6), 848-854 (1984).
Landis et al., "Exchange of Substances Through the Capillary Walls," in *Handbook of Physiology*, American Physiological Society, Washington DC, 961-1034 (1963).
Levick , *Exp. Physiology*, 76(6), 825-857 (1991).
Levick et al., *Cardiovascular Research*, 87(2), 198-210 (2010).
Michel et al., *Physiological Reviews*, 79(3), 703-761 (1999).
Navar et al., Am. J. Physiology-Heart and Circulatory Physiology, 233(2), H295-H298 (1977).
Nitta et al., *Tohoku J. Exp. Med.*, 135(1), 43-49 (1981).
Ookawara et al., *Therapeutic Apheresis and Dialysis*, 18(2), 202-207 (2014).
Renkin, *Am. J. Physiology*, 250(5), H706-H710 (1986).
Rodriguez et al., *Kidney Int.*, 68(2), 854-861 (Aug. 2005).
Starling E.H., *J Physiol.*, 19(4), 312-326 (1896).
Staverman, "The Theory of Measurement of Osmotic Pressure," Recueil des Travaux himiques des Pays-Bas, 70(4), 344-352 (1951).
Tabei et al., *Nephron*, 74(2), 266-274 (1996).
Taylor et al., "Exchange of Macromolecules Across the Microcirculation," in *Handbook of Physiology*, vol. 4, 467-520, American Physiological Society, Bethesda, MD (1984).
Thijssen et al., *Blood Purif*, 33, 165-170 (2012).
Thomaseth et al., *Ann Biomed Eng.*, 27(5), 607-616 (1999).
Titze, *Kidney Int.*, 84(5) 869-871 (Nov. 2013).
Williams et al., *Clin Sci (Lond)*, 79 (1), 5-8 (1990).
Yashiro et al., *Blood Purif*, 23(6), 431-439 (2005).
Zellweger et al, *ASAIO J.*, 50(3), 242-245 (2004).
Chinese Patent Application No. 201580028906.7, Office Action (dated Feb. 1, 2019).

* cited by examiner

SYSTEM FOR ANALYZING VASCULAR REFILL DURING SHORT-PULSE ULTRAFILTRATION IN HEMODIALYSIS

CROSS-REFERENCE TO RELATED APPLICATIONS

This patent application is a national phase of International Patent Application No. PCT/US2015/033225, filed May 29, 2015, which claims the benefit of U.S. Provisional Patent Application No. 62/005,744, filed May 30, 2014, both of which are incorporated herein by reference in their entireties.

BACKGROUND

End-stage renal disease (ESRD) patients typically have an increased extracellular volume (ECV) due to their impaired kidney function. Management of this fluid excess is one of the cornerstones in the treatment of these patients. In patients who undergo hemodialysis (HD), this excess extracellular fluid volume can be removed by ultrafiltration (UF). During UF, fluid is removed from the blood stream (intravascular compartment), and fluid from the tissue (interstitial compartment) shifts into the intravascular space (driven by hydrostatic and oncotic pressure gradients; details below) to counter the reduction in blood plasma volume. This process, called vascular refilling, is critical for maintenance of adequate intravascular filling and blood pressure during dialysis.

Whenever the vascular refill rate is less than the ultrafiltration rate, the plasma volume declines; this process manifests itself in a decline in absolute blood volume (ABV) and a decline in relative blood volume (RBV). This decline of RBV translates into increased hematocrit and blood protein levels. Measurements of hematocrit or blood protein concentration during HD form the basis of relative blood volume monitoring. RBV can be measured continuously and non-invasively throughout HD with commercially available devices, such as the Crit-Line Monitor (CLM) or the Blood Volume Monitor (BVM). While the CLM measures hematocrit, the BVM measures blood protein concentration.

The RBV dynamic is the result of plasma volume reduction by ultrafiltration, and vascular refilling by capillary and lymphatic flow.

SUMMARY

Embodiments of the invention provide a system for analyzing refill processes in patients. Understanding these quantitative aspects is clinically important, since both the driving forces (e.g. hydrostatic pressures; details below) and the capillary tissue characteristics (e.g. hydraulic conductivity; details below), are intimately related to (patho) physiological aspects which are highly relevant in the care of HD patients, such as fluid overload and inflammation. Neither of these forces and tissue characteristics are accessible to direct measurements feasible during routine HD treatments.

The system utilizes mathematical models on qualitative and quantitative behavior of vascular refill during dialysis to estimate certain output parameters corresponding to the quantities that are indicative of the fluid dynamics within a patient. Based on these output parameters, the system is able to perform various treatment-related operations, such as indicating status of the parameters to a treating physician, providing notifications and alerts, adjusting current and/or future treatment processes, aggregating and storing patient-specific information to provide trend data and/or to modify future treatments based thereon, etc.

In a particular exemplary embodiment, the system utilizes a two-compartment model incorporating microvascular fluid shifts and lymph flow from the interstitial to the vascular compartment. Protein flux is described by a combination of both convection and diffusion.

In an exemplary embodiment, a Crit-Line device is used to identify and monitor certain input parameters of a patient, including for example, a Hematocrit ("Hct") level.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
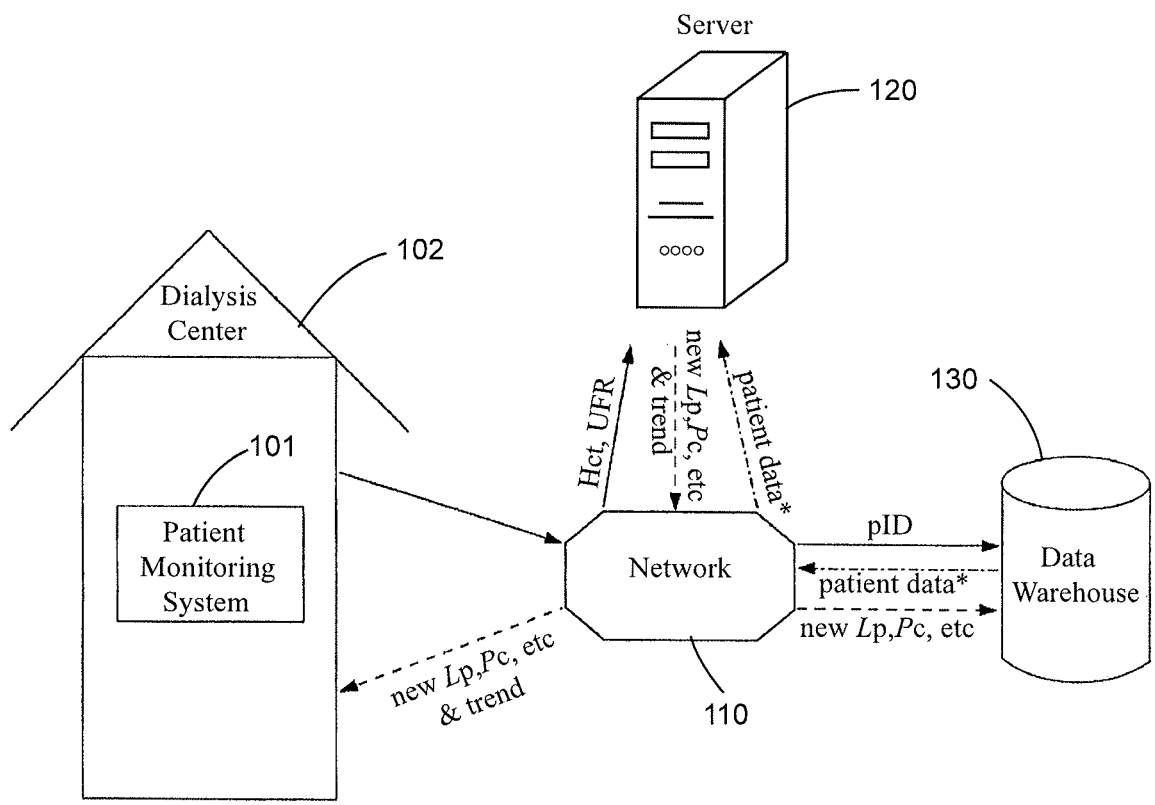
FIG. 1 is a block diagram illustrating an exemplary network environment usable in connection with certain exemplary embodiments of the invention.

FIG. 1 is a block diagram illustrating an exemplary network environment usable in connection with certain exemplary embodiments of the invention. The system includes a patient monitoring system 101 (for example, a combination of a sensing device connected to a host computer having a display for indicating patient-related or treatment-related information and having a network communication interface, or a integrated sensing device with communication capabilities), typically located at a dialysis treatment center 102, that is configured to transmit hematocrit (Hct) (or alternatively RBV), ultrafiltration rate (UFR), and patient identification (pID) information over a network 110. Examples of patient monitoring systems usable with embodiments of the invention include, but are not limited to, a Crit-Line monitoring device, a CliC monitoring device, and other devices suitable for measuring Hct and/or RBV. A server 120 receives, via the network 110 (e.g., the internet or a local or private network), the Hct (or alternatively RBV) and UFR values. The server may also utilize patient-specific data retrieved from a data warehouse 130 (e.g., a database in communication with the server 120) based on the pID. The patient-specific data may include, for example, ABV, bioimpedance measurements, height, weight, gender, IDWG, as well as previous estimated values for $L_p$, $P_c$, $P_i$, $\sigma$, $\alpha$, $\kappa$ (as discussed below) determined for the patient.

The server 120 uses the received information to calculate further information based upon models for vascular refill during dialysis (e.g., estimated values for $L_p$, $P_c$, $P_i$, $\sigma$, $\alpha$, $\kappa$ and trend data). This information may then be provided to the data warehouse 130 for storage and for future reference, and to the dialysis center 102 for indication to a treating physician or for performance of other treatment-related operations (e.g., providing notifications and alerts, and adjusting current and/or future treatment processes).

Although FIG. 1 depicts a network environment having a server 120 and data warehouse 130 remotely situated from the dialysis center 102, it will be appreciated that various other configurations of the environment may be used as well. For example, the computing device performing the model-based estimations may include a local memory capable of storing patient-specific data, and the computing device may be situated locally within the dialysis center and/or formed integrally with the patient monitoring system (e.g., as part of a host computer or integrated sensing device). In another example, the patient-specific data may be stored on a data card or other portable memory device that is configured to interface with a treatment device, to allow the treatment device to provide patient-specific treatment and display patient-specific information.

Figure 2:
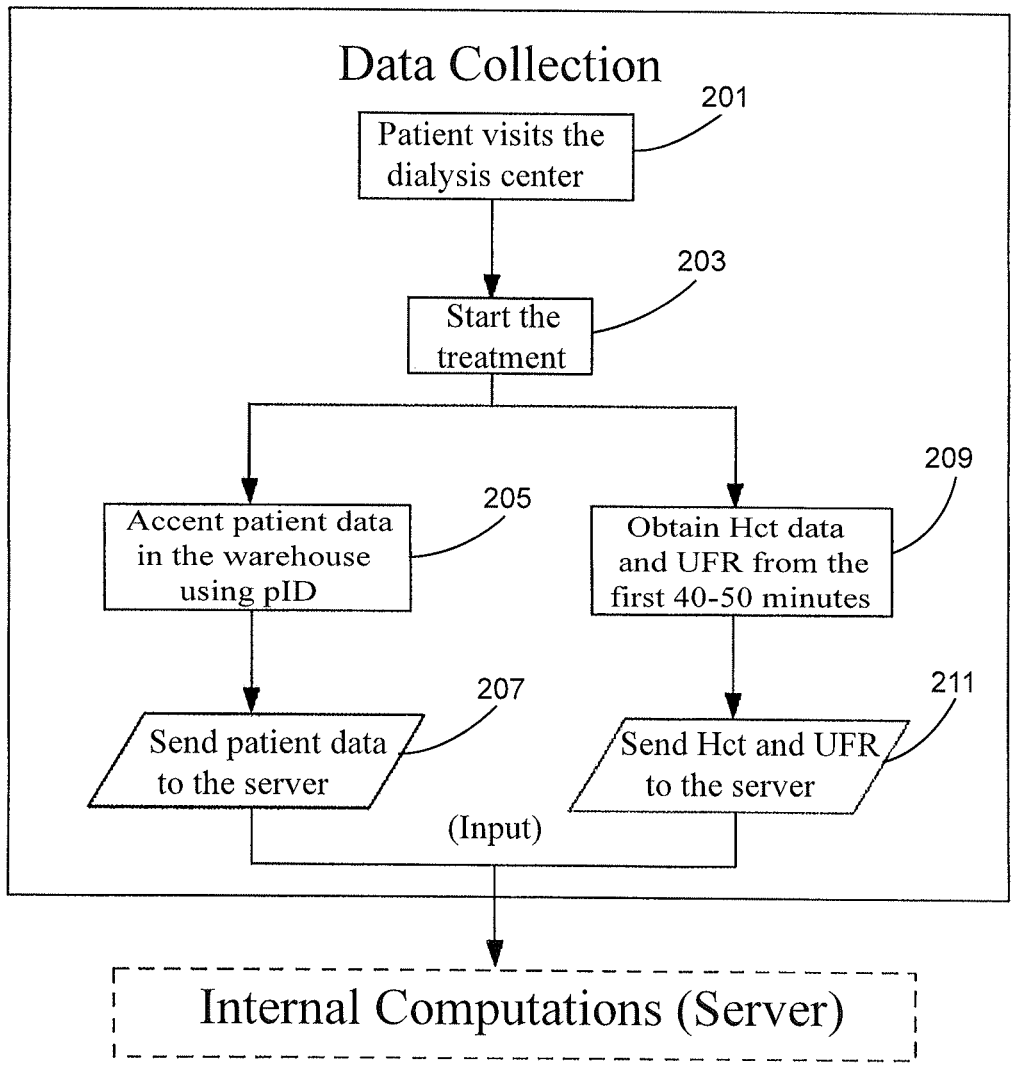
FIG. 2 is a flowchart illustrating an exemplary process for obtaining input parameters.

FIG. 2 is a flowchart illustrating an exemplary process for obtaining input parameters. The input parameters, for example, may be received by the server 120 and then used in the model-based estimations performed by the server 120. At stage 201, a patient visits the dialysis center 102, and at stage 203, a dialysis treatment for the patient is started. At stage 205, a patient ID corresponding to the patient is sent to the data warehouse 130, and at stage 207, certain patient data is communicated to the server 120. The patient data that may be passed on includes—if available for the patient—patient ID, absolute blood volume (ABV) and bioimpedance data, gender, weight, height, intradialytic weight gain (IDWG) and previous values for the indicators $L_p$, $P_c$, $P_i$, $\sigma$, $\alpha$, $\kappa$.

Additionally, in the meantime, a sensing device collects data for hematocrit (Hct) and/or relative blood volume (RBV) at stage 209. This device can be, for instance a Crit-Line Monitor or one of its successors (e.g. CliC device) or any other machine that measures either Hct or RBV with sufficient accuracy and frequency (e.g., at least 1 measurement per minute). The more accurate the measurement is, the more parameters can be identified and estimated by the server 120. After a predefined time has passed (e.g., between 20 to 50 minutes), at stage 211, the collected Hct or RBV together with the ultrafiltration profile (including the UFR) that was run up to that point and the patient ID is sent to the server 120. The server then uses the data corresponding to the treatment of the patient, as well as patient data from the data warehouse 130 (if available), to perform model-based computations (discussed in more detail below with respect to FIG. 3).

It will be appreciated that the patient ID may be used by the server 120 to merge the data from the clinic (the dialysis treatment center 102) with the patient information obtained from the data warehouse 130.

Figure 3:
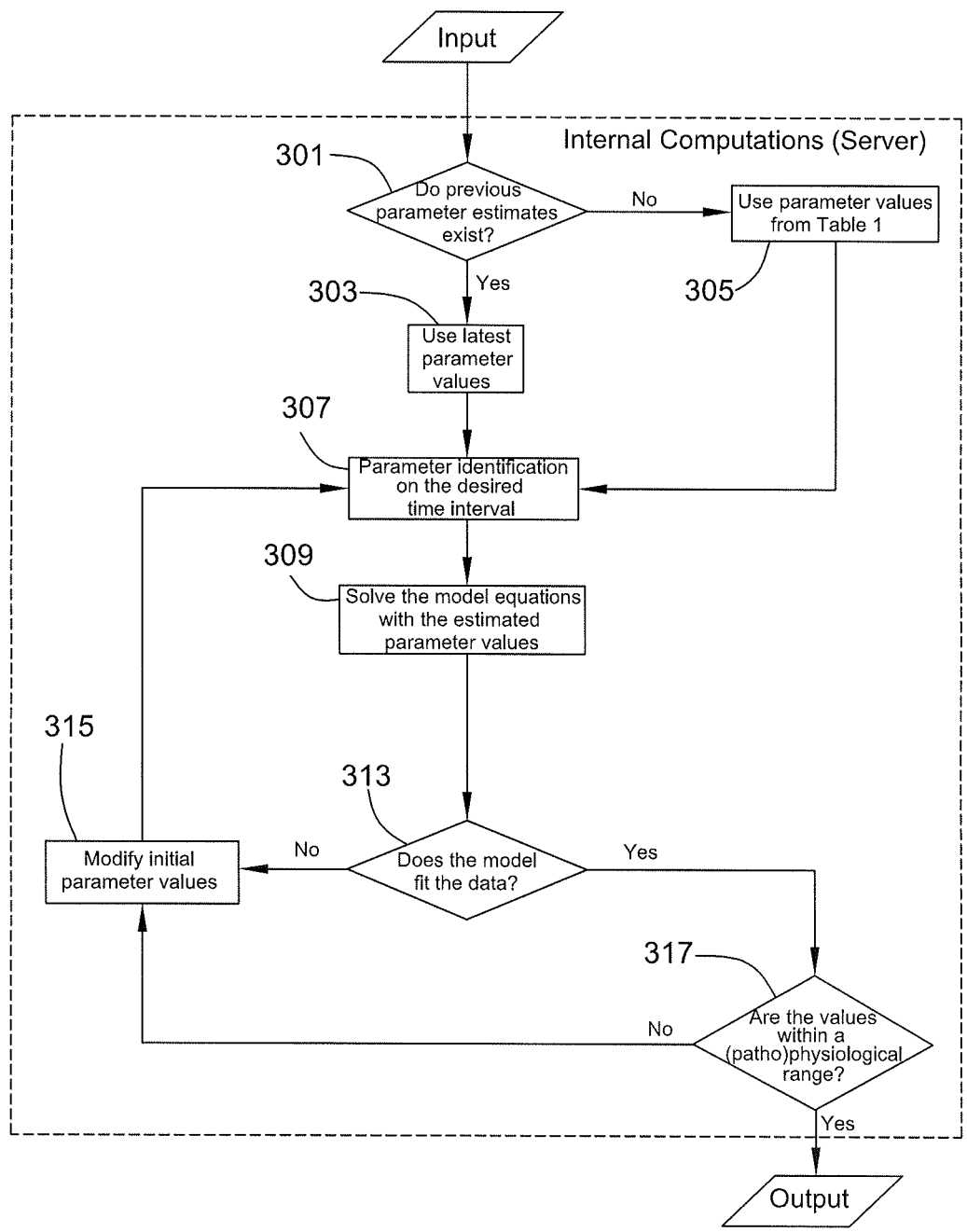
FIG. 3 is a flowchart illustrating an exemplary process for a server to perform computations based on a vascular refill model.

FIG. 3 is a flowchart illustrating an exemplary process for a server to perform computations based on a vascular refill model. The computations include processing the received information and computing estimates for the indicators $L_p$, $P_c$, $P_i$, $\sigma$, $\alpha$, and/or $\kappa$. If previous parameter estimates exist for the patient (e.g., $L_p$, $P_c$, $P_i$, $\sigma$, $\alpha$, and/or $\kappa$ values for the patient received from the data warehouse 130) at stage 301, the server at stage 303 may use those previous parameters as a starting point. If previous parameter estimates do not exist for the patient at stage 301 (e.g., for a new patient), default initial parameters may be used as the starting point (see Table 1 below) at stage 305.

Using the determined starting point, the server 120 then utilizes a mathematical model for vascular refill (as will be discussed in further detail below) to estimate values for output parameters (or "hemodialysis-related treatment parameters") $L_p$, $P_c$, $P_i$, $\sigma$, $\alpha$, and/or $\kappa$ (which are indicative of an effect of vascular refill on the patient caused by the hemodialysis). This includes performing a parameter identification on the desired time interval at stage 307, solving model equations using the initial parameter values at stage 309, plotting the model output with Hct data at stage 311, and determining whether the model fits the data at stage 313. If the model does not fit the data at stage 313, the initial values are modified at stage 315 and stages 307, 309, 311 and 313 are performed again. If the model does fit the data at stage 313, but checking the range of parameter values obtained to determine whether the values are within a (patho)physiological range at stage 317 reveals that the values are not within range the (patho)physiological range, the initial values are modified at stage 315 and stages 307, 309, 311 and 313 are performed again. If the model does fit the data at stage 313, and checking the range of parameter values obtained to determine whether the values are within a (patho)physiological range at stage 317 reveals that the values are within the (patho)physiological range, the server 120 provides one or more estimated output parameters as output so as to facilitate the performance of one or more treatment-related operations (as will be discussed below in further detail with respect to FIG. 4).

The parameter identification at stage 307 involves an inverse problem being solved several times (as will be discussed in further detail below). Additionally, solving the model equations at stage 309 involves solving the inverse problem to compute parameter estimates for $L_p$, $P_c$, $P_i$, $\sigma$, $\alpha$, and/or $\kappa$. Based on checking whether the model fits the data at stage 311, as well as checking whether the values are within a (patho)physiological range at stage 317, the computation process is repeated until reliable and meaningful parameter values are found.

Figure 4:
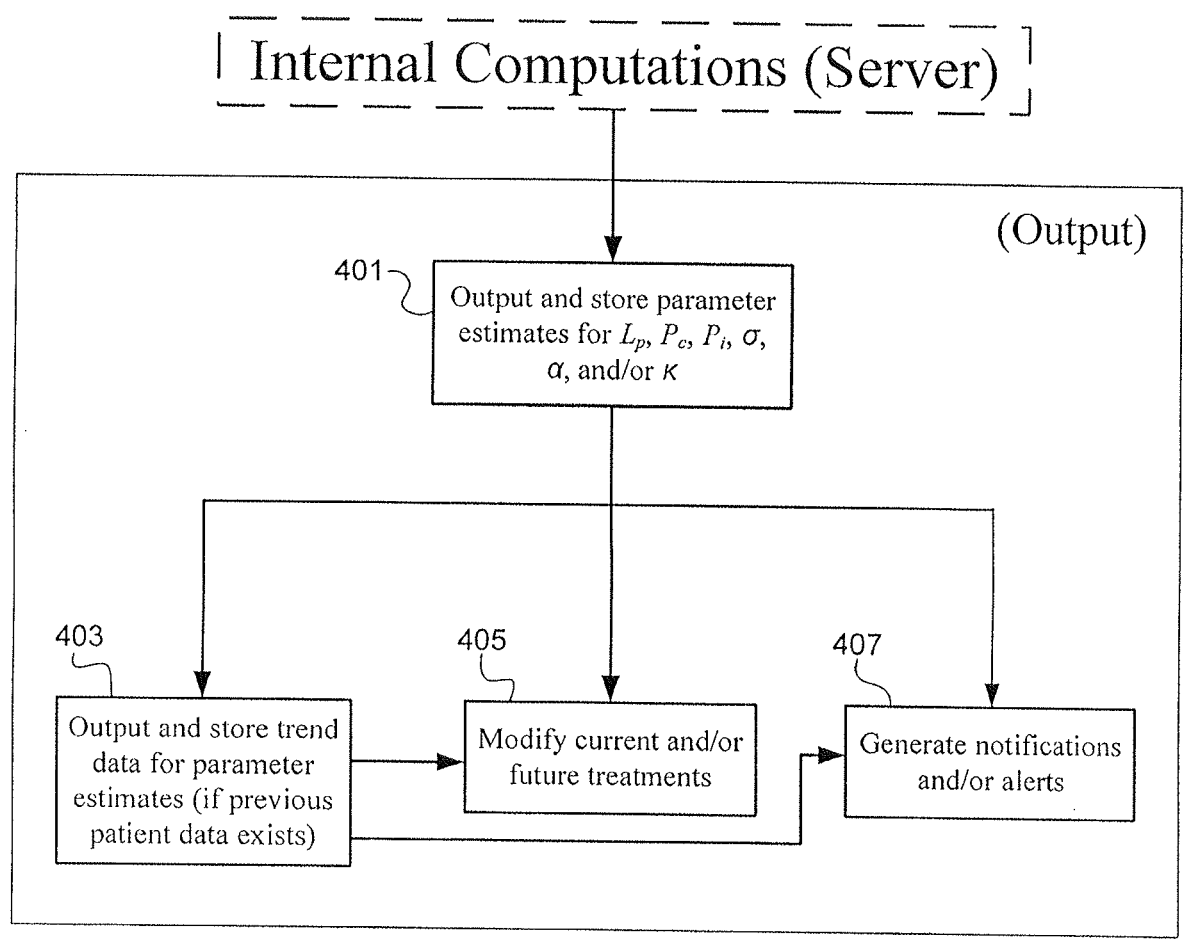
FIG. 4 is a flowchart illustrating an exemplary process for utilizing the output parameters computed by the server.

FIG. 4 is a flowchart illustrating an exemplary process for utilizing the output parameters computed by the server. In an exemplary embodiment, the server is able to estimate the following indicators within an hour of beginning hemodialysis: $L_p$, $P_c$, $P_i$, $\sigma$, $\alpha$, and/or $\kappa$. At stage 401, the estimated output parameters are output via the network 110 and communicated to the dialysis center 102. The estimated output parameters may also be output via the network 110 to the data warehouse 130 and stored. Trend data based on the estimated output parameters in combination with previously estimated output parameters for the same patient may also be output and stored at stage 403. Using the estimated output parameters from stage 401 and/or the trend data at stage 405, a current hemodialysis treatment and/or future hemodialysis treatment may be modified (for example, manual adjustments to ultrafiltration rate and/or treatment time made based on a treating physician's review of the data, and/or automatic adjustments made based on the output parameters meeting certain criteria such as exceeding certain thresholds or falling outside of certain ranges). In one example, treatment may be automatically stopped or slowed if the estimated values indicate that continued treatment at a current UFR is dangerous to the patient.

Figure 5:
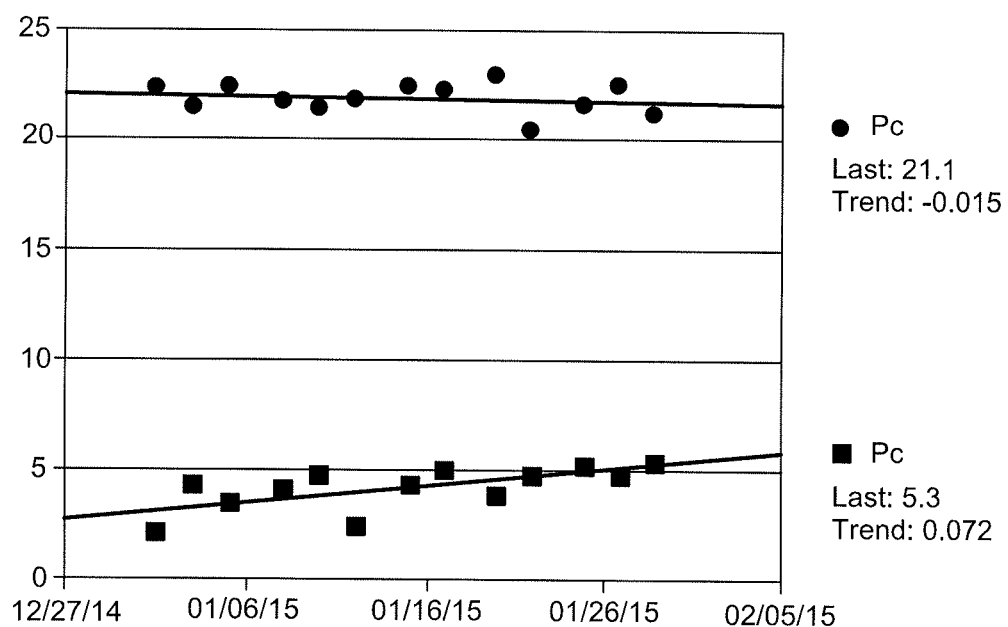
FIGS. 5 and 6 illustrate an exemplary reporting interface for certain output parameters.
Figure 6:
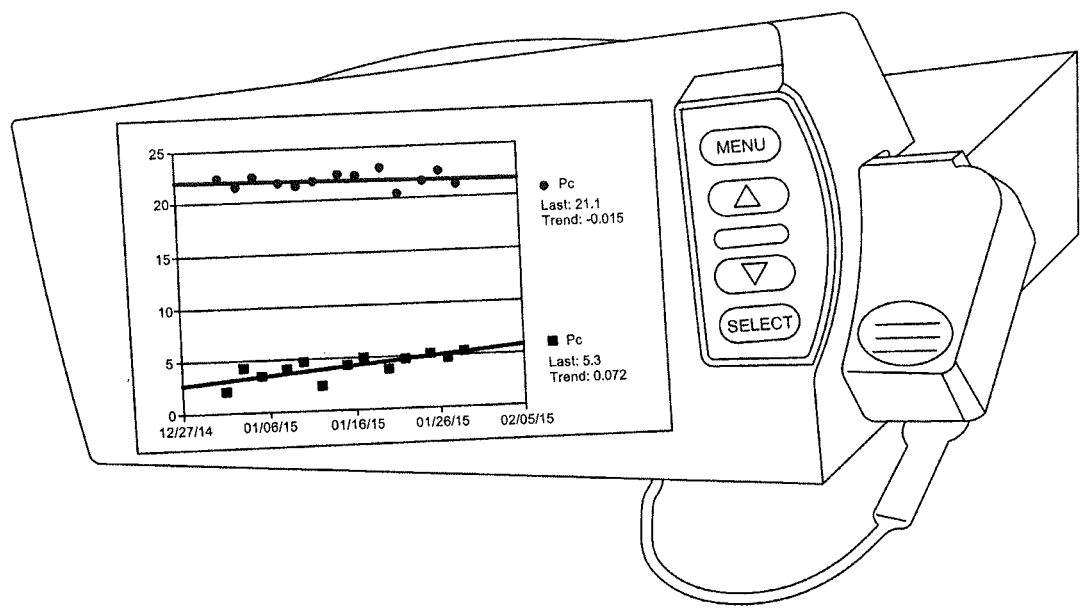

Additionally, notifications and/or alerts may be generated at stage 407. For example, treating physicians and other personnel may be notified of the estimated output parameters based on the display of the values for the estimated output parameters on a screen of a computing device at a treatment facility. They may also be otherwise notified via various forms of messaging or alerts, such as text messaging, paging, internet messaging, etc. Specific alerts, for example, relating to potential problems arising from the hemodialysis treatment, may be generated based on certain output parameters meeting certain criteria (such as exceeding or falling below a predetermined range of values or threshold, or rising/falling at a rate determined to be potentially problematic). In an example, the values of certain output parameters are presented on a screen (e.g. the display of the Crit-Line Monitor) together with normal ranges. Further, trends of the parameter values for the patient (e.g., over the last 1-3 months) may also be depicted. Examples of graphical depictions on such a display are illustrated in FIGS. 5 and 6 (which illustrate an exemplary reporting interface for certain output parameters).

When there exists previous parameter estimates for $L_p$, $P_c$, $P_i$, $\sigma$, $\alpha$, $\kappa$ for the patient, the trend over a time period (e.g., the last 1-3 months) can be computed using linear regression. The new parameter values (together with the trend, if available) are passed on to be reported at the clinic. Moreover, the new estimates are communicated to the data warehouse and stored, such that the information about the indicators will be made accessible for additional analyses. These additional analyses include but are not limited to trend analysis over time, correlational analysis with other variables, such as interdialytic weight gain, target weight, and biomarkers, such as serum albumin levels, neutrophil-to-lymphocyte ratio, C-reactive protein (CRP), and others.

Since the identified variables are indicative of (patho) physiological processes, but are not accessible to direct measurements, the estimated values will be considered for clinical decision making. For example, a high value for the filtration coefficient ($L_p$) is indicative of inflammation, which may require additional investigation to confirm the presence of inflammation. Trend data showing rising levels of $L_p$ may further be indicative of smoldering or aggravating inflammation and may require additional investigation as well. Thus, certain notifications or alerts/alarms may be triggered based on the value for $L_p$ exceeding a predetermined threshold or the rate of increase for $L_p$ exceeding a predetermined threshold.

In another example, a low value for the systemic capillary reflection coefficient ($\sigma$) is indicative of capillary leakage, sepsis, or an allergic response and/or anaphylaxis, which may require additional investigation into the source of the leakage, sepsis, or allergic response. Trend data showing falling levels of ($\sigma$) is indicative of smoldering or aggravating capillary leakage. Thus, certain notifications or alerts/alarms may be triggered based on the value for a being below a predetermined threshold or the rate of decrease for a falling below a predetermined threshold.

In another example, a high value of (or increasing trend for) hydrostatic capillary pressure ($P_c$) is indicative of autonomic dysfunction, high venous pressure, drugs, or arterial hypertension, which may require evaluation of a patient's drug prescription and/or a cardiac exam to investigate the high venous pressure. On the other hand, a low value of $P_c$ is indicative of an exhausted reserve to increase peripheral resistance, which may require measures to increase intravascular volume (e.g., lowering the UFR). Thus, certain notifications or alerts/alarms may be triggered based on the value for $P_c$ being outside a predetermined range or the rate of increase for $P_c$ exceeding a predetermined threshold. Treatment adjustments may also be made based on $P_c$ falling below a predetermined threshold, such as automatically decreasing the UFR for a current or a future treatment of the patient. The UFR may also be manually decreased by a treating physician, for example, in response to reviewing the $P_c$ information displayed at the treatment center, or in response to an automatic prompt triggered by the detection of the low $P_c$ level that gives the physician the option of decreasing the rate of and/or stopping treatment.

In yet another example, a high value of (or increasing trend for) hydrostatic interstitial pressure ($P_i$) and/or constant lymph flow rate ($\kappa$) is indicative of interstitial fluid overload, while a low value (or decreasing trend for) hydrostatic interstitial pressure ($P_i$) and/or constant lymph flow rate ($\kappa$) is indicative of interstitial fluid depletion. The clinical response here may be to re-evaluate the fluid removal rate (i.e., increasing it in the event of fluid overload and decreasing it in the event of fluid depletion) for a current and/or future treatment. As discussed above with respect to $P_c$, notifications and/or alerts/alarms may be triggered based on the hydrostatic interstitial pressure ($P_i$) and/or constant lymph flow rate ($\kappa$) falling outside respective predetermined ranges, and automatic or manual treatment modifications may be made as well.

It will be appreciated that the predetermined thresholds or ranges used in the aforementioned comparisons may be based on previous patient data, such that a predetermined threshold for one patient may differ from the predetermined threshold for another patient. Thus, outlier values with respect to the estimated output parameters may be detected and responded to appropriately (e.g., with a notification or alert/alarm, or with adjustment of a current and/or future treatment).

As discussed above, significant changes of these variables between dialysis sessions, marked trends or out of range values may be highlighted by a device at the treatment center pursuant to stage 407. In one example, an alarm flag can be used to mark questionable parameters needing further investigation by clinic personnel (e.g., by alerting clinic personnel through visual and/or audio alarms triggered by the patient monitoring device). For instance, as discussed above, a positive $P_i$ may indicate fluid overload and may be considered when target weight is prescribed. Another example is an increase of $L_p$, which may indicate an evolving inflammatory process. Such a signal may result in additional diagnostic interventions, such as measurement of CRP, clinical evaluation, blood cultures, or medical imaging.

Additionally, the output parameters discussed herein ($L_p$, $P_c$, $P_i$, $\sigma$, $\alpha$, and/or $\kappa$) may further serve as independent variables in statistical models designed to predict patient outcomes of interest. For example, the server of FIG. 1 or a separate external computing device may access the data warehouse to obtain stored parameters pertaining to a patient and make predictions regarding corresponding characteristics and trends pertaining to that patient based thereon. An illustration of relevant prediction models is provided by the discussion of logistic regression models presented in Thijssen S., Usvyat L., Kotanko P., "Prediction of mortality in the first two years of hemodialysis: Results from a validation study", Blood Purif 33:165-170 (2012), the entirety of which is incorporated by reference herein. The predictors used in those models were age, gender, race, ethnicity, vascular access type, diabetic status, pre-HD systolic blood pressure, pre-HD diastolic blood pressure, pre-HD weight, pre-HD temperature, relative interdialytic weight gain (of post-HD weight), serum albumin, urea reduction ratio, hemoglobin, serum phosphorus, serum creatinine, serum sodium, equilibrated normalized protein catabolic rate, and equilibrated dialytic and renal K*t/V (K being the combined dialytic and renal clearance for urea, t being treatment time, and V being the total urea distribution volume). Analogously, the parameters discussed herein (e.g., $L_p$, $P_c$, $P_i$, $\sigma$, $\alpha$, $\kappa$) may be used as predictors in such models, either by themselves or alongside other predictors, similar to other predictors used in predictive statistical models.

It will be appreciated that the referenced logistic regression models are only exemplary. Various different types of statistical models may be used, with categorical or continuous outcomes. Examples of models include Cox regression models, Poisson regression models, accelerated failure time models, generalized linear models, generalized additive models, classification trees, and random forests. Examples of outcomes of interest include death during a certain period of time, hospitalization (binary or count) over a certain period of time, systemic inflammation (as measured by biochemical markers, such as C-reactive protein and IL-6), and degree of fluid overload (as determined by bioimpedance or other methods).

Principles underlying the operation of the server depicted in FIG. 1, as well examples verifying these principles, are discussed in the following disclosure and in the Appendices.

Figure 7:
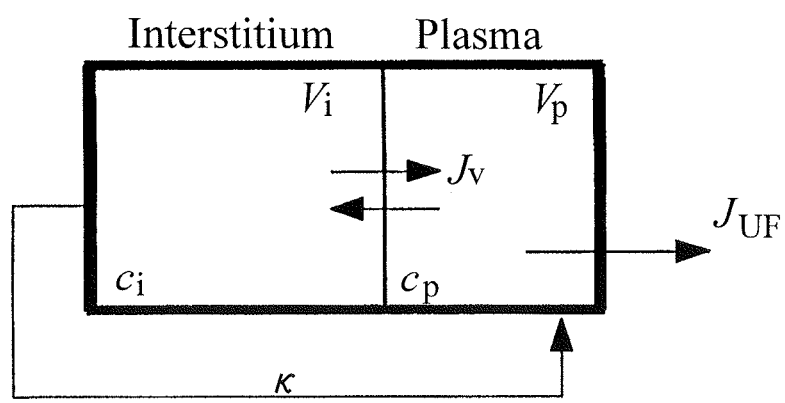
FIG. 7 is a model diagram depicting the fluid movement in the compartments.

Modeling Assumptions and Formulation:

The model of vascular refill presented herein is a two-compartment model. The blood plasma in the patient's body is lumped in one compartment and the interstitial fluid including the lymphatic system are lumped in another, namely, the plasma and interstitial compartments, respectively. The plasma and interstitium are separated by a capillary wall which is a semipermeable membrane regulating fluid exchange and protein flux. Fluid movement between plasma and interstitium is influenced by the properties of the capillary wall (reflection coefficient $\sigma$ and filtration coefficient $L_p$), and pressure gradients across the membrane (oncotic and hydrostatic pressures). Furthermore, lymph flows at a constant rate and protein concentration from the interstitial into the plasma compartment. The model is formulated to describe the short-term dynamics of vascular refill for a period of about one hour. Hence, some of the model assumptions are only valid when considering a short time duration. FIG. 7 is a model diagram depicting the fluid movement in the compartments.

Assumptions:

(1) The plasma compartment ($V_p$) is connected to the interstitial compartment ($V_i$) which includes the lymphatic system in the microvasculature. $V_p$ is open at the dialyzer membrane where protein-free ultrafiltrate is removed during ultrafiltration.

(2) The ultra filtration rate ($J_{UF}$) set at the dialysis machine determines the flow across the dialyzer.

(3) A constant lymph flow ($\kappa$) with constant protein concentration (a) goes from interstitium into plasma.

(4) Net flow between $V_p$ and $V_i$ is determined by the Starling pressures.

(5) Colloid osmotic pressure relationships are determined by protein concentrations.

(6) The hydrostatic pressure gradient is assumed to be constant.

(7) The hydrostatic capillary pressure ($P_c$) is constant.

(8) The net protein flux ($J_s$) is the sum of both convective and diffusive fluxes across the capillary wall.

By Assumptions 1-3, the change in plasma volume at time t is governed by $$\frac{dV_p(t)}{dt} = J_v(t) + \kappa - J_{UF}(t), \quad (1)$$

where $J_v(t)$ represents the amount of fluid crossing the capillary membrane at a certain time t, $\kappa$ is the lymph flow from interstitium to plasma, and $J_{UF}(t)$ is the ultrafiltration rate. The fluid movement across the membrane depends on the net imbalance between effective colloid osmotic and pressure gradients (Assumption 4). Following Starling's hypothesis, we have $$J_v(t) = L_p(\sigma(\pi_p(t) - \pi_i(t)) - (P_c(t) - P_i(t))), \quad (2)$$

with $L_p$ denoting the filtration coefficient (which is hydraulic conductivity×surface area), $\sigma$ is the osmotic reflection coefficient, $\pi_p(t)$, $\pi_i(t)$ are the plasma and interstitial colloid osmotic pressures, respectively, and $P_c(t)$, $P_i(t)$ are the hydrostatic capillary and interstitial pressures, respectively, at a given time t. Plasma proteins leak into the interstitium and the degree of leakiness can be quantified by Staverman's osmotic reflection coefficient $\sigma$ ranging from 0 to 1; where a value $\sigma=1$ means perfect reflection, and thus no leakage of the specified solute. A quadratic polynomial approximation is used to describe oncotic pressures, though other approximations are possible:

$$\pi_p(t) = a_{p1}c_p(t) + a_{p2}c_p(t)^2,$$

$$\pi_i(t) = a_{i1}c_i(t) + a_{i2}c_i(t)^2. \quad (3)$$

where $c_p(t)$, $c_i(t)$ are protein concentrations in plasma and interstitium, respectively, at a given time t. Further details can be found in Appendix A.

To describe capillary refill dynamics during short-pulse ultrafiltration, it is assumed that the pressure difference between $P_c(t)$ and $P_i(t)$ is constant (Assumption 6). Since $P_c$ is well autoregulated over a wide range of blood pressures, it is further assumed that it remains constant for short duration, that is, $P_c(t) \approx P_c$ (Assumption 7). As a consequence of Assumptions 6 and 7, $P_i(t)$ is constant during short-time duration, that is, $P_i(t) \approx P_i$.

The net flux of proteins between plasma and interstitium is the sum of convective and diffusive fluxes across the capillary wall and protein backflow from the lymph (Assumption 8). Thus, we have $$J_s(t) = \begin{cases} J_v(t)(1-\sigma)c_i(t) - PS(c_p(t)-c_i(t))\dfrac{x(t)}{e^{x(t)}-1} + \alpha\kappa & \text{if } J_v(t) > 0, \\ \alpha\kappa & \text{if } J_v(t) = 0, \\ J_v(t)(1-\sigma)c_p(t) - PS(c_p(t)-c_i(t))\dfrac{x(t)}{e^{x(t)}-1} + \alpha\kappa & \text{if } J_v(t) < 0, \end{cases} \quad (4)$$

where PS is the permeability-surface area product, a is the concentration of protein backflow from the lymph, and x is the Peclet number describing the convective flux relative to the diffusive capacity of the membrane:

$$x(t) = \frac{J_v(t)(1-\sigma)}{PS}. \quad (5)$$

When $J_v(t) \geq 0$, protein flows into the plasma while when $J_v(t) < 0$ protein goes into the interstitium. Equation (4) can be rewritten as $$J_s(t) = \begin{cases} J_v(t)(1-\sigma)\left(c_i(t) - \dfrac{c_p(t)-c_i(t)}{e^{x(t)}-1}\right) + \alpha\kappa & \text{if } J_v(t) > 0, \\ \alpha\kappa & \text{if } J_v(t) = 0, \\ J_v(t)(1-\sigma)\left(c_p(t) - \dfrac{c_p(t)-c_i(t)}{e^{x(t)}-1}\right) + \alpha\kappa & \text{if } J_v(t) < 0, \end{cases} \quad (6)$$

Note that $J_s(t)$ is a continuous function.

Since the plasma protein concentration can be expressed in terms of its mass and plasma volume as $$c_p(t) = \frac{m_p(t)}{V_p(t)}$$

and the change of protein mass in the plasma at time t is determined by the net protein flux as $$\frac{dm_p(t)}{dt} = J_s(t), \quad (7)$$

the change in plasma protein $$\frac{dc_p(t)}{dt} = \frac{J_s(t) - c_p(t)\dfrac{dV_p(t)}{dt}}{V_p(t)}. \quad (8)$$

The change in interstitial volume is governed by the volume lost to plasma and the lymphatic system and thus, $$\frac{dV_i(t)}{dt} = -J_v(t) - \kappa. \quad (9)$$

By a similar argument, the mass of proteins that goes to the plasma compartment is the loss term in the interstitium compartment and thus the change of the interstitial protein mass is $$\frac{dm_i(t)}{dt} = -J_s(t), \quad (10)$$

and with interstitial protein concentration as $$c_i(t) = \frac{m_i(t)}{V_i(t)}$$

the change in interstitial protein concentration is given by $$\frac{dc_i(t)}{dt} = \frac{-J_s(t) + c_i(t)(J_v(t) + \kappa)}{V_i(t)}. \quad (11)$$

Model Equations:

The dynamics of the two-compartment model is described by the following system of ordinary differential equations $$\begin{cases} \dfrac{dV_p}{dt} = J_v + \kappa - J_{UF}, \\ \dfrac{dc_p}{dt} = \dfrac{J_s - c_p(J_v + \kappa - J_{UF})}{V_p}, \\ \dfrac{dV_i}{dt} = -J_v - \kappa, \\ \dfrac{dc_i}{dt} = \dfrac{J_s + c_i(J_v + \kappa)}{V_i}, \end{cases} \quad (12)$$

where $$J_v = L_p(\sigma((a_{p_1}c_p + a_{p_2}c_p^2) - (a_{i_1}c_i + a_{i_2}c_i^2)) - (P_c - P_i)),$$

$$J_s = \begin{cases} J_v(1-\sigma)\left(c_i - \dfrac{c_p - c_i}{e^x - 1}\right) + \alpha\kappa & \text{if } J_v > 0, \\ \alpha\kappa & \text{if } J_v = 0, \\ J_v(1-\sigma)\left(c_p - \dfrac{c_p - c_i}{e^x - 1}\right) + \alpha\kappa & \text{if } J_v < 0, \end{cases}$$

and $$x = \frac{J_v(1-\sigma)}{PS}.$$

Model Output:

In order to estimate certain parameters, the model is compared to measurement data. The Crit-Line Monitor device is an exemplary device that provides readings of the hematocrit concentration and oxygen saturation during hemodialysis. It is a non-invasive method based on an optical sensor technique. The sensor is attached to a blood chamber and is placed in-line between the arterial blood tubing set and the dialyzer. The measurements are based on both the absorption properties of the hemoglobin molecule and the scattering properties of red blood cells. Hematocrit levels can be expressed in terms of the model state variables, namely, $V_p$, $c_p$, $V_i$, and $c_i$ for parameter identification.

Let $BV(t)$ and $V_p(t)$ denote the blood volume and the plasma volume, respectively, at time t. Note that $$V_p(t) - V_p(0) = BV(t) - BV(0). \quad (13)$$

Expressing the blood volume in terms of plasma volume and the hematocrit in Eq. (13) and rearranging the terms yields $$V_p(t) - V_p(0) = \frac{V_p(t)}{1 - Hct(t)} - \frac{V_p(0)}{1 - Hct(0)}$$

$$Hct(t) = \frac{(1 - Hct(0))V_p(t) + Hct(0)V_p(0) - (1 - Hct(0))V_p(t)}{(1 - Hct(0))V_p(t) + Hct(0)V_p(0)}$$

Therefore, Hct at time t can be expressed in terms of initial hematocrit, initial plasma volume and $V_p$ at time t as follows $$Hct(t) = \frac{Hct(0)V_p(0)}{(1 - Hct(0))V_p(t) + Hct(0)V_p(0)} = \frac{1}{H_0 V_p(t) + 1} \quad (14)$$

where $$H_0 = \frac{1 - Hct(0)}{Hct(0)V_p(0)}. \quad (15)$$

Simulations:

First, some theoretical results are presented assigning values to the parameters found in the literature. Table 1 provides the list of parameters, its meaning, corresponding values and units used in the model.

For model simulation, the following initial conditions are considered:

TABLE 1

Parameter values

| Parameter | Meaning | Value | Range | Unit |
|---|---|---|---|---|
| $L_p$ | filtration coefficient | 1.65 | 1.65 ± 1.92 | mL/mmHg/min |
| σ | systemic capillary reflection coefficient | 0.9 | 0.75-0.95 | |
| $P_c$ | hydrostatic capillary pressure | 21.1 | 21.1 ± 4.9 | mmHg |
| $P_i$ | hydrostatic interstitial pressure | 2 | −1.5-4.6 | mmHg |
| $a_{p1}$ | coefficient of $c_p$ in Eq. (3) | 0.1752 | | mmHg(mL/mg) |
| $a_{p2}$ | coefficient of $c_p^2$ in Eq. (3) | 0.0028 | | mmHg(mL/mg)$^2$ |
| $a_{i1}$ | coefficient of $c_i$ in Eq. (3) | 0.2336 | | mmHg(mL/mg) |
| $a_{i2}$ | coefficient of $c_i^2$ in Eq. (3) | 0.0034 | | mmHg(mL/mg)$^2$ |
| PS | permeability surface area product | 0.45 | | m/min |
| κ | constant lymph flow rate | 1.5 | 1.39-2.78 | mL/min |
| $J_{UF}$ | ultrafiltration rate | 15 | (900 mL/hour) | mL/min |

Initial plasma colloid osmotic pressure $\pi_p$ is known from which initial plasma protein concentration $c_p$ is obtained using Eq. (3). See Appendix B.

Initial interstitial colloid osmotic pressure $\pi_i$, interstitial protein concentration $c_i$ and constant protein concentration from the lymph flow a are computed assuming equilibrium prior to ultrafiltration, that is, lymphatic flow balances capillary filtration. See Appendix B.

Initial interstitial volume $V_i$ is 4.3 times initial plasma volume $V_p$, that is, $V_i$=4.3 $V_p$. This is based on data from dialysis patients.

The predialysis plasma colloid osmotic pressure of $\pi_p^*$=28 mmHg has been reported. This value is used to compute the initial $c_p$ and $c_i$. The computed value for the protein concentration assuming equilibrium is α=24.612. Initial plasma volume is set at 4000 mL and the initial interstitial volume is calculated based on the volume relation mentioned above. The initial values for the state variables are listed in Table 2.

TABLE 2

Computed equilibrium/initial values

| State | Meaning | Value | Unit |
|---|---|---|---|
| $V_p^0$ | initial plasma volume | 4000 | mL |
| $c_p^0$ | initial plasma protein concentration | 73.4940 | mg/mL |
| $V_i^0$ | initial interstitial volume | 17200 | mL |
| $c_i^0$ | initial interstitial protein concentration | 24.4153 | mg/mL |

Figure 8:
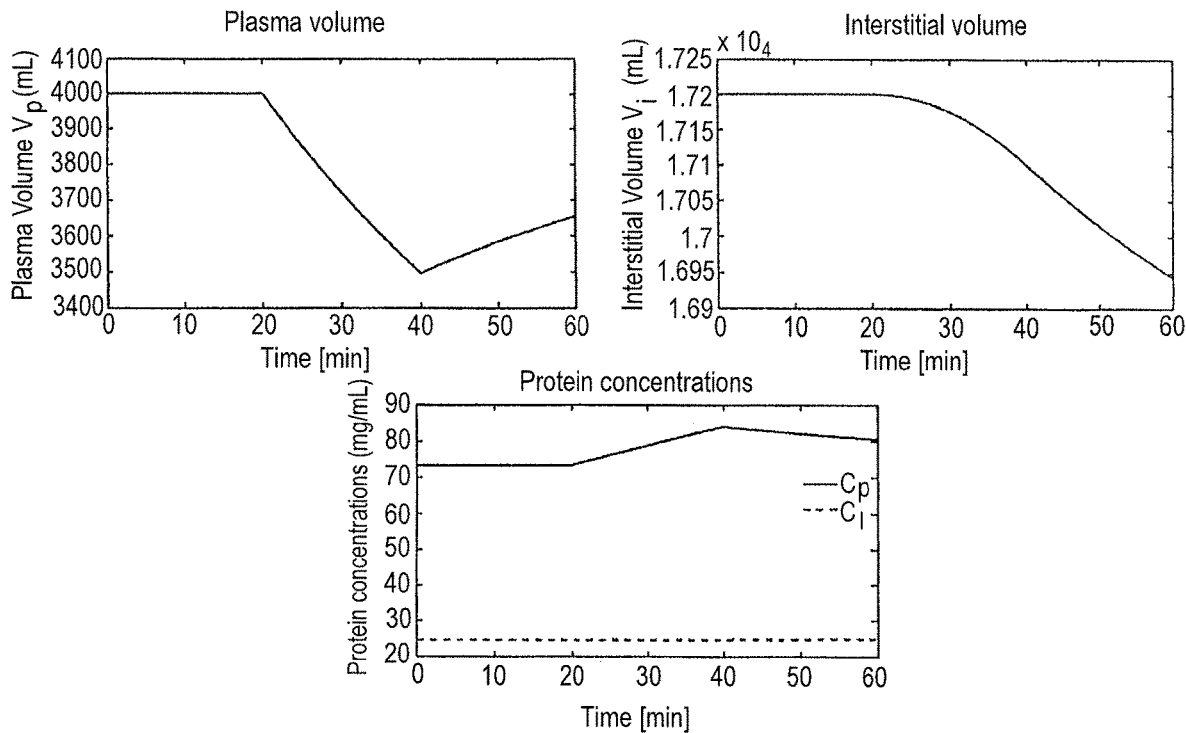
FIG. 8 illustrates the dynamical behavior of the model state variables for an hour where $J_{UF}=30$ mL/min for 20 minutes on $t \in [20, 40]$ and $J_{UF}=0$ for $t \in [0, 20)$ and $t \in (40,60]$.

The period of one hour is divided into three phases, namely: rest phase, ultrafiltration phase, and refill phase. During rest and refill phases, $J_{UF}$ is set to 0 and during ultrafiltration (UF) phase, $J_{UF}$ is set above the regular UF rate. FIG. 8 illustrates the dynamical behavior of the model state variables for an hour where $J_{UF}$=30 mL/min for 20 minutes on t ∈ [20, 40] and $J_{UF}$=0 for t ∈ [0, 20) and t ∈ (40,60]. The upper left panel shows that $V_p$ decreases during fluid removal. When the ultrafiltration is turned off, an increase in $V_p$ is observed signifying the movement of fluid from the interstitium to the plasma which indicates vascular refilling. On the upper right panel, $V_i$ decreases during the UF and refilling phases even when there is no ultrafiltration. Thus, fluid continues to move from interstitium to plasma and hence a fluid loss in this compartment. The bottom panel depicts the dynamics of plasma and interstitial protein concentrations during the given intervention. Notice that $c_p$ increases during ultrafiltration and decreases slightly during refill phase while $c_i$ does not change significantly. Overall, the model dynamics reflect the qualitative physiological behavior as one would expect during a short-pulse ultrafiltration.

Figure 9:
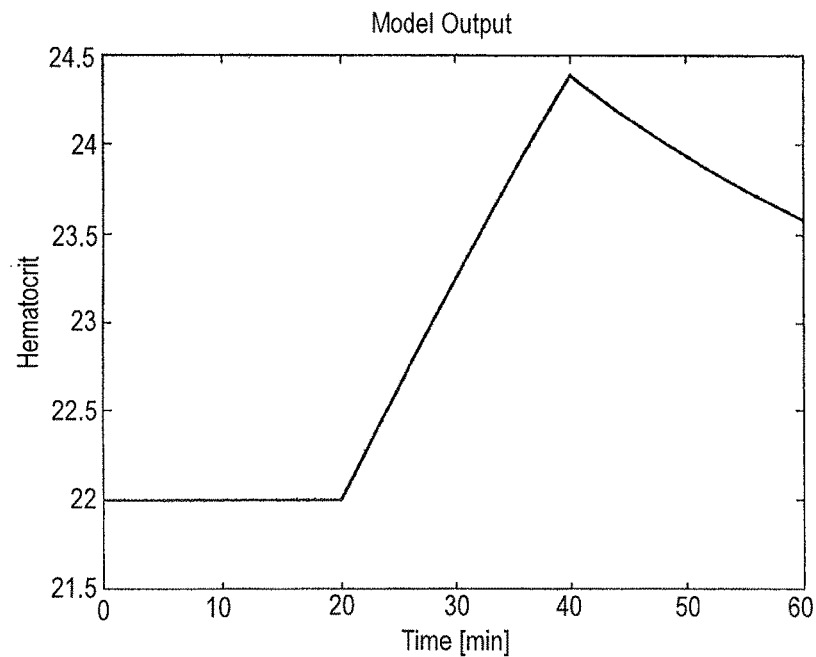
FIG. 9 illustrates hematocrit levels as model output during a rest phase for $t \in [0, 20)$ minutes, UF at $J_{UF}=30$ mL/min for $t \in [20, 40]$ minutes, and refill phase for $t \in (40, 60]$ minutes.

Hematocrit is initially set at Hct(0)=22 and then Eq. (14) is used to obtain a plot for the model output. FIG. 9 illustrates hematocrit levels as model output during a rest phase for t ∈ [0, 20) minutes, UF at $J_{UF}$=30 ml/min for t ∈ [20, 40] minutes, and refill phase for t ∈ (40, 60] minutes. As expected, hematocrit level increases during ultrafiltration since it is assumed that the red blood cell mass does not change while fluid is removed.

Sensitivity Analysis and Subset Selection:

Sensitivity analysis and subset selection provide insights on the influence of certain parameters on the model output and on the identifiability of parameters with regard to specific measurements. Further, the information of these analyses can be used for experimental design. It helps in making informed decisions on the type of measurements, the frequency and the precision of the specific measurements needed to identify parameters. In the context of this application, it is important to ensure that with the gathered data it is indeed possible to identify the parameters we are interested in.

Traditional and Generalized Sensitivity Functions:

In simulation studies, the traditional sensitivity functions (TSFs) are frequently used to assess the degree of sensitivity of a model output with respect to various parameters on which it depends. It shows what parameters influence the model output the most or the least. The more influential changes in a parameter on the model output, the more important it is to assign accurate values to that parameter. On the other hand, for parameters which are less sensitive it suffices to have a rough estimate for the value. To obtain information content on the parameters, the model output needs to be either a state variable of the system or expressible as one (or more) of the state variables. Here, a relationship is established between the model output (hematocrit) and a state variable (plasma volume $V_p$) (see above).

The generalized sensitivity functions (GSFs) provide information on the sensitivity of parameter estimates with respect to model parameters. It describes the sensitivity of parameter estimates with respect to the observations or specific measurements. Note, it is assumed that the measurement error is normally distributed with a given standard deviation. Some details on sensitivities are provided in Appendix C. Based on the GSFs, one can assess if the parameters of interest are well-identifiable assuming a priori measurement error, measurement frequency and nominal parameter values.

Sensitivity Equations for the Vascular Refill Model:

Let $y(t) = Hct(t)$, i.e. the hematocrit level at time t is defined as the model output (see Eq. (14)). The sensitivity of the model output with respect to the parameter $L_p$ can be determined as follows $$s_{L_p} = \frac{L_p}{y(t)} \frac{\partial y(t)}{\partial L_p}$$

$$= \frac{L_p}{\frac{1}{H_0 V_p(t) + 1}} \left( \frac{-H_0}{(H_0 V_p(t) + 1)^2} \right) \frac{\partial V_p(t)}{\partial L_p}$$

which can be simplified as $$s_{L_p} = -\frac{L_p H_0}{H_0 V_p(t) + 1} \frac{\partial V_p(t)}{\partial L_p} \quad (16)$$

where $$H_0 = \frac{1 - Hct(0)}{Hct(0) V_p(0)}.$$

Sensitivities with respect to other parameters can be obtained similarly and they are given as $$s_\sigma = \frac{\sigma}{y(t)} \frac{\partial y(t)}{\partial \sigma} = -\frac{\sigma H_0}{H_0 V_p(t) + 1} \frac{\partial V_p}{\partial \sigma},$$

$$s_{PS} = \frac{PS}{y(t)} \frac{\partial y(t)}{\partial PS} = -\frac{PS H_0}{H_0 V_p(t) + 1} \frac{\partial V_p}{\partial PS},$$

$$s_{P_c} = \frac{P_c}{y(t)} \frac{\partial y(t)}{\partial P_c} = -\frac{P_c H_0}{H_0 V_p(t) + 1} \frac{\partial V_p}{\partial P_c},$$

$$s_{P_i} = \frac{P_i}{y(t)} \frac{\partial y(t)}{\partial P_i} = -\frac{P_i H_0}{H_0 V_p(t) + 1} \frac{\partial V_p}{\partial P_i},$$

$$s_{a_{P_1}} = \frac{a_{P_1}}{y(t)} \frac{\partial y(t)}{\partial a_{P_1}} = -\frac{a_{P_1} H_0}{H_0 V_p(t) + 1} \frac{\partial V_p}{\partial a_{P_1}},$$

$$s_{a_{P_2}} = \frac{a_{P_2}}{y(t)} \frac{\partial y(t)}{\partial a_{P_2}} = -\frac{a_{P_2} H_0}{H_0 V_p(t) + 1} \frac{\partial V_p}{\partial a_{P_2}},$$

$$s_{a_{i_1}} = \frac{a_{i_1}}{y(t)} \frac{\partial y(t)}{\partial a_{i_1}} = -\frac{a_{i_1} H_0}{H_0 V_p(t) + 1} \frac{\partial V_p}{\partial a_{i_1}},$$

$$s_{a_{i_2}} = \frac{a_{i_2}}{y(t)} \frac{\partial y(t)}{\partial a_{i_2}} = -\frac{a_{i_2} H_0}{H_0 V_p(t) + 1} \frac{\partial V_p}{\partial a_{i_2}},$$

-continued $$s_\kappa = \frac{\kappa}{y(t)} \frac{\partial y(t)}{\partial \kappa} = -\frac{\kappa H_0}{H_0 V_p(t) + 1} \frac{\partial V_p}{\partial \kappa},$$

$$s_\alpha = \frac{\alpha}{y(t)} \frac{\partial y(t)}{\partial \alpha} = -\frac{\alpha H_0}{H_0 V_p(t) + 1} \frac{\partial V_p}{\partial \alpha},$$

$$s_{J_{UF}} = \frac{J_{UF}}{y(t)} \frac{\partial y(t)}{\partial J_{UF}} = -\frac{J_{UF} H_0}{H_0 V_p(t) + 1} \frac{\partial V_p}{\partial J_{UF}}.$$

The derivatives of the states with respect to the parameters $\partial x(t)/\partial p_k$, $\partial V_p(t)/\partial L_p$, etc. can be found in Appendix C.4.

Figure 10:
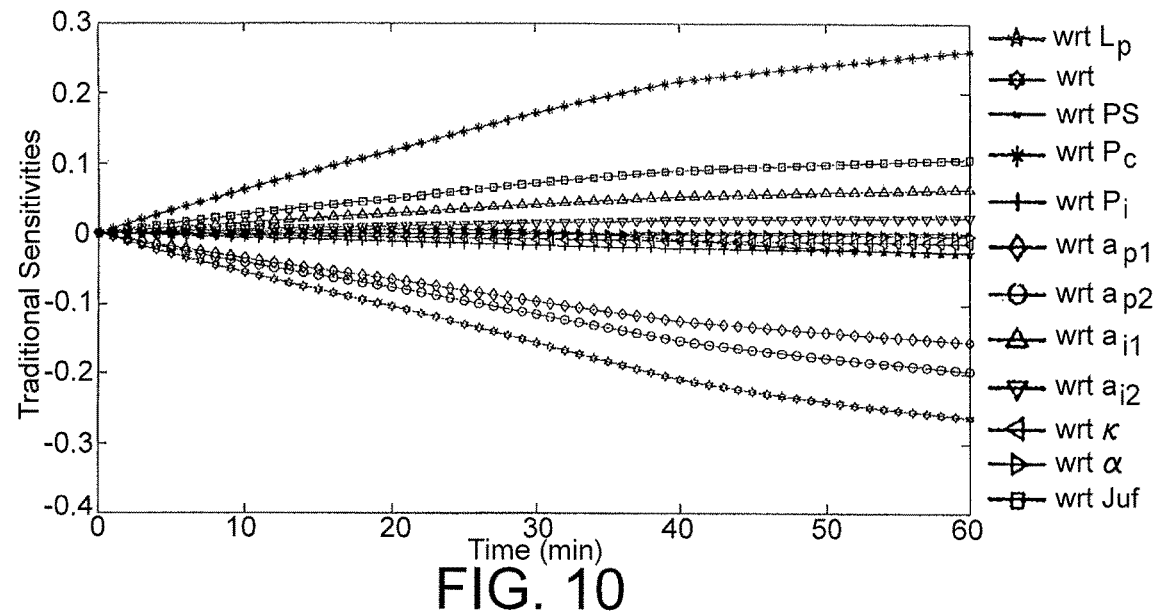
FIGS. 10 and 11 are plots illustrating traditional sensitivities of model output with respect to certain parameters.
Figure 11:
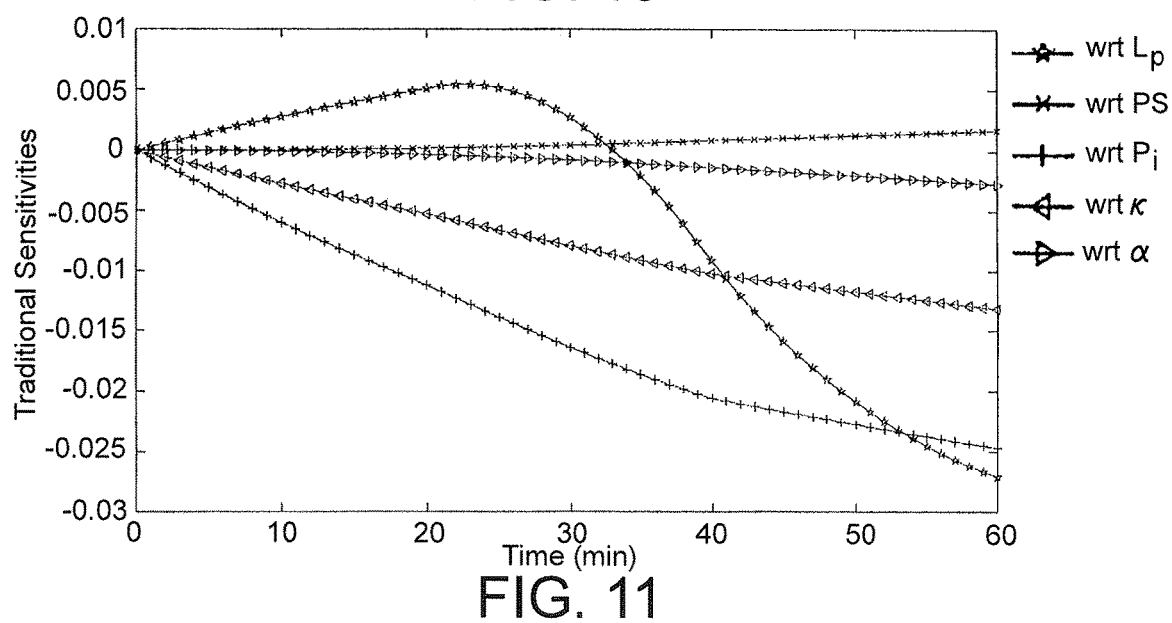

FIGS. 10 and 11 are plots illustrating traditional sensitivities of model output with respect to certain parameters. The magnitude of TSFs determines how sensitive the model output is to a specific parameter in a given time interval. That is, TSFs with greater magnitude have higher sensitivities in a certain period. Plots of TSFs corresponding to the rest, UF and refill phases discussed above are shown in FIG. 10. It can be seen that $L_p$ and a have high sensitivities. Thus, it can be expected that a unit change in these parameters will have a significant influence in the model output dynamics compared to a unit change in other parameters. FIG. 11 depicts the TSFs of parameters with smaller magnitude only. It also illustrates that parameter $L_p$ becomes more sensitive on certain times.

Subset Selection:

Before an actual parameter identification is carried out, one can choose a priori which parameters can be estimated given a data set. A subset selection algorithm described in Appendix C.3 and in Cintrón-Arias A, Banks H T, Capaldi A, Lloyd A L "A sensitivity matrix based methodology for inverse problem formulation" J Inv Ill-posed Problems 17:545-564 (2009), the entirety of which is incorporated by reference herein, chooses the parameter vectors that can be estimated from a given set of measurements using an ordinary least squares inverse problem formulation. The algorithm requires prior knowledge of a nominal set of values for all parameters along with the observation times for data. Among the given set of parameters, the algorithm searches all possible choices of different parameters and selects those which are identifiable. It minimizes a given uncertainty quantification, for instance, by means of asymptotic standard errors. Overall, subset selection gives information on local identifiability of a parameter set for a given data. Further, it gives a quantification whether a parameter can be identified or not.

The subset selection algorithm is used to select best combination of parameters from the given set of model parameters based on a defined criteria. As mentioned above, prior knowledge of measurement variance $\sigma_0$, measurement frequency and nominal parameter values $\theta_0$ are required. These values are needed to compute the sensitivity matrix, the Fisher Information Matrix (FIM) and the corresponding covariance matrix. In the current study, a selection score $\alpha(\theta_0)$ is set to be the maximum norm of the coefficients of variation for $\theta$ (see Appendix C.3 for more details). The subset of parameters are chosen with the minimal $\alpha(\theta_0)$. The condition number $cond(F(\theta_0))$ determines the ratio between the largest and the smallest eigenvalue of the FIM. If $cond(F(\theta_0))$ is too large, FIM is ill-posed and the chosen subset of parameters might be difficult to identify or even unidentifiable.

Table 3 presents the chosen parameters out of the 12 model parameters with the selection score and condition number of the corresponding FIM. It is assumed that measurement can be obtained at the frequency of 10 Hz, the standard error is 0.1 (variance is 0.01) and the nominal parameter values are given in Table 1. Note that $L_p$, $P_c$, and σ are the three best parameter combinations chosen. This method suggests that these parameters can be identified given the measurements with properties mentioned earlier.

TABLE 3

Subset selection choosing from 12 parameters
$(L_p, \sigma, PS, P_c, P_i, a_{p_1}, a_{p_2}, a_{i_1}, a_{i_2}, \kappa, \alpha, J_{UF})$

| No. | Parameter vector θ | α (θ₀) | cond(F (θ₀)) |
|---|---|---|---|
| 2 | $(L_p, P_c)$ | 3.05 × 10⁻⁵ | 5.3712 |
| 3 | $(L_p, \sigma, P_c)$ | 0.00040641 | 3.0162 × 10⁷ |
| 4 | $(\sigma, a_{p_2}, a_{i_2}, \alpha)$ | 0.003508 | 2.0462 × 10¹⁴ |
|   | $(L_p, \sigma, P_c, \alpha)$ | 0.0036051 | 3.812 × 10⁹ |
| 5 | $(L_p, \sigma, a_{p_1}, a_{p_2}, \alpha)$ | 0.024172 | 2.6421 × 10¹⁴ |

Since hematocrit is a measurement that can be obtained using the Crit-Line Monitor device (among other ways), some parameters need not be estimated using this observation. Specifically, $a_{p1}$, $a_{p2}$, $a_{i1}$, $a_{i2}$ are not in top priority to be identified because protein concentration measurements might be necessary for this purpose. Also, the ultrafiltration rate $J_{UF}$ is an outside perturbation introduced in the system which can be set a priori. Table 4 shows the parameter selection of the algorithm choosing from 7 parameters. It is important to note that $L_p$, $P_c$, σ are selected which are of significant relevance in this example.

TABLE 4

Subset selection choosing from 7 parameters
$(L_p, \sigma, PS, P_c, P_i, \kappa, \alpha,)$

| No. | Parameter vector θ | α (θ₀) | cond(F (θ₀)) |
|---|---|---|---|
| 2 | $(L_p, P_c)$ | 3.05 × 10⁻⁵ | 5.3712 |
| 3 | $(L_p, \sigma, P_c)$ | 0.00040641 | 3.0162 × 10⁷ |
| 4 | $(L_p, \sigma, P_c, \kappa)$ | 0.0053168 | 1.0971 × 10⁸ |
| 5 | $(L_p, \sigma, PS, P_c, \kappa)$ | 1.783 | 5.1709 × 10¹² |

Model Identification:

Model identifiability is assessed to determine parameters from measured data. The term refers to the issue of ascertaining unambiguous and accurate parameter estimation. Parameter estimation determines a parameter set such that the model output is as close as possible to the corresponding set of observations. This accounts for minimizing a measure of error for the difference between model output and measurements. It should be noted that the quality of the parameter estimates depends on the error criterion, model structure and fidelity of the available data.

To test the adaptability of the current model, a patient's hematocrit data is used. Though the measurement obtained with varying ultrafiltration profiles was originally collected for a different purpose, it can be shown that the present model adapts to the given set of observations despite this limitation. In particular, some key parameters can be identified.

Figure 12:
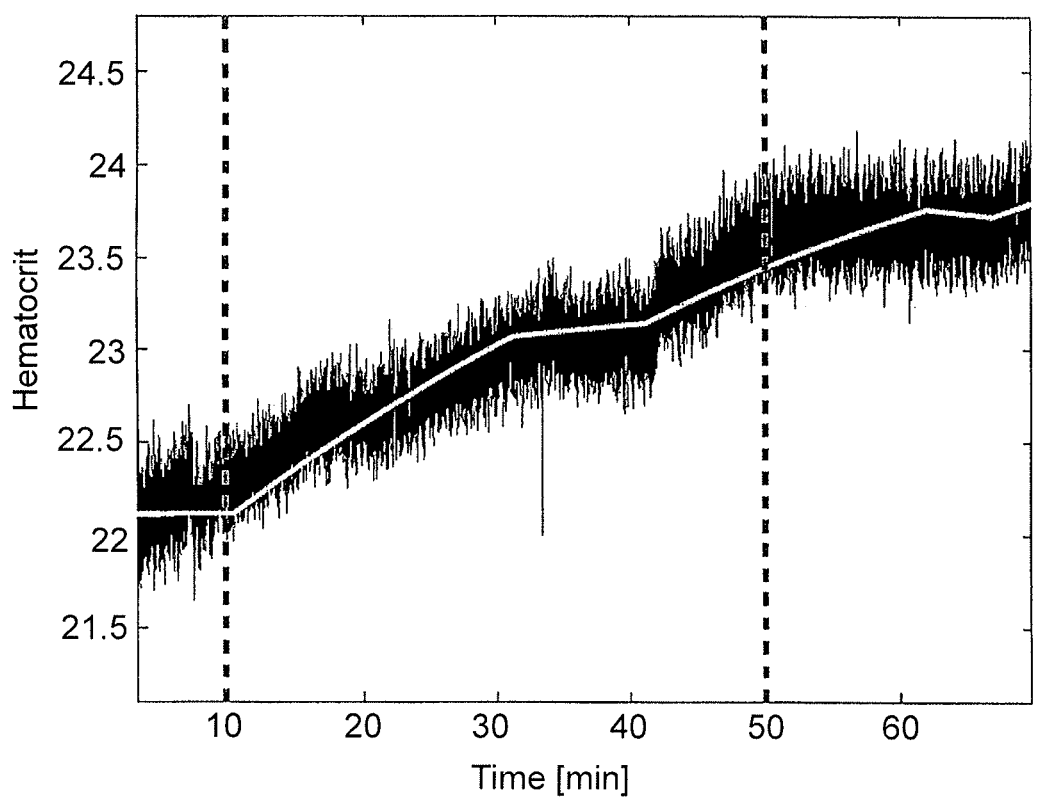
FIG. 12 is a graph illustrating an exemplary model output where the model is adapted to the hematocrit measurements of a specific patient (black curve) by identifying $L_p$ and $P_c$. The parameters were estimated within the two vertical dashed lines and hematocrit values were predicted for the following 20 minutes (white curve).

Parameter Estimation for Patient 1 Data:

FIG. 12 is a graph illustrating an exemplary model output where the model is adapted to the hematocrit measurements of a specific patient, patient "1" (black curve), by identifying $L_p$ and $P_c$. The parameters were estimated using measurements within the two vertical dashed lines and hematocrit values were predicted for the following 20 minutes (white curve). The white curve is the model output Eq. (14) obtained by solving the system of ordinary differential equations given in Eq. (12). The model has a good prediction for the next 20 minutes after the estimation. Hence, the model can predict the dynamics of vascular refilling for a short period of time.

Table 5 indicates that for this particular patient data set, $L_p$ and $P_c$ are identifiable. As shown, varied initial parameter values converge to the same estimated values (to some degree of accuracy). It indicates local identifiability of these model parameters.

TABLE 5

Identification of $(L_p, P_c)$.

| Initial Value | Estimated Value |
|---|---|
| (1.65, 21.1) | (2,8945, 20.4169) |
| (1.7325, 22.1550) | (2,8928, 20.4178) |
| (1.8150, 23.2100) | (2.8952, 20.4186) |
| (1.5675, 20.0450) | (2.8929, 20.4175) |
| (1.4850, 18.9900) | (2.8961, 20.4183) |
| (2.8, 20) | (2.8962, 20.4184) |
| (3.0800, 22) | (2.8930, 20.4176) |
| (2.5200, 18) | (2.8927, 20.4169) |

Figure 13:
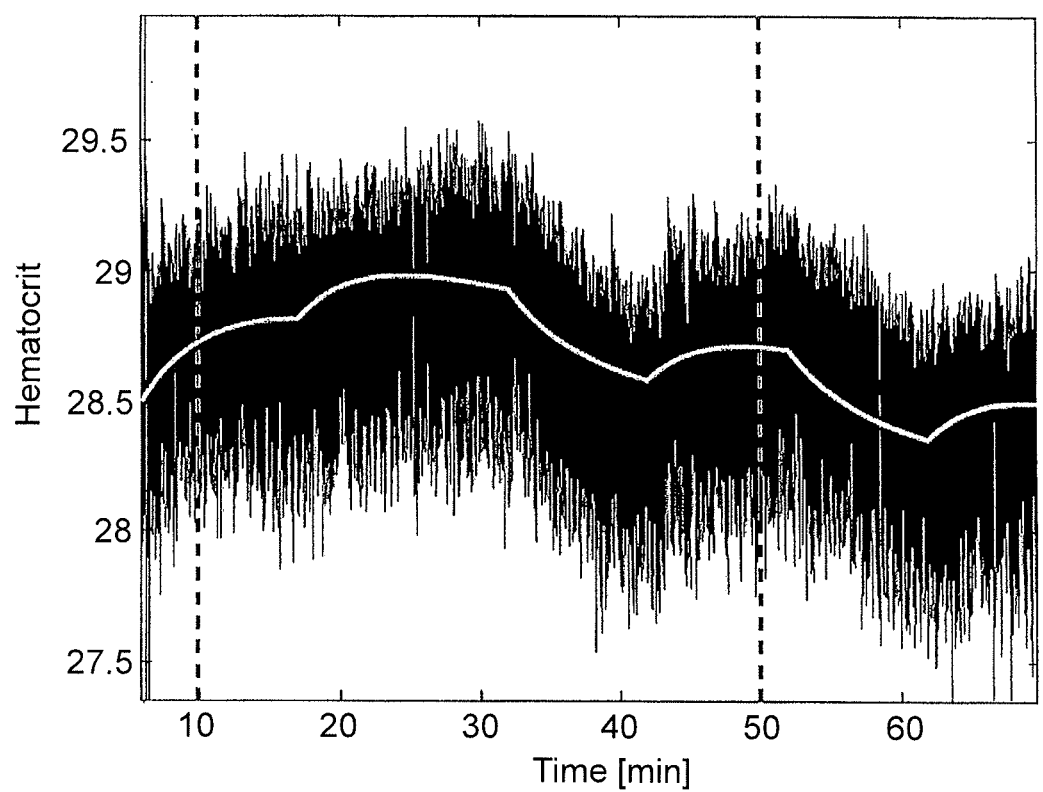
FIG. 13 is a graph illustrating an exemplary model output where the model is adapted to the hematocrit measurements of another specific patient (black curve) by identifying $L_p$ and $P_c$, and $\kappa$. The parameters were estimated within the two vertical dashed lines and hematocrit values were predicted for the following 20 minutes (white curve).

Parameter Estimation for Patient 2 Data:

Here, data of a different, second patient "2" is used to illustrate the validity of the model. In this case, three parameters, namely, $L_p$, $P_c$, and κ are estimated. FIG. 13 illustrates the second patient data and the corresponding parameter identification and model prediction. As in the previous illustration, the parameters of interest are identified from the data for t ∈ [10, 50]. It can be seen that the model with the estimated parameters provide a good prediction for the next 20 minutes.

Table 6 shows that different initial values of the parameters $L_p$, $P_c$, and κ converge to the same estimated values. Thus, it indicates local identifiability of these parameters.

TABLE 6

Identification of $(L_p, P_c, \kappa)$.

| Initial Value | Estimated Value |
|---|---|
| (30, 20, 10) | (30.3206, 21.2392, 10.3555) |
| (30.3, 21.2, 10.3) | (30.3435, 21.2389, 10.3529) |
| (31.8150, 22.26, 10.815) | (30.3178, 21.2395, 10.3590) |
| (33.3, 23.32, 11.33) | (30.3365, 21.2392, 10.3567) |
| (29.5425, 20.67, 10.0425) | (30.3095, 21.2393, 10.3553) |
| (27.27, 19.08, 9.27) | (30.3326, 21.2387, 10.3505) |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

APPENDIX

A Quadratic Approximation to Colloid Osmotic Pressures

The colloid osmotic pressure $\pi_p$, $\pi_i$ in plasma and in the interstitium can be expressed in terms of its respective protein concentrations $c_p$, $c_i$ as follows $$\pi_p = a_{p_1} c_p + a_{p_2} c_p^2 + a_{p_3} c_p^3, \quad c_p \geq 0,$$

$$\pi_i = a_{i_1} c_i + a_{i_2} c_i^1 + a_{i_3} c_i^3, \quad c_i \geq 0,$$

Figure 14:
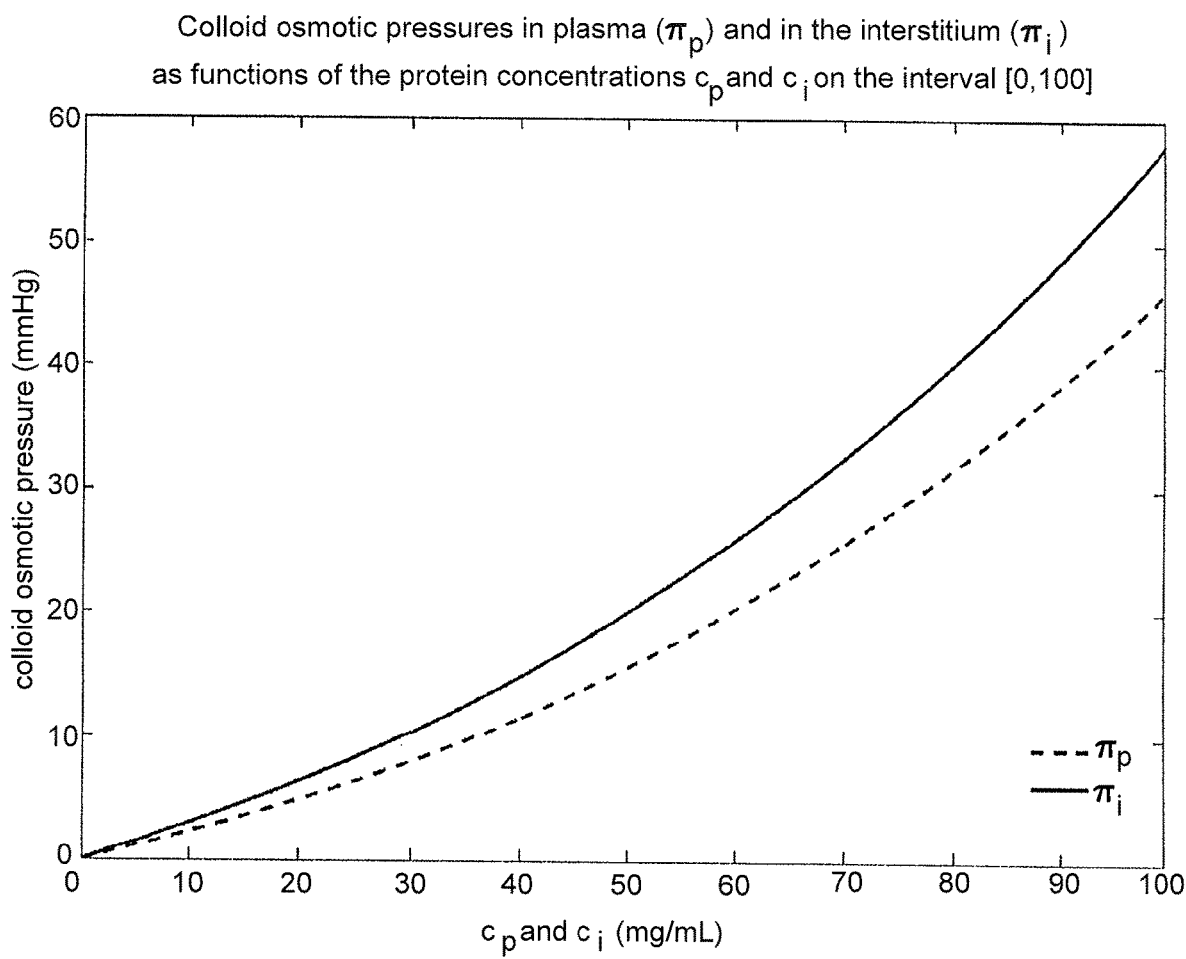
FIG. 14 illustrates plots of the functions $\pi_p$ and $\pi_i$ referenced in Appendix A.

The coefficients are given by $$a_{p_1} = 0.21, \; a_{p_2} = 0.0016, \; a_{p_3} = 0.000009,$$

$$a_{i_1} = 0.28, \; a_{i_2} = 0.0018, \; a_{i_3} = 0.000012,$$

the units being mmHg(mL/mg), mmHg(mL/mg)$^2$ and mmHg(mL/mg)$^3$. The plot for $\pi_p$ and $\pi_i$ shown in FIG. 14 for $0 \leq c_p$, $c_i \leq 100$ mg/mL indicates that quadratic polynomials instead of cubic polynomials would capture the relevant dynamics using fewer parameters.

The quadratic approximations $\pi_{p,approx}(c_p) = \alpha_1 c_p + \alpha_2 c_p^2$ and $\pi_{i,approx}(c_i) = \beta_1 c_i + \beta_2 c_i^2$ of $\pi_p(c_p)$ and $\pi_i(c_i)$ are computed by minimizing $$\|\pi_p(\cdot) - \pi_{p,approx}(\cdot)\|\mathcal{L}^1 = \sum_{j=0}^{1000} |\pi_p(0.1j) - \pi_{p,approx}(0.1j)|,$$

$$\|\pi_i(\cdot) - \pi_{i,approx}(\cdot)\|\mathcal{L}^1 = \sum_{j=0}^{1000} |\pi_i(0.1j) - \pi_{i,approx}(0.1j)|.$$

The obtained coefficients $\alpha_k$, $\beta_k$, $k=1, 2$, are given by $$\alpha_1 = 0.1752, \; \alpha_2 = 0.0028, \; \beta_1 = 0.2336, \; \beta_2 = 0.0034.$$

Figure 15:
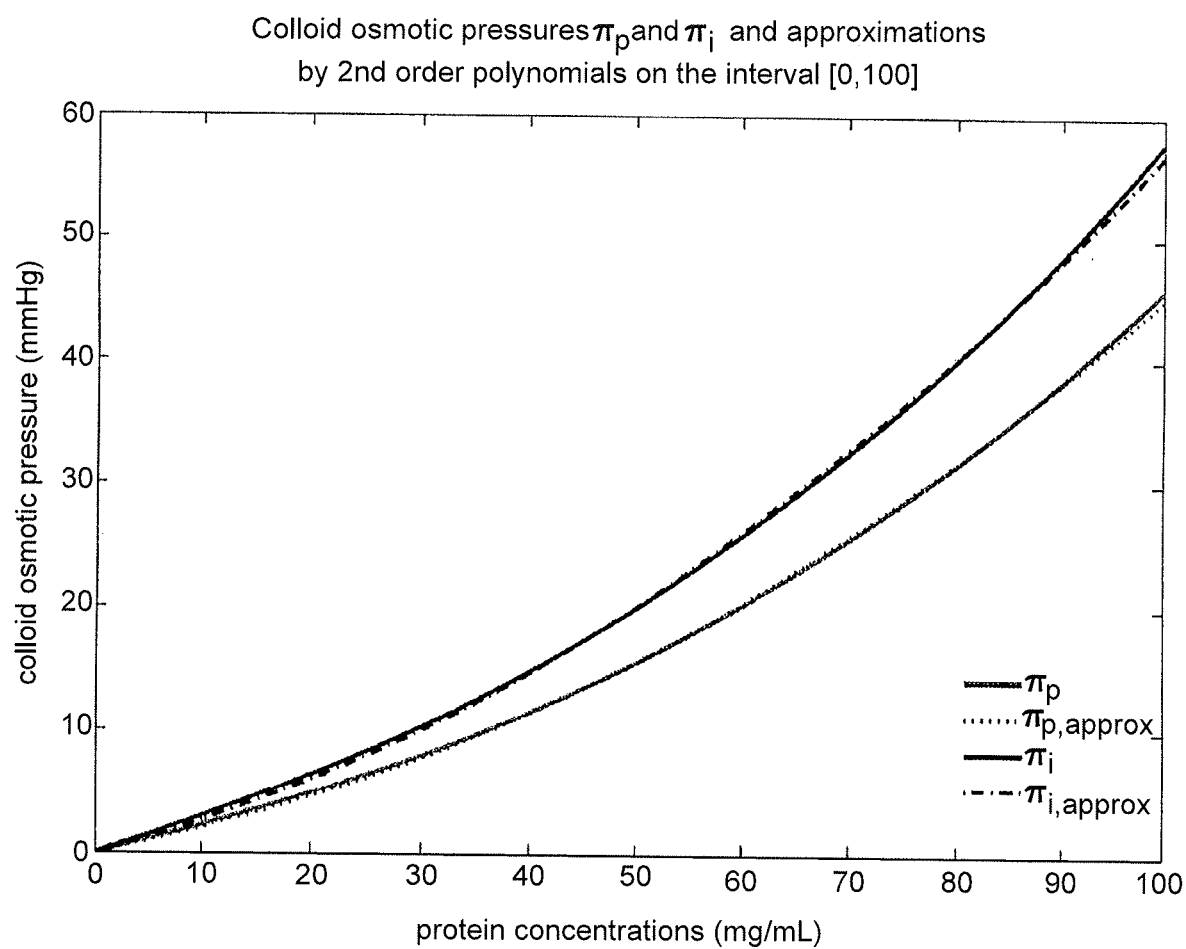
FIG. 15 illustrates graphs of $\pi_p$, $\pi_{p,approx}$, $\pi_i$ and $\pi_{i,approx}$ referenced in Appendix A.
Figure 16:
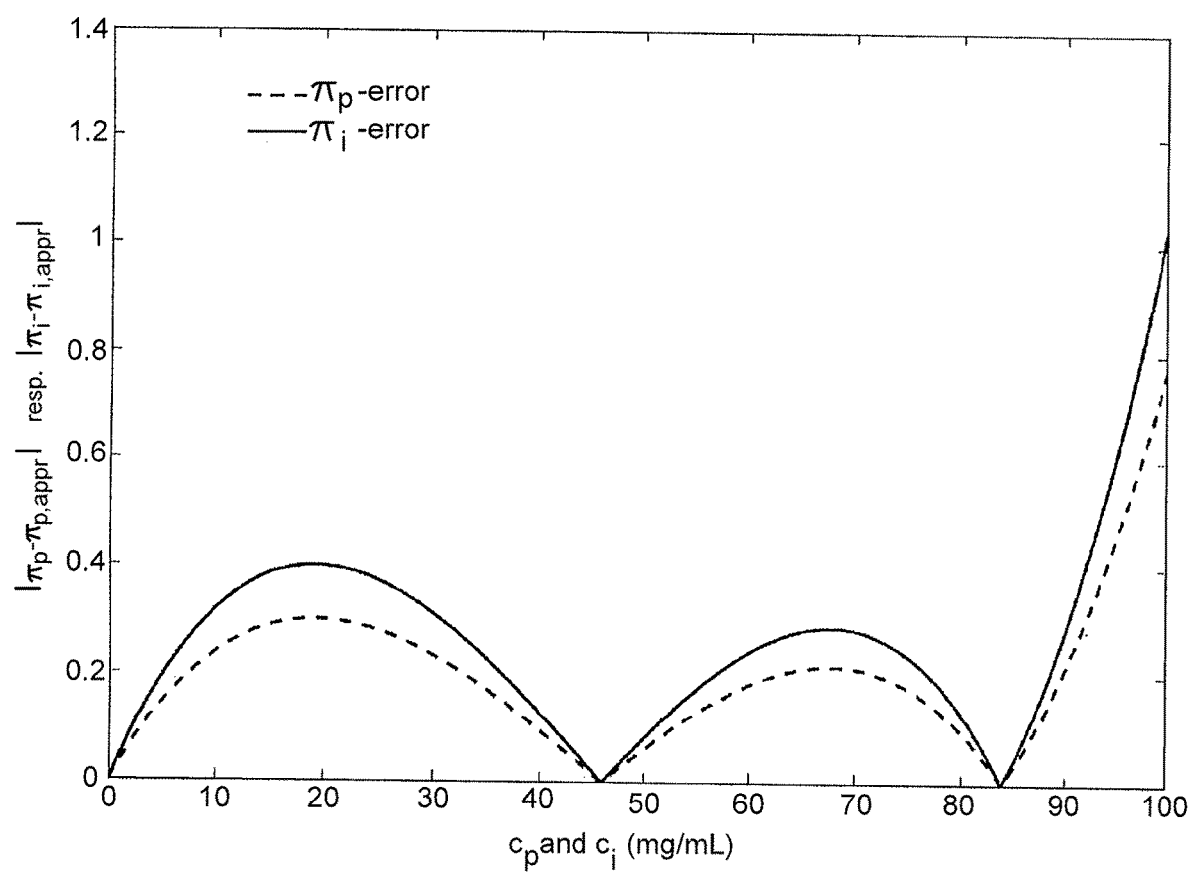
FIG. 16 illustrates errors for the quadratic approximation of $\pi_p$ and $\pi_i$ referenced in Appendix A.

In FIG. 15 we show the function $\pi_p$ and $\pi_i$ together with the approximating polynomials $\pi_{p,approx}$ and $\pi_{i,approx}$, whereas in FIG. 16 we present the differences $\pi_p - \pi_{p,approx}$ and $\pi_i - \pi_{i,approx}$. The maximal errors occur at $c_p = c_i = 100$ and are given by 0.7774 for $\pi_p$ and 1.0346 for $\pi_i$.

B Computation of Equilibria

Let the colloid osmotic pressures $\pi_p$, $\pi_i$ in the plasma and the interstitium be given as $$\pi_p = a_{p_1} c_p + a_{p_2} c_p^2, \quad c_p \geq 0,$$

$$\pi_i = a_{i_1} c_i + a_{i_2} c_i^2, \quad c_i \geq 0,$$

where $c_p$ respectively $c_i$ is the protein concentration in plasma respectively in the interstitium. Assume that the equilibrium $\pi_p^*$ value is known. The equilibrium $c_p^*$ can be computed by solving the quadratic equation $$a_{p_2}(c_p^*)^2 + a_{p_1} c_p^* - \pi_p^* = 0.$$

Using quadratic formula, the roots of the above equation are $$c_p^* = \frac{-a_{p_1} \pm \sqrt{a_{p_1}^2 + 4 a_{p_2} \pi_p^*}}{2 a_{p_2}}.$$

There exists a real root provided that the discriminant $a_{p_1}^2 + 4 a_{p_2} \pi_p^* > 0$. Hence, to ensure that $c_p^*$ is positive, the following equation has to be satisfied $$-a_{p_1} + \sqrt{a_{p_1}^2 + 4 a_{p_2} \pi_p^*} > 0,$$

which is trivially satisfied since $\pi_p^*$ is always positive.

Assuming all the parameters are known including the constant lymph flow to the plasma $\kappa$, the equilibrium interstitial colloid osmotic pressure $c_1^*$ can be obtained by solving the equilibria of our model. That is, we have $$J_v = -\kappa,$$

$$L_p(\sigma(\pi_p^* - \pi_i^*) - (P_c - P_i)) = -\kappa,$$

$$\pi_i^* = \pi_p^* - \frac{1}{\sigma}\left(-\frac{\kappa}{L_f p} + (P_c - P_i)\right).$$

Expressing the $\pi_i^*$ in terms of $c_i$ yields $$a_{i_1} c_i^* + a_{i_2}(c_i^*)^2 = \pi_p^* - \frac{1}{\sigma}\left(-\frac{\kappa}{L_p} + (P_c - P_i)\right).$$

As above, in order to obtain a real positive $c_i^*$, the following equation needs to be satisfied $$-a_{i_1} + \sqrt{a_{i_1}^2 + 4 a_{i_2}\left(\pi_p^* - \frac{1}{\sigma}\left(-\frac{\kappa}{L_p} + (P_c - P_i)\right)\right)} > 0.$$

The equilibrium value for $c_i$ is then given by $$c_i^* = \frac{-a_{i_1} + \sqrt{a_{i_1}^2 + 4 a_{i_2}\left(\pi_p^* - \frac{1}{\sigma}\left(-\frac{\kappa}{L_p} + (P_c - P_i)\right)\right)}}{2 a_{i_2}}.$$

C Sensitivities

C.1 Traditional Sensitivities

Let the variable $y=y(\theta)$ for $\theta \in D$, where D is some open interval and assume that y is differentiable on D. Let $\theta_0 \in D$ be given and assume that $\theta_0 \neq 0$ and $y_0 = y(\theta_0) \neq 0$. Here, $\theta_0$ denotes the initial/nominal parameter and $y_0$ refers to the initial model output. The sensitivity $s_y(\theta_0)$ of y with respect to $\theta$ at $\theta_0$ is defined as:

$$s_{y,\theta}(\theta_0) = \lim_{\Delta\theta \to 0} \frac{\Delta y / y_0}{\Delta / \theta_0} = \frac{\theta_0}{y_0} y'(\theta_0).$$

The sensitivities $s_{x,0}(\theta_0)$ are defined such that they are invariant against changes of units in both $\theta$ and y.

In general, we have a dynamical system of the form $$(AWP) \begin{cases} \dot{x}(t) = \mathcal{F}(t, x(t), \theta), \\ x(0) = x_0(\theta) \end{cases},$$

where x(t) is the vector of state variables of the system, $\theta$ is the vector of system parameters and $t \in [0, T]$. We define $$y(t) = f(t, \theta), \quad 0 \le t \le T,$$

to be the (single) output of the system.

In order to compute the traditional sensitivity functions (TSF) (sensitivity of a model output with respect to various parameters on which it depends) as well as for the generalized sensitivities (GSF) (sensitivity of parameter estimates with respect to measurements) the so called sensitivity equations are needed. The sensitivity equations are a linear ODE-system of the following form $$\dot{S}(t, \theta) = \mathcal{F}_x(t, x(t, \theta), \theta) S(t, \theta) + \mathcal{F}_\theta(t, x(t, \theta), \theta), \quad (17)$$

$$S(0, \theta) = \frac{\partial x_0(\theta)}{\partial \theta},$$

where $F_x(\bullet)$ and $F_\theta(\bullet)$ denote the partial derivative of F with respect to the state variable x and parameter $\theta$, respectively. Equation (17) in conjunction with (AWP) provides a fast and sufficient way to compute the sensitivity matrix $S(t, \theta)$ numerically.

C.2 Generalized Sensitivities

The generalized sensitivity function $g_s(t_l)$ with respect to the parameter $\theta_k$ at the time instant $t_l$ for $\theta$ in a neighborhood of $\theta_0$ (the initial/nominal parameter vector) is given by $$g_S(t_l) = \sum_{i=1}^{l} \frac{1}{\sigma^2(t_i)} (F^{-1} \nabla_\theta f(t_i, \theta)) \nabla_\theta f(t_i, \theta),$$

and the Fisher Information Matrix F is given by $$F = \sum_{j=1}^{N} \frac{1}{\sigma^2(t_j)} \nabla_\theta f(t_j, \theta) \nabla_\theta f(t_j, \theta)^T,$$

where $t_1, \ldots, t_N$ denotes the measurement points.

C.3 Subset Selection Algorithm

Given $p < p_0$, the algorithm taken from the literature considers all possible indices $i_1, \ldots, i_p$ with $1 \le i_1 < \ldots < i_p \le p_0$ in lexicographical ordering starting with the first choice $(i_1^{(1)}, \ldots, i_p^{(1)}) = (1, \ldots, p)$ and completes the following steps:

Initializing step: Set $\text{ind}^{sel} = (1, \ldots, p)$ and $\alpha^{sel} = \infty$.

Step k: For the choice $(i_1^{(k)}, \ldots, i_p^{(k)})$ compute r=rank F $((q_0)i_1^{(k)}, \ldots, (q_0)i_p^{(k)})$.

If r<p, go to Step k+1.

If r=p, compute $\alpha_k = ((q_0)i_1^{(k)}, \ldots, (q_0)i_p^{(k)})$.

If $\alpha_k \ge \alpha^{sel}$, go to Step k+1.

If $\alpha_k < \alpha$, set $\text{ind}^{sel} = (i_1^{(k)}, \ldots, i_p^{(k)})$, $\alpha^{sel} = \alpha_k$ and go to Step k+1.

F is the Fisher information matrix mentioned in the preceding section.

C.4 Sensitivity with Respect to a Parameter

It can be easily verified that the partial derivative of $J_v$ with respect to $c_p$ and $c_i$ are $$\frac{\partial J_v}{\partial c_p} = L_p \sigma (a_{p_1} + 2 a_{p_2} c_p), \quad (18)$$

$$\frac{\partial J_v}{\partial c_i} = -L_p \sigma (a_{i_1} + 2 a_{i_2} c_i),$$

respectively. Also, the following can be obtained immediately $$\frac{\partial}{\partial c_p}(e^x - 1) = e^x \frac{1-\sigma}{PS} \frac{\partial J_v}{\partial c_p}, \quad (19)$$

$$\frac{\partial}{\partial c_i}(e^x - 1) = e^x \frac{1-\sigma}{PS} \frac{\partial J_v}{\partial c_i}.$$

The partial derivative of $J_s$ with respect to $c_p$ when $J_v > 0$ can be derived as follows $$\frac{\partial J_s}{\partial c_p} = (1-\sigma) \left( \frac{\partial J_v}{\partial c_p} \left( c_i - \frac{c_p - c_i}{e^x - 1} \right) - \right.$$

$$\left. J_v \left( \frac{(e^x - 1) - (c_p - c_i) e^x \frac{1-\sigma}{PS} \frac{\partial J_v}{\partial c_p}}{(e^x - 1)^2} \right) \right)$$

$$= (1-\sigma) \left( \frac{\partial J_v}{\partial c_p} \left( c_i - \frac{c_p - c_i}{e^x - 1} \right) - \right.$$

$$\left. \left( \frac{J_v(e^x - 1) - (c_p - c_i) e^x \frac{J_v(1-\sigma)}{PS} \frac{\partial J_v}{\partial c_p}}{(e^x - 1)^2} \right) \right)$$

$$= (1-\sigma) \left( \frac{\partial J_v}{\partial c_p} \left( c_i - \frac{c_p - c_i}{e^x - 1} \right) - \right.$$

$$\left. \left( \frac{J_v(e^x - 1) - (c_p - c_i) x e^x \frac{\partial J_v}{\partial c_p}}{(e^x - 1)^2} \right) \right),$$

$$\frac{\partial J_s}{\partial c_p} = (1-\sigma) \left( \left( c_i - \frac{c_p - c_i}{e^x - 1} + \frac{(c_p - c_i) x e^x}{(e^x - 1)^2} \right) \frac{\partial J_v}{\partial c_p} - \frac{J_v}{e^x - 1} \right).$$

When $J_v<0$, we have $$\frac{\partial J_s}{\partial c_p} = (1-\sigma)\left(\frac{\partial J_v}{\partial c_p}\left(c_p - \frac{c_p-c_i}{e^x-1}\right) + \right.$$
$$\left. J_v\left(1 - \frac{(e^x-1)-(c_p-c_i)e^x\frac{1-\sigma}{PS}\frac{\partial J_v}{\partial c_p}}{(e^x-1)^2}\right)\right)$$

$$= (1-\sigma)\left(\frac{\partial J_v}{\partial c_p}\left(c_p - \frac{c_p-c_i}{e^x-1}\right) + \right.$$
$$\left. J_v - \frac{J_v(e^x-1)-(c_p-c_i)e^x\frac{J_v(1-\sigma)}{PS}\frac{\partial J_v}{\partial c_p}}{(e^x-1)^2}\right)$$

$$= (1-\sigma)\left(\frac{\partial J_v}{\partial c_p}\left(c_p - \frac{c_p-c_i}{e^x-1}\right) + \right.$$
$$\left. J_v - \frac{J_v(e^x-1)-(c_p-c_i)xe^x\frac{\partial J_v}{\partial c_p}}{(e^x-1)^2}\right)$$

$$= (1-\sigma)\left(\left(c_p - \frac{c_p-c_i}{e^x-1} + \frac{(c_p-c_i)xe^x}{(e^x-1)^2}\right)\frac{\partial J_v}{\partial c_p} + J_v - \frac{J_v}{e^x-1}\right),$$

$$\frac{\partial J_s}{\partial c_p} = (1-\sigma)\left(\left(c_p - \frac{c_p-c_i}{e^x-1} + \frac{(c_p-c_i)xe^x}{(e^x-1)^2}\right)\frac{\partial J_v}{\partial c_p} + J_v\left(1 - \frac{1}{e^x-1}\right)\right).$$

Hence $$\frac{\partial J_s}{\partial c_p} = \begin{cases} (1-\sigma)\left(\left(c_i - \frac{c_p-c_i}{e^x-1} + \frac{(c_p-c_i)xe^x}{(e^x-1)^2}\right)\frac{\partial J_v}{\partial c_p} - \frac{J_v}{e^x-1}\right) & \text{if } J_v > 0, \\ 0 & \text{if } J_v = 0, \\ (1-\sigma)\left(\left(c_p - \frac{c_p-c_i}{e^x-1} + \frac{(c_p-c_i)xe^x}{(e^x-1)^2}\right)\frac{\partial J_v}{\partial c_p} + J_v\left(1 - \frac{1}{e^x-1}\right)\right) & \text{if } J_v < 0. \end{cases} \quad (20)$$

Assuming $J_v>0$, the partial derivative of $J_s$ with respect to $c_i$ is $$\frac{\partial J_s}{\partial c_i} = (1-\sigma)\left(\frac{\partial J_v}{\partial c_i}\left(c_i - \frac{c_p-c_i}{e^x-1}\right) + \right.$$
$$\left. J_v\left(1 - \frac{(e^x-1)-(c_p-c_i)e^x\frac{1-\sigma}{PS}\frac{\partial J_v}{\partial c_i}}{(e^x-1)^2}\right)\right)$$

$$= (1-\sigma)\left(\frac{\partial J_v}{\partial c_i}\left(c_i - \frac{c_p-c_i}{e^x-1}\right) + \right.$$
$$\left. J_v + \frac{J_v(e^x-1)+(c_p-c_i)e^x\frac{J_v(1-\sigma)}{PS}\frac{\partial J_v}{\partial c_i}}{(e^x-1)^2}\right)$$

$$= (1-\sigma)\left(\frac{\partial J_v}{\partial c_i}\left(c_i - \frac{c_p-c_i}{e^x-1}\right) + \right.$$
$$\left. J_v + \frac{J_v(e^x-1)+(c_p-c_i)xe^x\frac{\partial J_v}{\partial c_i}}{(e^x-1)^2}\right)$$

$$= (1-\sigma)\left(\left(c_i - \frac{c_p-c_i}{e^x-1} + \frac{(c_p-c_i)xe^x}{(e^x-1)^2}\right)\frac{\partial J_v}{\partial c_i} + J_v + \frac{J_v}{e^x-1}\right),$$

$$\frac{\partial J_s}{\partial c_i} = (1-\sigma)\left(\left(c_i - \frac{c_p-c_i}{e^x-1} + \frac{(c_p-c_i)xe^x}{(e^x-1)^2}\right)\frac{\partial J_v}{\partial c_i} + J_v\left(1 + \frac{1}{e^x-1}\right)\right).$$

When $J_v<0$, we obtain $$\frac{\partial J_s}{\partial c_i} = (1-\sigma)\left(\frac{\partial J_v}{\partial c_i}\left(c_p - \frac{c_p-c_i}{e^x-1}\right) + J_v\left(1 - \frac{(e^x-1)(-1) - (c_p-c_i)e^x\frac{1-\sigma}{PS}\frac{\partial J_v}{\partial c_i}}{(e^x-1)^2}\right)\right)$$

$$= (1-\sigma)\left(\frac{\partial J_v}{\partial c_i}\left(c_p - \frac{c_p-c_i}{e^x-1}\right) + \frac{J_v(e^x-1)+(c_p-c_i)e^x\frac{J_v(1-\sigma)}{PS}\frac{\partial J_v}{\partial c_i}}{(e^x-1)^2}\right)$$

$$= (1-\sigma)\left(\frac{\partial J_v}{\partial c_i}\left(c_p - \frac{c_p-c_i}{e^x-1}\right) + \frac{J_v(e^x-1)+(c_p-c_i)xe^x\frac{\partial J_v}{\partial c_i}}{(e^x-1)^2}\right),$$

$$\frac{\partial J_s}{\partial c_i} = (1-\sigma)\left(\left(c_p - \frac{c_p-c_i}{e^x-1} + \frac{(c_p-c_i)xe^x}{(e^x-1)^2}\right)\frac{\partial J_v}{\partial c_i} + \frac{J_v}{e^x-1}\right).$$

Therefore, $$\frac{\partial J_s}{\partial c_i} = \begin{cases} (1-\sigma)\left(\left(c_i - \frac{c_p-c_i}{e^x-1} + \frac{(c_p-c_i)xe^x}{(e^x-1)^2}\right)\frac{\partial J_v}{\partial c_i} + J_v\left(1 + \frac{1}{e^x-1}\right)\right) & \text{if } J_v > 0, \\ 0 & \text{if } J_v = 0, \\ (1-\sigma)\left(\left(c_p - \frac{c_p-c_i}{e^x-1} + \frac{(c_p-c_i)xe^x}{(e^x-1)^2}\right)\frac{\partial J_v}{\partial c_i} + \frac{J_v}{e^x-1}\right) & \text{if } J_v < 0. \end{cases} \quad (21)$$

Let F be a column vector whose entries are the right-hand side of our capillary model, that is, $$F = \begin{pmatrix} F_1 \\ F_2 \\ F_3 \\ F_4 \end{pmatrix} = \begin{pmatrix} J_v + \kappa - J_{UF} \\ \dfrac{J_s - c_p(J_v + \kappa - J_{UF})}{V_p} \\ -J_v - \kappa \\ \dfrac{-J_s + c_i(J_v + \kappa)}{V_i} \end{pmatrix}, \quad (22)$$

then the Jacobian of F is given by $$Jac_F = \begin{pmatrix} \dfrac{\partial F_1}{\partial V_p} & \dfrac{\partial F_1}{\partial c_p} & \dfrac{\partial F_1}{\partial V_i} & \dfrac{\partial F_1}{\partial c_i} \\ \dfrac{\partial F_2}{\partial V_p} & \dfrac{\partial F_2}{\partial c_p} & \dfrac{\partial F_2}{\partial V_i} & \dfrac{\partial F_2}{\partial c_i} \\ \dfrac{\partial F_3}{\partial V_p} & \dfrac{\partial F_3}{\partial c_p} & \dfrac{\partial F_3}{\partial V_i} & \dfrac{\partial F_3}{\partial c_i} \\ \dfrac{\partial F_4}{\partial V_p} & \dfrac{\partial F_4}{\partial c_p} & \dfrac{\partial F_4}{\partial V_i} & \dfrac{\partial F_4}{\partial c_i} \end{pmatrix}, \quad (23)$$

where $$\frac{\partial F_1}{\partial V_p} = 0, \frac{\partial F_1}{\partial c_p} = \frac{\partial J_v}{\partial c_p}, \frac{\partial F_1}{\partial V_i} = 0, \frac{\partial F_1}{\partial c_i} = \frac{\partial J_v}{\partial c_i},$$

$$\frac{\partial F_2}{\partial V_p} = -\frac{1}{V_p^2}(J_s - c_p(J_v + \kappa - J_{UF})),$$

$$\frac{\partial F_2}{\partial c_p} = \frac{1}{V_p}\left(\frac{\partial J_s}{\partial c_p} - c_p \frac{\partial J_v}{\partial c_p} - (J_v + \kappa - J_{UF})\right),$$

$$\frac{\partial F_2}{\partial V_i} = 0, \frac{\partial F_2}{\partial c_i} = \frac{1}{V_p}\left(\frac{\partial J_s}{\partial c_i} - c_p \frac{\partial J_v}{\partial c_i}\right), \frac{\partial F_3}{\partial V_p} = 0,$$

$$\frac{\partial F_3}{\partial c_p} = -\frac{\partial J_v}{\partial c_p}, \frac{\partial F_3}{\partial V_i} = 0, \frac{\partial F_3}{\partial c_i} = -\frac{\partial J_v}{\partial c_i}, \frac{\partial F_4}{\partial V_p} = 0,$$

$$\frac{\partial F_4}{\partial c_p} = \frac{1}{V_i}\left(-\frac{\partial J_s}{\partial c_p} + c_i \frac{\partial J_v}{\partial c_p}\right), \frac{\partial F_4}{\partial V_i} = -\frac{1}{V_i^2}(-J_s + c_i(J_v + \kappa)),$$

$$\frac{\partial F_4}{\partial c_i} = \frac{1}{V_i}\left(-\frac{\partial J_s}{\partial c_i} + c_i \frac{\partial J_v}{\partial c_i} + (J_v + \kappa)\right).$$

If we set $u = (V_p, C_p, V_i, c_i)^T$ and $\theta = (L_p, \sigma, PS, P_c, P_i, a_{p_1}, a_{p_2}, a_{i_1}, a_{i_2}, \kappa, \alpha, J_{UF})$, the sensitivity equations with respect to a certain parameter $\theta_i$ (assuming continuity conditions are satisfied) can be written as $$\frac{d}{dt}\frac{\partial u}{\partial \theta_i} = \frac{\partial F}{\partial u}\frac{\partial u}{\partial \theta_i} + \frac{\partial F}{\partial \theta_i} = Jac_F \frac{\partial u}{\partial \theta_i} + \frac{\partial F}{\partial \theta_i}. \quad (24)$$

Sensitivity with Respect to $L_p$

To derive the sensitivity with respect to $L_p$, we need $$\frac{\partial J_v}{\partial L_p} = \sigma(\pi_p - \pi_i) - (P_c - P_i). \quad (25)$$

It clearly follows that $$\frac{\partial}{\partial L_p}(e^x - 1) = e^x \frac{1-\sigma}{PS}\frac{\partial J_v}{\partial L_p}. \quad (26)$$

For $J_v > 0$, the partial derivative of $J_s$ with respect to $L_p$ is derived as $$\frac{\partial J_s}{\partial L_p} = (1-\sigma)\left(\frac{\partial J_v}{\partial L_p}\left(c_i - \frac{c_p - c_i}{e^x - 1}\right) + J_v\left(\frac{(c_p - c_i)e^x \frac{1-\sigma}{PS}\frac{\partial J_v}{\partial L_p}}{(e^x - 1)^2}\right)\right)$$

$$= (1-\sigma)\left(\left(c_i - \frac{c_p - c_i}{e^x - 1}\right) + \frac{J_v(1-\sigma)}{PS}\left(\frac{(c_p - c_i)e^x}{(e^x - 1)^2}\right)\right)\frac{\partial J_v}{\partial L_p},$$

$$\frac{\partial_s}{\partial L_p} = (1-\sigma)\left(c_i - \frac{c_p - c_i}{e^x - 1} + \frac{(c_p - c_i)xe^x}{(e^x - 1)^2}\right)\left(\frac{\partial J_v}{\partial L_p}\right).$$

Similar computation applies for $J_v < 0$ and therefore we obtain $$\frac{\partial J_s}{\partial L_p} = \begin{cases} (1-\sigma)\left(c_i - \dfrac{c_p - c_i}{e^x - 1} + \dfrac{(c_p - c_i)xe^x}{(e^x - 1)^2}\right)\dfrac{\partial J_v}{\partial L_p} & \text{if } J_v > 0, \\ 0 & \text{if } J_v = 0, \\ (1-\sigma)\left(c_p - \dfrac{c_p - c_i}{e^x - 1} + \dfrac{(c_p - c_i)xe^x}{(e^x - 1)^2}\right)\dfrac{\partial J_v}{\partial L_p} & \text{if } J_v < 0. \end{cases} \quad (27)$$

Now, the sensitivity equations with respect to $L_p$ are $$\frac{d}{dt}\begin{pmatrix} \dfrac{\partial V_p}{\partial L_p} \\ \dfrac{\partial c_p}{\partial L_p} \\ \dfrac{\partial V_i}{\partial L_p} \\ \dfrac{\partial c_i}{\partial L_p} \end{pmatrix} = Jac_F \begin{pmatrix} \dfrac{\partial V_p}{\partial L_p} \\ \dfrac{\partial c_p}{\partial L_p} \\ \dfrac{\partial V_i}{\partial L_p} \\ \dfrac{\partial c_i}{\partial L_p} \end{pmatrix} + \begin{pmatrix} \dfrac{\partial F_1}{\partial L_p} \\ \dfrac{\partial F_2}{\partial L_p} \\ \dfrac{\partial F_3}{\partial L_p} \\ \dfrac{\partial F_4}{\partial L_p} \end{pmatrix}$$

and so $$\frac{d}{dt}\left(\frac{\partial V_p}{\partial L_p}\right) = \frac{\partial}{\partial L_p}\left(\frac{\partial V_p}{\partial dt}\right)$$

$$= \frac{\partial}{\partial V_p}(J_v + \kappa - J_{UF})\frac{\partial V_p}{\partial L_p} + \frac{\partial}{\partial c_p}(J_v + \kappa - J_{UF})\frac{\partial c_p}{\partial L_p} +$$

$$\frac{\partial}{\partial V_i}(J_v + \kappa - J_{UF})\frac{\partial V_i}{\partial L_p} + \frac{\partial}{\partial c_i}(J_v + \kappa - J_{UF})\frac{\partial c_i}{\partial L_p} +$$

$$\frac{\partial}{\partial L_p}(J_v + \kappa - J_{UF})$$

$$= \frac{\partial J_v}{\partial c_p}\frac{\partial c_p}{\partial L_p} + \frac{\partial J_v}{\partial c_i}\frac{\partial c_i}{\partial L_p} + \frac{\partial J_v}{\partial L_p},$$

$$\frac{d}{dt}\left(\frac{\partial c_p}{\partial L_p}\right) = \frac{\partial}{\partial L_p}\left(\frac{dc_p}{dt}\right)$$

$$= \frac{\partial}{\partial V_p}\left(\frac{J_s - c_p(J_v + \kappa - J_{UF})}{V_p}\right)\frac{\partial V_p}{\partial L_p} +$$

$$\frac{\partial}{\partial c_p}\left(\frac{J_s - c_p(J_v + \kappa - J_{UF})}{V_p}\right)\frac{\partial c_p}{\partial L_p} +$$

$$\frac{\partial}{\partial V_i}\left(\frac{J_s - c_p(J_v + \kappa - J_{UF})}{V_p}\right)\frac{\partial V_i}{\partial L_p} +$$

$$\frac{\partial}{\partial c_i}\left(\frac{J_s - c_p(J_v + \kappa - J_{UF})}{V_p}\right)\frac{\partial c_i}{\partial L_p} + \frac{\partial}{\partial L_p}\left(\frac{J_s - c_p(J_v + \kappa - J_{UF})}{V_p}\right)$$

$$= -\left(\frac{J_s - c_p(J_v + \kappa - J_{UF})}{V_p^2}\right)\frac{\partial V_p}{\partial L_p} +$$

$$\frac{1}{V_p}\left(\frac{\partial J_s}{\partial c_p} - c_p \frac{\partial J_v}{\partial c_p} - (J_v + \kappa - J_{UF})\right)\frac{\partial c_p}{\partial L_p} +$$

$$\frac{1}{V_p}\left(\frac{\partial J_s}{\partial c_i} - c_p \frac{\partial J_v}{\partial c_i}\right)\frac{\partial c_i}{\partial L_p} + \frac{1}{V_p}\left(\frac{\partial J_s}{\partial L_p} - c_p \frac{\partial J_v}{\partial L_p}\right),$$

-continued $$\frac{d}{dt}\left(\frac{\partial V_i}{\partial L_p}\right) = \frac{\partial}{\partial L_p}\left(\frac{dV_i}{dt}\right)$$

$$= +\frac{\partial}{\partial V_p}(-J_v - \kappa)\frac{\partial V_p}{\partial L_p} + \frac{\partial}{\partial c_p}(-J_v - \kappa)\frac{\partial c_p}{\partial L_p} +$$

$$\frac{\partial}{\partial V_i}(-J_v - \kappa)\frac{\partial V_i}{\partial L_p} + \frac{\partial}{\partial c_i}(-J_v - \kappa)\frac{\partial c_i}{\partial L_p} + \frac{\partial}{\partial L_p}(-J_v - \kappa)$$

$$= -\frac{\partial J_v}{\partial c_p}\frac{\partial c_p}{\partial L_p} - \frac{\partial J_v}{\partial c_i}\frac{\partial c_i}{\partial L_p} - \frac{\partial J_v}{\partial L_p},$$

$$\frac{d}{dt}\left(\frac{\partial c_i}{\partial L_p}\right) = \frac{\partial}{\partial L_p}\left(\frac{dc_i}{dt}\right)$$

$$= \frac{\partial}{\partial V_p}\left(\frac{-J_s + c_i(J_v + \kappa)}{V_i}\right)\frac{\partial V_p}{\partial L_p} + \frac{\partial}{\partial c_p}\left(\frac{-J_s + c_i(J_v + \kappa)}{V_i}\right)\frac{\partial c_p}{\partial L_p} +$$

$$\frac{\partial}{\partial V_i}\left(\frac{-J_s + c_i(J_v + \kappa)}{V_i}\right)\frac{\partial V_i}{\partial L_p} + \frac{\partial}{\partial c_i}\left(\frac{-J_s + c_i(J_v + \kappa)}{V_i}\right)\frac{\partial c_i}{\partial L_p} +$$

$$\frac{\partial}{\partial L_p}\left(\frac{-J_s + c_i(J_v + \kappa)}{V_i}\right)$$

$$= \frac{1}{V_i}\left(-\frac{\partial J_s}{\partial c_p} + c_i\frac{\partial J_v}{\partial c_p}\right)\frac{\partial c_p}{\partial L_p} - \left(\frac{-J_s + c_i(J_v + \kappa)}{V_i^2}\right)\frac{\partial V_i}{\partial L_p} +$$

$$\frac{1}{V_i}\left(-\frac{\partial J_s}{\partial c_i} + c_i\frac{\partial J_v}{\partial c_i} + (J_v + \kappa)\right)\frac{\partial c_i}{\partial L_p} + \frac{1}{V_i}\left(-\frac{\partial J_s}{\partial L_p} + c_i\frac{\partial J_v}{\partial L_p}\right).$$

Sensitivity with Respect to σ

One can easily obtain $$\frac{\partial J_v}{\partial \sigma} = L_p(\pi_p - \pi_i). \quad (28)$$

With $$x = \frac{J_v(1 - \sigma)}{PS},$$

it follows that $$\frac{\partial}{\partial \sigma}(e^x - 1) = e^x\left(\frac{(1 - \sigma)}{PS}\frac{\partial J_v}{\partial \sigma} - \frac{J_v}{PS}\right). \quad (29)$$

For $J_v > 0$, the partial derivative of $J_s$ with respect to σ can be obtained as follows $$\frac{\partial J}{\partial \sigma} = \frac{\partial J_v}{\partial \sigma}(1 - \sigma)\left(c_i - \frac{c_p - c_i}{e^x - 1}\right) - J_v\left(c_i - \frac{c_p - c_i}{e^x - 1}\right) +$$

$$J_v(1-\sigma)\left(\frac{(c_p - c_i)e^x\left(\frac{(1-\sigma)}{PS}\frac{\partial J_v}{\partial \sigma} - \frac{J_v}{PS}\right)}{(e^x - 1)^2}\right)$$

$$= \frac{\partial J_v}{\partial \sigma}(1 - \sigma)\left(c_i - \frac{c_p - c_i}{e^x - 1}\right) - J_v\left(c_i - \frac{c_p - c_i}{e^x - 1}\right) +$$

$$\frac{J_v(1-\sigma)}{PS}\left(\frac{(c_p - c_i)e^x\left((1-\sigma)\frac{\partial J_v}{\partial \sigma} - J_v\right)}{(e^x - 1)^2}\right)$$

$$= \frac{\partial J_v}{\partial \sigma}(1 - \sigma)\left(c_i - \frac{c_p - c_i}{e^x - 1}\right) - J_v\left(c_i - \frac{c_p - c_i}{e^x - 1}\right) +$$

$$x\left(\frac{(c_p - c_i)e^x\left((1-\sigma)\frac{\partial J_v}{\partial \sigma} - J_v\right)}{(e^x - 1)^2}\right)$$

$$= \left((1-\sigma)\left(c_i - \frac{c_p - c_i}{e^x - 1}\right) + \frac{(c_p - c_i)(1-\sigma)xe^x}{(e^x - 1)^2}\right)\frac{\partial J_v}{\partial \sigma} -$$

$$J_v\left(c_i - \frac{c_p - c_i}{e^x - 1}\right) - J_v\left(\frac{(c_p - c_i)xe^x}{(e^x - 1)^2}\right),$$

$$\frac{\partial J_s}{\partial \sigma} = (1-\sigma)\left(c_i - \frac{c_p - c_i}{e^x - 1} + \frac{(c_p - c_i)xe^x}{(e^x - 1)^2}\right)\frac{\partial J_v}{\partial \sigma} -$$

$$J_v\left(c_i - \frac{c_p - c_i}{e^x - 1} + \frac{(c_p - c_i)xe^x}{(e^x - 1)^2}\right).$$

Slight modifications can be obtained when $J_v < 0$. Hence, we have $$\frac{\partial J_s}{\partial \sigma} = \begin{cases} (1-\sigma)\left(c_i - \frac{c_p - c_i}{e^x - 1} + \frac{(c_p - c_i)xe^x}{(e^x - 1)^2}\right)\frac{\partial J_v}{\partial \sigma} - \\ \qquad J_v\left(c_i - \frac{c_p - c_i}{e^x - 1} + \frac{(c_p - c_i)xe^x}{(e^x - 1)^2}\right) & \text{if } J_v > 0, \\ 0 & \text{if } J_v = 0, \\ (1-\sigma)\left(c_p - \frac{c_p - c_i}{e^x - 1} + \frac{(c_p - c_i)xe^x}{(e^x - 1)^2}\right)\frac{\partial J_v}{\partial \sigma} - \\ \qquad J_v\left(c_p - \frac{c_p - c_i}{e^x - 1} + \frac{(c_p - c_i)xe^x}{(e^x - 1)^2}\right) & \text{if } J_v < 0. \end{cases} \quad (30)$$

The sensitivity equations with respect to σ can be obtained as follows $$\frac{d}{dt}\begin{pmatrix} \frac{\partial V_p}{\partial \sigma} \\ \frac{\partial c_p}{\partial \sigma} \\ \frac{\partial V_i}{\partial \sigma} \\ \frac{\partial c_i}{\partial \sigma} \end{pmatrix} = Jac_F \begin{pmatrix} \frac{\partial V_p}{\partial \sigma} \\ \frac{\partial c_p}{\partial \sigma} \\ \frac{\partial V_i}{\partial \sigma} \\ \frac{\partial c_i}{\partial \sigma} \end{pmatrix} + \begin{pmatrix} \frac{\partial F_1}{\partial \sigma} \\ \frac{\partial F_2}{\partial \sigma} \\ \frac{\partial F_3}{\partial \sigma} \\ \frac{\partial F_4}{\partial \sigma} \end{pmatrix}$$

and so $$\frac{d}{dt}\left(\frac{\partial V_p}{\partial \sigma}\right) = \frac{\partial}{\partial \sigma}\left(\frac{dV_p}{dt}\right)$$

$$= \frac{\partial}{\partial V_p}(J_v + \kappa - J_{UF})\frac{\partial V_p}{\partial \sigma} + \frac{\partial}{\partial c_p}(J_v + \kappa - J_{UF})\frac{\partial c_p}{\partial \sigma} +$$

$$\frac{\partial}{\partial V_i}(J_v + \kappa - J_{UF})\frac{\partial V_i}{\partial \sigma} + \frac{\partial}{\partial c_i}(J_v + \kappa - J_{UF})\frac{\partial c_i}{\partial \sigma} +$$

$$\frac{\partial}{\partial \sigma}(J_v + \kappa - J_{UF})$$

$$= \frac{\partial J_v}{\partial c_p}\frac{\partial c_p}{\partial \sigma} + \frac{\partial J_v}{\partial c_i}\frac{\partial c_i}{\partial \sigma} + \frac{\partial J_v}{\partial \sigma},$$

-continued $$\frac{d}{dt}\left(\frac{\partial c_p}{\partial \sigma}\right) = \frac{\partial}{\partial \sigma}\left(\frac{dc_p}{dt}\right)$$

$$= \frac{\partial}{\partial V_p}\left(\frac{J_s - c_p(J_v + \kappa - J_{UF})}{V_p}\right)\frac{\partial V_p}{\partial \sigma} +$$

$$\frac{\partial}{\partial c_p}\left(\frac{J_s - c_p(J_v + \kappa - J_{UF})}{V_p}\right)\frac{\partial c_p}{\partial \sigma} +$$

$$\frac{\partial}{\partial V_i}\left(\frac{J_s - c_p(J_v + \kappa - J_{UF})}{V_p}\right)\frac{\partial V_i}{\partial \sigma} +$$

$$\frac{\partial}{\partial c_i}\left(\frac{J_s - c_p(J_v + \kappa - J_{UF})}{V_p}\right)\frac{\partial c_i}{\partial \sigma} + \frac{\partial}{\partial \sigma}\left(\frac{J_s - c_p(J_v + \kappa - J_{UF})}{V_p}\right)$$

$$= -\left(\frac{J_s - c_p(J_v + \kappa - J_{UF})}{V_p^2}\right)\frac{\partial V_p}{\partial \sigma} +$$

$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial \sigma} +$$

$$\frac{1}{V_p}\left(\frac{\partial J_s}{\partial c_i} - c_p\frac{\partial J_v}{\partial c_i}\right)\frac{\partial c_i}{\partial \sigma} + \frac{1}{V_p}\left(\frac{\partial J_s}{\partial \sigma} - c_p\frac{\partial J_v}{\partial \sigma}\right),$$

$$\frac{d}{dt}\left(\frac{\partial V_i}{\partial \sigma}\right) = \frac{\partial}{\partial \sigma}\left(\frac{dV_i}{dt}\right)$$

$$= \frac{\partial}{\partial V_p}(-J_v - \kappa)\frac{\partial V_p}{\partial \sigma} + \frac{\partial}{\partial c_p}(-J_v - \kappa)\frac{\partial c_p}{\partial \sigma} +$$

$$\frac{\partial}{\partial V_i}(-J_v - \kappa)\frac{\partial V_i}{\partial \sigma} + \frac{\partial}{\partial c_i}(-J_v - \kappa)\frac{\partial c_i}{\partial \sigma} + \frac{\partial}{\partial \sigma}(-J_v - \kappa)$$

$$= -\frac{\partial J_v}{\partial c_p}\frac{\partial c_p}{\partial \sigma} - \frac{\partial J_v}{\partial c_i}\frac{\partial c_i}{\partial \sigma} - \frac{\partial J_v}{\partial \sigma},$$

$$\frac{d}{dt}\left(\frac{\partial c_i}{\partial \sigma}\right) = \frac{\partial}{\partial \sigma}\left(\frac{dc_i}{dt}\right)$$

$$= \frac{\partial}{\partial V_p}\left(\frac{-J_s + c_i(J_v + \kappa)}{V_i}\right)\frac{\partial V_p}{\partial \sigma} + \frac{\partial}{\partial c_p}\left(\frac{-J_s + c_i(J_v + \kappa)}{V_i}\right)\frac{\partial c_p}{\partial \sigma} +$$

$$\frac{\partial}{\partial V_i}\left(\frac{-J_s + c_i(J_v + \kappa)}{V_i}\right)\frac{\partial V_i}{\partial \sigma} + \frac{\partial}{\partial c_i}\left(\frac{-J_s + c_i(J_v + \kappa)}{V_i}\right)\frac{\partial c_i}{\partial \sigma} +$$

$$\frac{\partial}{\partial \sigma}\left(\frac{-J_s + c_i(J_v + \kappa)}{V_i}\right)$$

$$= \frac{1}{V_i}\left(-\frac{\partial J_s}{\partial c_p} + c_i\frac{\partial J_v}{\partial c_p}\right)\frac{\partial c_p}{\partial \sigma} - \left(\frac{-J_s + c_i(J_v + \kappa)}{V_i^2}\right)\frac{\partial V_i}{\partial \sigma} +$$

$$\frac{1}{V_i}\left(-\frac{\partial J_s}{\partial c_i} + c_i\frac{\partial J_v}{\partial c_i} + (J_v + \kappa)\right)\frac{\partial c_i}{\partial \sigma} + \frac{1}{V_i}\left(-\frac{\partial J_s}{\partial \sigma} + c_i\frac{\partial J_v}{\partial \sigma}\right).$$

Sensitivity with Respect to PS

Note that $$\frac{\partial J_v}{\partial (PS)} = 0. \tag{31}$$

With $$x = \frac{J_v(1-\sigma)}{PS},$$

it follows that $$\frac{\partial}{\partial (PS)}(e^x - 1) = -e^x\left(\frac{J_v(1-\sigma)}{(PS)^2}\right) = \frac{-xe^x}{PS}. \tag{32}$$

For both cases, $J_v > 0$ and $J_v < 0$, the partial derivative with respect to PS can be derived as follows $$\frac{\partial J_s}{\partial (PS)} = J_v(1-\sigma)\left(\frac{(c_p - c_i)\left(\frac{-xe^x}{PS}\right)}{(e^x - 1)^2}\right) =$$

$$\frac{J_v(1-\sigma)}{PS}\left(\frac{(c_p - c_i)(-xe^x)}{(e^x - 1)^2}\right) = -\frac{(c_p - c_i)x^2 e^x}{(e^x - 1)^2}.$$

Thus, we have $$\frac{\partial J_s}{\partial (PS)} = \begin{cases} -\frac{(c_p - c_i)x^2 e^x}{(e^x - 1)^2} & \text{if } J_v \neq 0, \\ 0 & \text{if } J_v = 0. \end{cases} \tag{33}$$

The sensitivity equations with respect to PS can be obtained as follows $$\frac{d}{dt}\begin{pmatrix} \frac{\partial V_p}{\partial PS} \\ \frac{\partial c_p}{\partial PS} \\ \frac{\partial V_i}{\partial PS} \\ \frac{\partial c_i}{\partial PS} \end{pmatrix} = Jac_F \begin{pmatrix} \frac{\partial V_p}{\partial PS} \\ \frac{\partial c_p}{\partial PS} \\ \frac{\partial V_i}{\partial PS} \\ \frac{\partial c_i}{\partial PS} \end{pmatrix} + \begin{pmatrix} \frac{\partial F_1}{\partial PS} \\ \frac{\partial F_2}{\partial PS} \\ \frac{\partial F_3}{\partial PS} \\ \frac{\partial F_4}{\partial PS} \end{pmatrix}$$

and so $$\frac{d}{dt}\left(\frac{\partial V_p}{\partial (PS)}\right) = \frac{\partial}{\partial (PS)}\left(\frac{dV_p}{dt}\right)$$

$$= \frac{\partial}{\partial V_p}(J_v + \kappa - J_{UF})\frac{\partial V_p}{\partial (PS)} +$$

$$\frac{\partial}{\partial c_p}(J_v + \kappa - J_{UF})\frac{\partial c_p}{\partial (PS)} + \frac{\partial}{\partial V_i}(J_v + \kappa - J_{UF})\frac{\partial V_i}{\partial (PS)} +$$

$$\frac{\partial}{\partial c_i}(J_v + \kappa - J_{UF})\frac{\partial c_i}{\partial (PS)} + \frac{\partial}{\partial (PS)}(J_v + \kappa - J_{UF})$$

$$= \frac{\partial J_v}{\partial c_p}\frac{\partial c_p}{\partial (PS)} + \frac{\partial J_v}{\partial c_i}\frac{\partial c_i}{\partial (PS)},$$

-continued $$\frac{d}{dt}\left(\frac{\partial c_p}{\partial(PS)}\right) = \frac{\partial}{\partial(PS)}\left(\frac{dc_p}{dt}\right)$$
$$= \frac{\partial}{\partial V_p}\left(\frac{J_s - c_p(J_v + \kappa - J_{UF})}{V_p}\right)\frac{\partial V_p}{\partial(PS)} +$$
$$\frac{\partial}{\partial c_p}\left(\frac{J_s - c_p(J_v + \kappa - J_{UF})}{V_p}\right)\frac{\partial c_p}{\partial(PS)} +$$
$$\frac{\partial}{\partial V_i}\left(\frac{J_s - c_p(J_v + \kappa - J_{UF})}{V_p}\right)\frac{\partial V_i}{\partial(PS)} +$$
$$\frac{\partial}{\partial c_i}\left(\frac{J_s - c_p(J_v + \kappa - J_{UF})}{V_p}\right)\frac{\partial c_i}{\partial(PS)} +$$
$$\frac{\partial}{\partial(PS)}\left(\frac{J_s - c_p(J_v + \kappa - J_{UF})}{V_p}\right)$$
$$= -\left(\frac{J_s - c_p(J_v + \kappa - J_{UF})}{V_p^2}\right)\frac{\partial V_p}{\partial(PS)} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial(PS)} +$$
$$\frac{1}{V_p}\left(\frac{\partial J_s}{\partial c_i} - c_p\frac{\partial J_v}{\partial c_i}\right)\frac{\partial c_i}{\partial(PS)} + \frac{1}{V_p}\frac{\partial J_s}{\partial(PS)},$$

$$\frac{d}{dt}\left(\frac{\partial V_i}{\partial(PS)}\right) = \frac{\partial}{\partial(PS)}\left(\frac{dV_i}{dt}\right)$$
$$= \frac{\partial}{\partial V_p}(-J_v - \kappa)\frac{\partial V_p}{\partial(PS)} + \frac{\partial}{\partial c_p}(-J_v - \kappa)\frac{\partial c_p}{\partial(PS)} +$$
$$\frac{\partial}{\partial V_i}(-J_v - \kappa)\frac{\partial V_i}{\partial(PS)} +$$
$$\frac{\partial}{\partial c_i}(-J_v - \kappa)\frac{\partial c_i}{\partial(PS)} + \frac{\partial}{\partial(PS)}(-J_v - \kappa)$$
$$= -\frac{\partial J_v}{\partial c_p}\frac{\partial c_p}{\partial(PS)} - \frac{\partial J_v}{\partial c_i}\frac{\partial c_i}{\partial(PS)},$$

$$\frac{d}{dt}\left(\frac{\partial c_i}{\partial(PS)}\right) = \frac{\partial}{\partial(PS)}\left(\frac{dc_i}{dt}\right)$$
$$= \frac{\partial}{\partial V_p}\left(\frac{-J_s + c_i(J_v + \kappa)}{V_i}\right)\frac{\partial V_p}{\partial(PS)} +$$
$$\frac{\partial}{\partial c_p}\left(\frac{-J_s + c_i(J_v + \kappa)}{V_i}\right)\frac{\partial c_p}{\partial(PS)} +$$
$$\frac{\partial}{\partial V_i}\left(\frac{-J_s + c_i(J_v + \kappa)}{V_i}\right)\frac{\partial V_i}{\partial(PS)} +$$
$$\frac{\partial}{\partial c_i}\left(\frac{-J_s + c_i(J_v + \kappa)}{V_i}\right)\frac{\partial c_i}{\partial(PS)} +$$
$$\frac{\partial}{\partial(PS)}\left(\frac{-J_s + c_i(J_v + \kappa)}{V_i}\right)$$
$$= \frac{1}{V_i}\left(-\frac{\partial J_s}{\partial c_p} + c_i\frac{\partial J_v}{\partial c_p}\right)\frac{\partial c_p}{\partial(PS)} - \left(\frac{-J_s + c_i(J_v + \kappa)}{V_i^2}\right)\frac{\partial V_i}{\partial(PS)} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial(PS)} -$$
$$\frac{1}{V_i}\frac{\partial J_s}{\partial(PS)}.$$

Sensitivity with Respect to $P_c$
Note that $$\frac{\partial J_v}{\partial P_c} = -L_p. \tag{34}$$

With $$x = \frac{J_v(1-\sigma)}{PS},$$

it follows that $$\frac{\partial}{\partial P_c}(e^x - 1) = e^x\frac{(1-\sigma)}{PS}\frac{\partial J_v}{\partial P_c} = -L_p\frac{(1-\sigma)}{PS}e^x. \tag{35}$$

For $J_v > 0$, the partial derivative of $J_s$ with respect to $P_c$ is $$\frac{\partial J_s}{\partial P_c} = (1-\sigma)\left(\frac{\partial J_v}{\partial P_c}\left(c_i - \frac{c_p - c_i}{e^x - 1}\right) + J_v\left(\frac{(c_p - c_i)\left(-L_p\frac{(1-\sigma)}{PS}e^x\right)}{(e^x - 1)^2}\right)\right)$$
$$= (1-\sigma)\left(-L_p\left(c_i - \frac{c_p - c_i}{e^x - 1}\right) - L_p\left(\frac{(c_p - c_i)\left(\frac{J_v(1-\sigma)}{PS}e^x\right)}{(e^x - 1)^2}\right)\right)$$
$$= (1-\sigma)\left(-L_p\left(c_i - \frac{c_p - c_i}{e^x - 1}\right) - L_p\left(\frac{(c_p - c_i)xe^x}{(e^x - 1)^2}\right)\right),$$
$$\frac{\partial J_s}{\partial P_c} = -L_p(1-\sigma)\left(c_i - \frac{c_p - c_i}{e^x - 1} + \frac{(c_p - c_i)xe^x}{(e^x - 1)^2}\right).$$

Similarly, $$\frac{\partial J_s}{\partial P_c}$$

can be derived when $J_v < 0$. Thus, we have $$\frac{\partial J_s}{\partial P_c} = \begin{cases} -L_p(1-\sigma)\left(c_i - \frac{c_p - c_i}{e^x - 1} + \frac{(c_p - c_i)xe^x}{(e^x - 1)^2}\right) & \text{if } J_v > 0, \\ 0 & \text{if } J_v = 0, \\ -L_p(1-\sigma)\left(c_p - \frac{c_p - c_i}{e^x - 1} + \frac{(c_p - c_i)xe^x}{(e^x - 1)^2}\right) & \text{if } J_v < 0. \end{cases} \tag{36}$$

The sensitivity equations with respect to $P_c$ can be obtained as follows $$\frac{d}{dt}\begin{pmatrix} \frac{\partial V_p}{\partial P_c} \\ \frac{\partial c_p}{\partial P_c} \\ \frac{\partial V_i}{\partial P_c} \\ \frac{\partial c_i}{\partial P_c} \end{pmatrix} = Jac_F \begin{pmatrix} \frac{\partial V_p}{\partial P_c} \\ \frac{\partial c_p}{\partial P_c} \\ \frac{\partial V_i}{\partial P_c} \\ \frac{\partial c_i}{\partial P_c} \end{pmatrix} + \begin{pmatrix} \frac{\partial F_1}{\partial P_c} \\ \frac{\partial F_2}{\partial P_c} \\ \frac{\partial F_3}{\partial P_c} \\ \frac{\partial F_4}{\partial P_c} \end{pmatrix}$$

and so $$\frac{d}{dt}\left(\frac{\partial V_p}{\partial P_c}\right) = \frac{\partial}{\partial P_c}\left(\frac{dV_p}{dt}\right)$$
$$= \frac{\partial}{\partial V_p}(J_v + \kappa - J_{UF})\frac{\partial V_p}{\partial P_c} +$$
$$\frac{\partial}{\partial c_p}(J_v + \kappa - J_{UF})\frac{\partial c_p}{\partial P_c} + \frac{\partial}{\partial V_i}(J_v + \kappa - J_{UF})\frac{\partial V_i}{\partial P_c} +$$
$$\frac{\partial}{\partial c_i}(J_v + \kappa - J_{UF})\frac{\partial c_i}{\partial P_c} + \frac{\partial}{\partial P_c}(J_v + \kappa - J_{UF})$$
$$= \frac{\partial J_v}{\partial c_p}\frac{\partial c_p}{\partial P_c} + \frac{\partial J_v}{\partial c_i}\frac{\partial c_i}{\partial P_c} + \frac{\partial J_v}{\partial P_c}$$
$$= \frac{\partial J_v}{\partial c_p}\frac{\partial c_p}{\partial P_c} + \frac{\partial J_v}{\partial c_i}\frac{\partial c_i}{\partial P_c} - L_p,$$

-continued $$\frac{d}{dt}\left(\frac{\partial c_p}{\partial P_c}\right) = \frac{\partial}{\partial P_c}\left(\frac{dc_p}{dt}\right)$$

$$= \frac{\partial}{\partial V_p}\left(\frac{J_s - c_p(J_v + \kappa - J_{UF})}{V_p}\right)\frac{\partial V_p}{\partial P_c} +$$
$$\frac{\partial}{\partial c_p}\left(\frac{J_s - c_p(J_v + \kappa - J_{UF})}{V_p}\right)\frac{\partial c_p}{\partial P_c} +$$
$$\frac{\partial}{\partial V_i}\left(\frac{J_s - c_p(J_v + \kappa - J_{UF})}{V_p}\right)\frac{\partial V_i}{\partial P_c} +$$
$$\frac{\partial}{\partial c_i}\left(\frac{J_s - c_p(J_v + \kappa - J_{UF})}{V_p}\right)\frac{\partial c_i}{\partial P_c} +$$
$$\frac{\partial}{\partial P_c}\left(\frac{J_s - c_p(J_v + \kappa - J_{UF})}{V_p}\right)$$

$$= -\left(\frac{J_s - c_p(J_v + \kappa - J_{UF})}{V_p^2}\right)\frac{\partial V_p}{\partial P_c} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial P_c} +$$
$$\frac{1}{V_p}\left(\frac{\partial J_s}{\partial c_i} - c_p\frac{\partial J_v}{\partial c_i}\right)\frac{\partial c_i}{\partial P_c} + \frac{1}{V_p}\left(\frac{\partial J_s}{\partial P_c} - c_p\frac{\partial J_v}{\partial P_c}\right)$$

$$= -\left(\frac{J_s - c_p(J_v + \kappa - J_{UF})}{V_p^2}\right)\frac{\partial V_p}{\partial P_c} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial P_c} +$$
$$\frac{1}{V_p}\left(\frac{\partial J_s}{\partial c_i} - c_p\frac{\partial J_v}{\partial c_i}\right)\frac{\partial c_i}{\partial P_c} + \frac{1}{V_p}\left(\frac{\partial J_s}{\partial P_c} + L_p c_p\right),$$

$$\frac{d}{dt}\left(\frac{\partial V_i}{\partial P_c}\right) = \frac{\partial}{\partial P_c}\left(\frac{dV_i}{dt}\right)$$

$$= \frac{\partial}{\partial V_p}(-J_v - \kappa)\frac{\partial V_p}{\partial P_c} + \frac{\partial}{\partial c_p}(-J_v - \kappa)\frac{\partial c_p}{\partial P_c} +$$
$$\frac{\partial}{\partial V_i}(-J_v - \kappa)\frac{\partial V_i}{\partial P_c} + \frac{\partial}{\partial c_i}(-J_v - \kappa)\frac{\partial c_i}{\partial P_c} + \frac{\partial}{\partial P_c}(-J_v - \kappa)$$

$$= -\frac{\partial J_v}{\partial c_p}\frac{\partial c_p}{\partial P_c} - \frac{\partial J_v}{\partial c_i}\frac{\partial c_i}{\partial P_c} - \frac{\partial J_v}{\partial P_c}$$

$$= -\frac{\partial J_v}{\partial c_p}\frac{\partial c_p}{\partial P_c} - \frac{\partial J_v}{\partial c_i}\frac{\partial c_i}{\partial P_c} + L_p,$$

$$\frac{d}{dt}\left(\frac{\partial c_i}{\partial P_c}\right) = \frac{\partial}{\partial P_c}\left(\frac{dc_i}{dt}\right)$$

$$= \frac{\partial}{\partial V_p}\left(\frac{-J_s + c_i(J_v + \kappa)}{V_i}\right)\frac{\partial V_p}{\partial P_c} +$$
$$\frac{\partial}{\partial c_p}\left(\frac{-J_s + c_i(J_v + \kappa)}{V_i}\right)\frac{\partial c_p}{\partial P_c} +$$
$$\frac{\partial}{\partial V_i}\left(\frac{-J_s + c_i(J_v + \kappa)}{V_i}\right)\frac{\partial V_i}{\partial P_c} +$$
$$\frac{\partial}{\partial c_i}\left(\frac{-J_s + c_i(J_v + \kappa)}{V_i}\right)\frac{\partial c_i}{\partial P_c} +$$
$$\frac{\partial}{\partial P_c}\left(\frac{-J_s + c_i(J_v + \kappa)}{V_i}\right)$$

$$= \frac{1}{V_i}\left(-\frac{\partial J_s}{\partial c_p} + c_i\frac{\partial J_v}{\partial c_p}\right)\frac{\partial c_p}{\partial P_c} - \left(\frac{-J_s + c_i(J_v + \kappa)}{V_i^2}\right)\frac{\partial V_i}{\partial P_c} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial P_c} +$$
$$\frac{1}{V_i}\left(-\frac{\partial J_s}{\partial P_c} + c_i\frac{\partial J_v}{\partial P_c}\right)$$

$$= \frac{1}{V_i}\left(-\frac{\partial J_s}{\partial c_p} + c_i\frac{\partial J_v}{\partial c_p}\right)\frac{\partial c_p}{\partial P_c} - \left(\frac{-J_s + c_i(J_v + \kappa)}{V_i^2}\right)\frac{\partial V_i}{\partial P_c} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial P_c} +$$
$$\frac{1}{V_i}\left(-\frac{\partial J_s}{\partial P_c} - L_p c_i\right).$$

Sensitivity with Respect to $P_i$

Note that $$\frac{\partial J_v}{\partial P_i} = L_p. \tag{37}$$

With $$x = \frac{J_v(1-\sigma)}{PS},$$

it follows that $$\frac{\partial}{\partial P_i}(e^x - 1) = e^x \frac{(1-\sigma)}{PS}\frac{\partial J_v}{\partial P_i} = L_p\frac{(1-\sigma)}{PS}e^x. \tag{38}$$

For $J_v > 0$, the partial derivative of $J_s$ with respect to $P_i$ is $$\frac{\partial J_s}{\partial P_i} = (1-\sigma)\left(\frac{\partial J_v}{\partial P_i}\left(c_i - \frac{c_p - c_i}{e^x - 1}\right) + J_v\left(\frac{(c_p - c_i)\left(L_p\frac{(1-\sigma)}{PS}e^x\right)}{(e^x - 1)^2}\right)\right)$$

$$= (1-\sigma)\left(L_p\left(c_i - \frac{c_p - c_i}{e^x - 1}\right) + L_p\left(\frac{(c_p - c_i)\left(\frac{J_v(1-\sigma)}{PS}e^x\right)}{(e^x - 1)^2}\right)\right)$$

$$= (1-\sigma)\left(L_p\left(c_i - \frac{c_p - c_i}{e^x - 1}\right) + L_p\left(\frac{(c_p - c_i)xe^x}{(e^x - 1)^2}\right)\right),$$

$$\frac{\partial J_s}{\partial P_i} = L_p(1-\sigma)\left(c_i - \frac{c_p - c_i}{e^x - 1} + \frac{(c_p - c_i)xe^x}{(e^x - 1)^2}\right).$$

Similarly, $$\frac{\partial J_s}{\partial P_i}$$

can be derived when $J_v < 0$. Thus, we have $$\frac{\partial J_s}{\partial P_i} = \begin{cases} L_p(1-\sigma)\left(c_i - \frac{c_p - c_i}{e^x - 1} + \frac{(c_p - c_i)xe^x}{(e^x - 1)^2}\right) & \text{if } J_v > 0, \\ 0 & \text{if } J_v = 0, \\ L_p(1-\sigma)\left(c_p - \frac{c_p - c_i}{e^x - 1} + \frac{(c_p - c_i)xe^x}{(e^x - 1)^2}\right) & \text{if } J_v < 0. \end{cases} \tag{39}$$

The sensitivity equations with respect to $P_i$ can be obtained as follows $$\frac{d}{dt}\begin{pmatrix}\frac{\partial V_p}{\partial P_i} \\ \frac{\partial c_p}{\partial P_i} \\ \frac{\partial V_i}{\partial P_i} \\ \frac{\partial c_i}{\partial P_i}\end{pmatrix} = Jac_F \begin{pmatrix}\frac{\partial V_p}{\partial P_i} \\ \frac{\partial c_p}{\partial P_i} \\ \frac{\partial V_i}{\partial P_i} \\ \frac{\partial c_i}{\partial P_i}\end{pmatrix} + \begin{pmatrix}\frac{\partial F_1}{\partial P_i} \\ \frac{\partial F_2}{\partial P_i} \\ \frac{\partial F_3}{\partial P_i} \\ \frac{\partial F_4}{\partial P_i}\end{pmatrix}$$

and so $$\frac{d}{dt}\left(\frac{\partial V_p}{\partial P_i}\right) = \frac{\partial}{\partial P_i}\left(\frac{dV_p}{dt}\right)$$
$$= \frac{\partial}{\partial V_p}(J_v + \kappa - J_{UF})\frac{\partial V_p}{\partial P_i} +$$
$$\frac{\partial}{\partial c_p}(J_v + \kappa - J_{UF})\frac{\partial c_p}{\partial P_i} +$$
$$\frac{\partial}{\partial V_i}(J_v + \kappa - J_{UF})\frac{\partial V_i}{\partial P_i} +$$
$$\frac{\partial}{\partial c_i}(J_v + \kappa - J_{UF})\frac{\partial c_i}{\partial P_i} +$$
$$\frac{\partial}{\partial P_i}(J_v + \kappa - J_{UF})$$
$$= \frac{\partial J_v}{\partial c_p}\frac{\partial c_p}{\partial P_i} + \frac{\partial J_v}{\partial c_i}\frac{\partial c_i}{\partial P_i} + \frac{\partial J_v}{\partial P_i}$$
$$= \frac{\partial J_v}{\partial c_p}\frac{\partial c_p}{\partial P_i} + \frac{\partial J_v}{\partial c_i}\frac{\partial c_i}{\partial P_i} + L_p,$$

$$\frac{d}{dt}\left(\frac{\partial c_p}{\partial P_i}\right) = \frac{\partial}{\partial P_i}\left(\frac{dc_p}{dt}\right)$$
$$= \frac{\partial}{\partial V_p}\left(\frac{J_s - c_p(J_v + \kappa - J_{UF})}{V_p}\right)\frac{\partial V_p}{\partial P_i} +$$
$$\frac{\partial}{\partial c_p}\left(\frac{J_s - c_p(J_v + \kappa - J_{UF})}{V_p}\right)\frac{\partial c_p}{\partial P_i} +$$
$$\frac{\partial}{\partial V_i}\left(\frac{J_s - c_p(J_v + \kappa - J_{UF})}{V_p}\right)\frac{\partial V_i}{\partial P_i} +$$
$$\frac{\partial}{\partial c_i}\left(\frac{J_s - c_p(J_v + \kappa - J_{UF})}{V_p}\right)\frac{\partial c_i}{\partial P_i} +$$
$$\frac{\partial}{\partial P_i}\left(\frac{J_s - c_p(J_v + \kappa - J_{UF})}{V_p}\right)$$
$$= -\left(\frac{J_s - c_p(J_v + \kappa - J_{UF})}{V_p^2}\right)\frac{\partial V_p}{\partial P_i} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial P_i} +$$
$$\frac{1}{V_p}\left(\frac{\partial J_s}{\partial c_i} - c_p\frac{\partial J_v}{\partial c_i}\right)\frac{\partial c_i}{\partial P_i} + \frac{1}{V_p}\left(\frac{\partial J_s}{\partial P_i} - c_p\frac{\partial J_v}{\partial P_i}\right)$$
$$= -\left(\frac{J_s - c_p(J_v + \kappa - J_{UF})}{V_p^2}\right)\frac{\partial V_p}{\partial P_i} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial P_i} +$$
$$\frac{1}{V_p}\left(\frac{\partial J_s}{\partial c_i} - c_p\frac{\partial J_v}{\partial c_i}\right)\frac{\partial c_i}{\partial P_i} + \frac{1}{V_p}\left(\frac{\partial J_s}{\partial P_i} - L_p c_p\right),$$

$$\frac{d}{dt}\left(\frac{\partial V_i}{\partial P_i}\right) = \frac{\partial}{\partial P_i}\left(\frac{dV_i}{dt}\right)$$
$$= \frac{\partial}{\partial V_p}(-J_v - \kappa)\frac{\partial V_p}{\partial P_i} + \frac{\partial}{\partial c_p}(-J_v - \kappa)\frac{\partial c_p}{\partial P_i} +$$
$$\frac{\partial}{\partial V_i}(-J_v - \kappa)\frac{\partial V_i}{\partial P_i} + \frac{\partial}{\partial c_i}(-J_v - \kappa)\frac{\partial c_i}{\partial P_i} +$$
$$\frac{\partial}{\partial P_i}(-J_v - \kappa)$$
$$= -\frac{\partial J_v}{\partial c_p}\frac{\partial c_p}{\partial P_i} - \frac{\partial J_v}{\partial c_i}\frac{\partial c_i}{\partial P_i} - \frac{\partial J_v}{\partial P_i}$$
$$= -\frac{\partial J_v}{\partial c_p}\frac{\partial c_p}{\partial P_i} - \frac{\partial J_v}{\partial c_i}\frac{\partial c_i}{\partial P_i} - L_p,$$

$$\frac{d}{dt}\left(\frac{\partial c_i}{\partial P_i}\right) = \frac{\partial}{\partial P_i}\left(\frac{dc_i}{dt}\right)$$
$$= \frac{\partial}{\partial V_p}\left(\frac{-J_s + c_i(J_v + \kappa)}{V_i}\right)\frac{\partial V_p}{\partial P_i} +$$
$$\frac{\partial}{\partial c_p}\left(\frac{-J_s + c_i(J_v + \kappa)}{V_i}\right)\frac{\partial c_p}{\partial P_i} +$$
$$\frac{\partial}{\partial V_i}\left(\frac{-J_s + c_i(J_v + \kappa)}{V_i}\right)\frac{\partial V_i}{\partial P_i} +$$
$$\frac{\partial}{\partial c_i}\left(\frac{-J_s + c_i(J_v + \kappa)}{V_i}\right)\frac{\partial c_i}{\partial P_i} +$$
$$\frac{\partial}{\partial P_i}\left(\frac{-J_s + c_i(J_v + \kappa)}{V_i}\right)$$
$$= \frac{1}{V_i}\left(-\frac{\partial J_s}{\partial c_p} + c_i\frac{\partial J_v}{\partial c_p}\right)\frac{\partial c_p}{\partial P_i} - \left(\frac{-J_s + c_i(J_v + \kappa)}{V_i^2}\right)\frac{\partial V_i}{\partial P_i} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial P_i} +$$
$$\frac{1}{V_i}\left(-\frac{\partial J_s}{\partial P_i} + c_i\frac{\partial J_v}{\partial P_i}\right)$$
$$= \frac{1}{V_i}\left(-\frac{\partial J_s}{\partial c_p} + c_i\frac{\partial J_v}{\partial c_p}\right)\frac{\partial c_p}{\partial P_i} - \left(\frac{-J_s + c_i(J_v + \kappa)}{V_i^2}\right)\frac{\partial V_i}{\partial P_i} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial P_i} + \frac{1}{V_i}\left(-\frac{\partial J_s}{\partial P_i} + L_p c_i\right).$$

Sensitivity with Respect to $a_{p_1}$

Note that $$\frac{\partial J_v}{\partial a_{p_1}} = L_p \sigma c_p. \quad (40)$$

With $$x = \frac{J_v(1-\sigma)}{PS},$$

it follows that $$\frac{\partial}{\partial a_{p_1}}(e^x - 1) = e^x \frac{(1-\sigma)}{PS}\frac{\partial J_v}{\partial a_{p_1}}. \quad (41)$$

For $J_v > 0$, the partial derivative of $J_s$ with respect to $a_{p_1}$ is $$\frac{\partial J_s}{\partial a_{p_1}} = (1-\sigma)\left(\frac{\partial J_v}{\partial a_{p_1}}\left(c_i - \frac{c_p - c_i}{e^x - 1}\right) + \right.$$

$$J_v\left(\frac{(c_p - c_i)\left(e^x \frac{(1-\sigma)}{PS}\frac{\partial J_v}{\partial a_{p_1}}\right)}{(e^x - 1)^2}\right)\right)$$

$$= (1-\sigma)\left(\frac{\partial J_v}{\partial a_{p_1}}\left(c_i - \frac{c_p - c_i}{e^x - 1}\right) + \right.$$

$$\left.\frac{\partial J_v}{\partial a_{p_1}}\left(\frac{(c_p - c_i)\left(\frac{J_v(1-\sigma)}{PS}e^x\right)}{(e^x - 1)^2}\right)\right)$$

$$= (1-\sigma)\left(\left(c_i - \frac{c_p - c_i}{e^x - 1}\right) + \left(\frac{(c_p - c_i)xe^x}{(e^x - 1)^2}\right)\right)\frac{\partial J_v}{\partial a_{p_1}},$$

$$\frac{\partial J_s}{\partial P_i} = (1-\sigma)\left(c_i - \frac{c_p - c_i}{e^x - 1} + \frac{(c_p - c_i)xe^x}{(e^x - 1)^2}\right)\frac{\partial J_v}{\partial a_{p_1}}.$$

$$\frac{\partial J_s}{\partial a_{p_1}}$$

can be derived in a similar manner when $J_v < 0$. Thus, we have $$\frac{\partial J_s}{\partial a_{p_1}} = \begin{cases} (1-\sigma)\left(c_i - \frac{c_p - c_i}{e^x - 1} + \frac{(c_p - c_i)xe^x}{(e^x - 1)^2}\right)\frac{\partial J_v}{\partial a_{p_1}} & \text{if } J_v > 0, \\ 0 & \text{if } J_v = 0, \\ (1-\sigma)\left(c_p - \frac{c_p - c_i}{e^x - 1} + \frac{(c_p - c_i)xe^x}{(e^x - 1)^2}\right)\frac{\partial J_v}{\partial a_{p_1}} & \text{if } J_v < 0. \end{cases} \quad (42)$$

The sensitivity equations with respect to $a_{p_1}$ can be obtained as follows $$\frac{d}{dt}\begin{pmatrix} \frac{\partial V_p}{\partial a_{p_1}} \\ \frac{\partial c_p}{\partial a_{p_1}} \\ \frac{\partial V_i}{\partial a_{p_1}} \\ \frac{\partial c_i}{\partial a_{p_1}} \end{pmatrix} = Jac_F \begin{pmatrix} \frac{\partial V_p}{\partial a_{p_1}} \\ \frac{\partial c_p}{\partial a_{p_1}} \\ \frac{\partial V_i}{\partial a_{p_1}} \\ \frac{\partial c_i}{\partial a_{p_1}} \end{pmatrix} + \begin{pmatrix} \frac{\partial F_1}{\partial a_{p_1}} \\ \frac{\partial F_2}{\partial a_{p_1}} \\ \frac{\partial F_3}{\partial a_{p_1}} \\ \frac{\partial F_4}{\partial a_{p_1}} \end{pmatrix}$$

and so $$\frac{d}{dt}\left(\frac{\partial V_p}{\partial a_{p_1}}\right) = \frac{\partial}{\partial a_{p_1}}\left(\frac{dV_p}{dt}\right)$$

$$= \frac{\partial}{\partial V_p}(J_v + \kappa - J_{UF})\frac{\partial V_p}{\partial a_{p_1}} +$$

$$\frac{\partial}{\partial c_p}(J_v + \kappa - J_{UF})\frac{\partial c_p}{\partial a_{p_1}} +$$

$$\frac{\partial}{\partial V_i}(J_v + \kappa - J_{UF})\frac{\partial V_i}{\partial a_{p_1}} +$$

$$\frac{\partial}{\partial c_i}(J_v + \kappa - J_{UF})\frac{\partial c_i}{\partial a_{p_1}} + \frac{\partial}{\partial a_{p_1}}(J_v + \kappa - J_{UF})$$

$$= \frac{\partial J_v}{\partial c_p}\frac{\partial c_p}{\partial a_{p_1}} + \frac{\partial J_v}{\partial c_i}\frac{\partial c_i}{\partial a_{p_1}} + \frac{\partial J_v}{\partial a_{p_1}},$$

$$\frac{d}{dt}\left(\frac{\partial c_p}{\partial a_{p_1}}\right) = \frac{\partial}{\partial a_{p_1}}\left(\frac{dc_p}{dt}\right)$$

$$= \frac{\partial}{\partial V_p}\left(\frac{J_s - c_p(J_v + \kappa - J_{UF})}{V_p}\right)\frac{\partial V_p}{\partial a_{p_1}} +$$

$$\frac{\partial}{\partial c_p}\left(\frac{J_s - c_p(J_v + \kappa - J_{UF})}{V_p}\right)\frac{\partial c_p}{\partial a_{p_1}} +$$

$$\frac{\partial}{\partial V_i}\left(\frac{J_s - c_p(J_v + \kappa - J_{UF})}{V_p}\right)\frac{\partial V_i}{\partial a_{p_1}} +$$

$$\frac{\partial}{\partial c_i}\left(\frac{J_s - c_p(J_v + \kappa - J_{UF})}{V_p}\right)\frac{\partial c_i}{\partial a_{p_1}} +$$

$$\frac{\partial}{\partial a_{p_1}}\left(\frac{J_s - c_p(J_v + \kappa - J_{UF})}{V_p}\right)$$

$$= -\left(\frac{J_s - c_p(J_v + \kappa - J_{UF})}{V_p^2}\right)\frac{\partial V_p}{\partial a_{p_1}} +$$

$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial a_{p_1}} +$$

$$\frac{1}{V_p}\left(\frac{\partial J_s}{\partial c_i} - c_p\frac{\partial J_v}{\partial c_i}\right)\frac{\partial c_i}{\partial a_{p_1}} + \frac{1}{V_p}\left(\frac{\partial J_s}{\partial a_{p_1}} - c_p\frac{\partial J_v}{\partial a_{p_1}}\right),$$

$$\frac{d}{dt}\left(\frac{\partial V_i}{\partial a_{p_1}}\right) = \frac{\partial}{\partial a_{p_1}}\left(\frac{dV_i}{dt}\right)$$

$$= \frac{\partial}{\partial V_p}(-J_v - \kappa)\frac{\partial V_p}{\partial a_{p_1}} + \frac{\partial}{\partial c_p}(-J_v - \kappa)\frac{\partial c_p}{\partial a_{p_1}} +$$

$$\frac{\partial}{\partial V_i}(-J_v - \kappa)\frac{\partial V_i}{\partial a_{p_1}} + \frac{\partial}{\partial c_i}(-J_v - \kappa)\frac{\partial c_i}{\partial a_{p_1}} +$$

$$\frac{\partial}{\partial a_{p_1}}(-J_v - \kappa)$$

$$= -\frac{\partial J_v}{\partial c_p}\frac{\partial c_p}{\partial a_{p_1}} - \frac{\partial J_v}{\partial c_i}\frac{\partial c_i}{\partial a_{p_1}} - \frac{\partial J_v}{\partial a_{p_1}},$$

-continued $$\frac{d}{dt}\left(\frac{\partial c_i}{\partial a_{p_1}}\right) = \frac{\partial}{\partial a_{p_1}}\left(\frac{dc_i}{dt}\right)$$

$$= \frac{\partial}{\partial V_p}\left(\frac{-J_s + c_i(J_v + \kappa)}{V_i}\right)\frac{\partial V_p}{\partial a_{p_1}} +$$

$$\frac{\partial}{\partial c_p}\left(\frac{-J_s + c_i(J_v + \kappa)}{V_i}\right)\frac{\partial c_p}{\partial a_{p_1}} +$$

$$\frac{\partial}{\partial V_i}\left(\frac{-J_s + c_i(J_v + \kappa)}{V_i}\right)\frac{\partial V_i}{\partial a_{p_1}} +$$

$$\frac{\partial}{\partial c_i}\left(\frac{-J_s + c_i(J_v + \kappa)}{V_i}\right)\frac{\partial c_i}{\partial a_{p_1}} +$$

$$\frac{\partial}{\partial a_{p_1}}\left(\frac{-J_s + c_i(J_v + \kappa)}{V_i}\right)$$

$$= \frac{1}{V_i}\left(-\frac{\partial J_s}{\partial c_p} + c_i\frac{\partial J_v}{\partial c_p}\right)\frac{\partial c_p}{\partial a_{p_1}} -$$

$$\left(\frac{-J_s + c_i(J_v + \kappa)}{V_i^2}\right)\frac{\partial V_i}{\partial a_{p_1}} +$$

$$\frac{1}{V_i}\left(-\frac{\partial J_s}{\partial c_i} + c_i\frac{\partial J_v}{\partial c_i} + (J_v + \kappa)\right)\frac{\partial c_i}{\partial a_{p_1}} +$$

$$\frac{1}{V_i}\left(-\frac{\partial J_s}{\partial a_{p_1}} + c_i\frac{\partial J_v}{\partial a_{p_1}}\right).$$

Sensitivity with Respect to $a_{p_2}$

Note that $$\frac{\partial J_v}{\partial a_{p_2}} = L_p \sigma_p^2. \quad (43)$$

With $$x = \frac{J_v(1-\sigma)}{PS},$$

it follows that $$\frac{\partial}{\partial a_{p_2}}(e^x - 1) = e^x \frac{(1-\sigma)}{PS}\frac{\partial J_v}{\partial a_{p_2}}. \quad (44)$$

For $J_v > 0$, the partial derivative of $J_s$ with respect to $a_{p_2}$ is $$\frac{\partial J_s}{\partial a_{p_2}} = (1-\sigma)\left(\frac{\partial J_v}{\partial a_{p_2}}\left(c_i - \frac{c_p - c_i}{e^x - 1}\right) + J_v\left(\frac{(c_p - c_i)\left(e^x\frac{(1-\sigma)}{PS}\frac{\partial J_v}{\partial a_{p_2}}\right)}{(e^x - 1)^2}\right)\right)$$

$$= (1-\sigma)\left(\frac{\partial J_v}{\partial a_{p_2}}\left(c_i - \frac{c_p - c_i}{e^x - 1}\right) + \frac{\partial J_v}{\partial a_{p_2}}\left(\frac{(c_p - c_i)\left(\frac{J_v(1-\sigma)}{PS}e^x\right)}{(e^x - 1)^2}\right)\right)$$

$$= (1-\sigma)\left(\left(c_i - \frac{c_p - c_i}{e^x - 1}\right) + \left(\frac{(c_p - c_i)xe^x}{(e^x - 1)^2}\right)\right)\frac{\partial J_v}{\partial a_{p_2}},$$

$$\frac{\partial J_s}{\partial a_{p_2}} = (1-\sigma)\left(\left(c_i - \frac{c_p - c_i}{e^x - 1} + \frac{(c_p - c_i)xe^x}{(e^x - 1)^2}\right)\right)\frac{\partial J_v}{\partial a_{p_2}}.$$

$$\frac{\partial J_s}{\partial a_{p_2}}$$

can be derived in a similar manner when $J_v < 0$. Thus, we have $$\frac{\partial J_s}{\partial a_{p_2}} = \begin{cases} (1-\sigma)\left(c_i - \frac{c_p - c_i}{e^x - 1} + \frac{(c_p - c_i)xe^x}{(e^x - 1)^2}\right)\frac{\partial J_v}{\partial a_{p_2}} & \text{if } J_v > 0, \\ 0 & \text{if } J_v = 0, \\ (1-\sigma)\left(c_p - \frac{c_p - c_i}{e^x - 1} + \frac{(c_p - c_i)xe^x}{(e^x - 1)^2}\right)\frac{\partial J_v}{\partial a_{p_2}} & \text{if } J_v < 0, \end{cases} \quad (45)$$

The sensitivity equations with respect to $a_{p_2}$ can be obtained as follows $$\frac{d}{dt}\begin{pmatrix}\frac{\partial V_p}{\partial a_{p_2}} \\ \frac{\partial c_p}{\partial a_{p_2}} \\ \frac{\partial V_i}{\partial a_{p_2}} \\ \frac{\partial c_i}{\partial a_{p_2}}\end{pmatrix} = Jac_F \begin{pmatrix}\frac{\partial V_p}{\partial a_{p_2}} \\ \frac{\partial c_p}{\partial a_{p_2}} \\ \frac{\partial V_i}{\partial a_{p_2}} \\ \frac{\partial c_i}{\partial a_{p_2}}\end{pmatrix} + \begin{pmatrix}\frac{\partial F_1}{\partial a_{p_2}} \\ \frac{\partial F_2}{\partial a_{p_2}} \\ \frac{\partial F_3}{\partial a_{p_2}} \\ \frac{\partial F_4}{\partial a_{p_2}}\end{pmatrix}$$

and so $$\frac{d}{dt}\left(\frac{\partial V_p}{\partial a_{p_2}}\right) = \frac{\partial}{\partial a_{p_2}}\left(\frac{dV_p}{dt}\right)$$

$$= \frac{\partial}{\partial V_p}(J_v + \kappa - J_{UF})\left(\frac{\partial V_p}{\partial a_{p_2}}\right) + \frac{\partial}{\partial c_p}(J_v + \kappa - J_{UF})\frac{\partial c_p}{\partial a_{p_2}} +$$

$$\frac{\partial}{\partial V_i}(J_v + \kappa - J_{UF})\frac{\partial V_i}{\partial a_{p_2}} +$$

$$\frac{\partial}{\partial c_i}(J_v + \kappa - J_{UF})\frac{\partial c_i}{\partial a_{p_2}} + \frac{\partial}{\partial a_{p_2}}(J_v + \kappa - J_{UF})$$

$$= \frac{\partial J_v}{\partial c_p}\frac{\partial c_p}{\partial a_{p_2}} + \frac{\partial J_v}{\partial c_i}\frac{\partial c_i}{\partial a_{p_2}} + \frac{\partial J_v}{\partial a_{p_2}},$$

$$\frac{d}{dt}\left(\frac{\partial c_p}{\partial a_{p_2}}\right) = \frac{\partial}{\partial a_{p_2}}\left(\frac{dc_p}{dt}\right)$$

$$= \frac{\partial}{\partial V_p}\left(\frac{J_s - c_p(J_v + \kappa - J_{UF})}{V_p}\right)\frac{\partial V_p}{\partial a_{p_2}} +$$

$$\frac{\partial}{\partial c_p}\left(\frac{J_s - c_p(J_v + \kappa - J_{UF})}{V_p}\right)\frac{\partial c_p}{\partial a_{p_2}} +$$

$$\frac{\partial}{\partial V_i}\left(\frac{J_s - c_p(J_v + \kappa - J_{UF})}{V_p}\right)\frac{\partial V_i}{\partial a_{p_2}} +$$

$$\frac{\partial}{\partial c_i}\left(\frac{J_s - c_p(J_v + \kappa - J_{UF})}{V_p}\right)\frac{\partial c_i}{\partial a_{p_2}} +$$

$$\frac{\partial}{\partial a_{p_2}}\left(\frac{J_s - c_p(J_v + \kappa - J_{UF})}{V_p}\right)$$

$$= -\left(\frac{J_s - c_p(J_v + \kappa - J_{UF})}{V_p^2}\right)\frac{\partial V_p}{\partial a_{p_2}} +$$

$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial a_{p_2}} +$$

$$\frac{1}{V_p}\left(\frac{\partial J_s}{\partial c_i} - c_p\frac{\partial J_v}{\partial c_i}\right)\frac{\partial c_i}{\partial a_{p_2}} + \frac{1}{V_p}\left(\frac{\partial J_s}{\partial a_{p_2}} - c_p\frac{\partial J_v}{\partial a_{p_2}}\right),$$

-continued $$\frac{d}{dt}\left(\frac{\partial V_i}{\partial a_{p_2}}\right) = \frac{\partial}{\partial a_{p_2}}\left(\frac{dV_i}{dt}\right)$$
$$= +\frac{\partial}{\partial V_p}(-J_v - \kappa)\frac{\partial V_p}{\partial a_{p_2}} + \frac{\partial}{\partial c_p}(-J_v - \kappa)\frac{\partial c_p}{\partial a_{p_2}} +$$
$$\frac{\partial}{\partial V_i}(-J_v - \kappa)\frac{\partial V_i}{\partial a_{p_2}} +$$
$$\frac{\partial}{\partial c_i}(-J_v - \kappa)\frac{\partial c_i}{\partial a_{p_2}} + \frac{\partial}{\partial a_{p_2}}(-J_v - \kappa)$$
$$= -\frac{\partial J_v}{\partial c_p}\frac{\partial c_p}{\partial a_{p_2}} - \frac{\partial J_v}{\partial c_i}\frac{\partial c_i}{\partial a_{p_2}} - \frac{\partial J_v}{\partial a_{p_2}},$$

$$\frac{d}{dt}\left(\frac{\partial c_i}{\partial a_{p_2}}\right) = \frac{\partial}{\partial a_{p_2}}\left(\frac{dc_i}{dt}\right)$$
$$= \frac{\partial}{\partial V_p}\left(\frac{-J_s + c_i(J_v + \kappa)}{V_i}\right)\frac{\partial V_p}{\partial a_{p_2}} +$$
$$\frac{\partial}{\partial c_p}\left(\frac{-J_s + c_i(J_v + \kappa)}{V_i}\right)\frac{\partial c_p}{\partial a_{p_2}} +$$
$$\frac{\partial}{\partial V_i}\left(\frac{-J_s + c_i(J_v + \kappa)}{V_i}\right)\frac{\partial V_i}{\partial a_{p_2}} +$$
$$\frac{\partial}{\partial c_i}\left(\frac{-J_s + c_i(J_v + \kappa)}{V_i}\right)\frac{\partial c_i}{\partial a_{p_2}} +$$
$$\frac{\partial}{\partial a_{p_2}}\left(\frac{-J_s + c_i(J_v + \kappa)}{V_i}\right)$$
$$= \frac{1}{V_i}\left(-\frac{\partial J_s}{\partial c_p} + c_i\frac{\partial J_v}{\partial c_p}\right)\frac{\partial c_p}{\partial a_{p_2}} -$$
$$\left(\frac{-J_s + c_i(J_v + \kappa)}{V_i^2}\right)\frac{\partial V_i}{\partial a_{p_2}} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial a_{p_2}} +$$
$$\frac{1}{V_i}\left(-\frac{\partial J_s}{\partial a_{p_2}} + c_i\frac{\partial J_v}{\partial a_{p_2}}\right).$$

Sensitivity with Respect to $a_{i_1}$
Note that $$\frac{\partial J_v}{\partial a_{i_1}} = -L_p \sigma c_i. \tag{46}$$

With $$x = \frac{J_v(1-\sigma)}{PS},$$

it follows that $$\frac{\partial}{\partial a_{i_1}}(e^x - 1) = e^x \frac{(1-\sigma)}{PS}\frac{\partial J_v}{\partial a_{i_1}}. \tag{47}$$

For $J_v > 0$, the partial derivative of $J_s$ with respect to $a_{i_1}$ is $$\frac{\partial J_s}{\partial a_{i_1}} = (1-\sigma)\left(\frac{\partial J_v}{\partial a_{i_1}}\left(c_i - \frac{c_p - c_i}{e^x - 1}\right) + J_v\left(\frac{(c_p - c_i)\left(e^x \frac{(1-\sigma)}{PS}\frac{\partial J_v}{\partial a_{i_1}}\right)}{(e^x - 1)^2}\right)\right)$$

$$= (1-\sigma)\left(\frac{\partial J_v}{\partial a_{i_1}}\left(c_i - \frac{c_p - c_i}{e^x - 1}\right) + \frac{\partial J_v}{\partial a_{i_1}}\left(\frac{(c_p - c_i)\left(\frac{J_v(1-\sigma)}{PS}e^x\right)}{(e^x - 1)^2}\right)\right)$$

$$= (1-\sigma)\left(\left(c_i - \frac{c_p - c_i}{e^x - 1}\right) + \left(\frac{(c_p - c_i)xe^x}{(e^x - 1)^2}\right)\right)\frac{\partial J_v}{\partial a_{i_1}},$$

$$\frac{\partial J_s}{\partial a_{i_1}} = (1-\sigma)\left(c_i - \frac{c_p - c_i}{e^x - 1} + \frac{(c_p - c_i)xe^x}{(e^x - 1)^2}\right)\frac{\partial J_v}{\partial a_{i_1}}.$$

$$\frac{\partial J_s}{\partial a_{i_1}}$$

can be derived in a similar manner when $J_v < 0$. Thus, we have $$\frac{\partial J_s}{\partial a_{i_1}} = \begin{cases} (1-\sigma)\left(c_i - \frac{c_p - c_i}{e^x - 1} + \frac{(c_p - c_i)xe^x}{(e^x - 1)^2}\right)\frac{\partial J_v}{\partial a_{i_1}} & \text{if } J_v > 0, \\ 0 & \text{if } J_v = 0, \\ (1-\sigma)\left(c_p - \frac{c_p - c_i}{e^x - 1} + \frac{(c_p - c_i)xe^x}{(e^x - 1)^2}\right)\frac{\partial J_v}{\partial a_{i_1}} & \text{if } J_v < 0. \end{cases} \tag{48}$$

The sensitivity equations with respect to $a_{i_1}$ can be obtained as follows $$\frac{d}{dt}\begin{pmatrix}\frac{\partial V_p}{\partial a_{i_1}} \\ \frac{\partial c_p}{\partial a_{i_1}} \\ \frac{\partial V_i}{\partial a_{i_1}} \\ \frac{\partial c_i}{\partial a_{i_1}}\end{pmatrix} = Jac_F \begin{pmatrix}\frac{\partial V_p}{\partial a_{i_1}} \\ \frac{\partial c_p}{\partial a_{i_1}} \\ \frac{\partial V_i}{\partial a_{i_1}} \\ \frac{\partial c_i}{\partial a_{i_1}}\end{pmatrix} + \begin{pmatrix}\frac{\partial F_1}{\partial a_{i_1}} \\ \frac{\partial F_2}{\partial a_{i_1}} \\ \frac{\partial F_3}{\partial a_{i_1}} \\ \frac{\partial F_4}{\partial a_{i_1}}\end{pmatrix}$$

and so $$\frac{d}{dt}\left(\frac{\partial V_p}{\partial a_{i_1}}\right) = \frac{\partial}{\partial a_{i_1}}\left(\frac{dV_p}{dt}\right)$$
$$= \frac{\partial}{\partial V_p}(J_v + \kappa - J_{UF})\left(\frac{\partial V_p}{\partial a_{i_1}}\right) + \frac{\partial}{\partial c_p}(J_v + \kappa - J_{UF})\frac{\partial c_p}{\partial a_{i_1}} +$$
$$\frac{\partial}{\partial V_i}(J_v + \kappa - J_{UF})\frac{\partial V_i}{\partial a_{i_1}} +$$
$$\frac{\partial}{\partial a_{i_1}}(J_v + \kappa - J_{UF})\frac{\partial c_i}{\partial a_{i_1}} + \frac{\partial}{\partial a_{i_1}}(J_v + \kappa - J_{UF})$$
$$= \frac{\partial J_v}{\partial c_p}\frac{\partial c_p}{\partial a_{i_1}} + \frac{\partial J_v}{\partial c_i}\frac{\partial c_i}{\partial a_{i_1}} + \frac{\partial J_v}{\partial a_{i_1}},$$

-continued $$\frac{d}{dt}\left(\frac{\partial c_p}{\partial a_{i_1}}\right) = \frac{\partial}{\partial a_{i_1}}\left(\frac{dc_p}{dt}\right)$$

$$= \frac{\partial}{\partial V_p}\left(\frac{J_s - c_p(J_v + \kappa - J_{UF})}{V_p}\right)\frac{\partial V_p}{\partial a_{i_1}} +$$

$$\frac{\partial}{\partial c_p}\left(\frac{J_s - c_p(J_v + \kappa - J_{UF})}{V_p}\right)\frac{\partial c_p}{\partial a_{i_1}} +$$

$$\frac{\partial}{\partial V_i}\left(\frac{J_s - c_p(J_v + \kappa - J_{UF})}{V_p}\right)\frac{\partial V_i}{\partial a_{i_1}} +$$

$$\frac{\partial}{\partial c_i}\left(\frac{J_s - c_p(J_v + \kappa - J_{UF})}{V_p}\right)\frac{\partial c_i}{\partial a_{i_1}} +$$

$$\frac{\partial}{\partial a_{i_1}}\left(\frac{J_s - c_p(J_v + \kappa - J_{UF})}{V_p}\right)$$

$$= -\left(\frac{J_s - c_p(J_v + \kappa - J_{UF})}{V_p^2}\right)\frac{\partial V_p}{\partial a_{i_1}} +$$

$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial a_{i_1}} +$$

$$\frac{1}{V_p}\left(\frac{\partial J_s}{\partial c_i} - c_p\frac{\partial J_v}{\partial c_i}\right)\frac{\partial c_i}{\partial a_{i_1}} + \frac{1}{V_p}\left(\frac{\partial J_s}{\partial a_{i_1}} - c_p\frac{\partial J_v}{\partial a_{i_1}}\right),$$

$$\frac{d}{dt}\left(\frac{\partial V_i}{\partial a_{i_1}}\right) = \frac{\partial}{\partial a_{i_1}}\left(\frac{dV_i}{dt}\right)$$

$$= +\frac{\partial}{\partial V_p}(-J_v - \kappa)\frac{\partial V_p}{\partial a_{i_1}} + \frac{\partial}{\partial c_p}(-J_v - \kappa)\frac{\partial c_p}{\partial a_{i_1}} +$$

$$\frac{\partial}{\partial V_i}(-J_v - \kappa)\frac{\partial V_i}{\partial a_{i_1}} +$$

$$\frac{\partial}{\partial c_i}(-J_v - \kappa)\frac{\partial c_i}{\partial a_{i_1}} + \frac{\partial}{\partial a_{i_1}}(-J_v - \kappa)$$

$$= -\frac{\partial J_v}{\partial c_p}\frac{\partial c_p}{\partial a_{i_1}} - \frac{\partial J_v}{\partial c_i}\frac{\partial c_i}{\partial a_{i_1}} - \frac{\partial J_v}{\partial a_{i_1}},$$

$$\frac{d}{dt}\left(\frac{\partial c_i}{\partial a_{i_1}}\right) = \frac{\partial}{\partial a_{p_2}}\left(\frac{dc_i}{dt}\right)$$

$$= \frac{\partial}{\partial V_p}\left(\frac{-J_s + c_i(J_v + \kappa)}{V_i}\right)\frac{\partial V_p}{\partial a_{i_1}} +$$

$$\frac{\partial}{\partial c_p}\left(\frac{-J_s + c_i(J_v + \kappa)}{V_i}\right)\frac{\partial c_p}{\partial a_{i_1}} +$$

$$\frac{\partial}{\partial V_i}\left(\frac{-J_s + c_i(J_v + \kappa)}{V_i}\right)\frac{\partial V_i}{\partial a_{i_1}} +$$

$$\frac{\partial}{\partial c_i}\left(\frac{-J_s + c_i(J_v + \kappa)}{V_i}\right)\frac{\partial c_i}{\partial a_{i_1}} +$$

$$\frac{\partial}{\partial a_{i_1}}\left(\frac{-J_s + c_i(J_v + \kappa)}{V_i}\right)$$

$$= \frac{1}{V_i}\left(-\frac{\partial J_s}{\partial c_p} + c_i\frac{\partial J_v}{\partial c_p}\right)\frac{\partial c_p}{\partial a_{i_1}} -$$

$$\left(\frac{-J_s + c_i(J_v + \kappa)}{V_i^2}\right)\frac{\partial V_i}{\partial a_{i_1}} +$$

$$\frac{1}{V_i}\left(-\frac{\partial J_s}{\partial c_i} + c_i\frac{\partial J_v}{\partial c_i} + (J_v + \kappa)\right)\frac{\partial c_i}{\partial a_{i_1}} +$$

$$\frac{1}{V_i}\left(-\frac{\partial J_s}{\partial a_{i_1}} + c_i\frac{\partial J_v}{\partial a_{i_1}}\right).$$

Sensitivity with Respect to $a_{i_2}$

Note that $$\frac{\partial J_v}{\partial a_{i_2}} = -L_p \sigma c_i^2. \quad (49)$$

With $$x = \frac{J_v(1-\sigma)}{PS},$$

it follows that $$\frac{\partial}{\partial a_{p_2}}(e^x - 1) = e^x \frac{(1-\sigma)}{PS}\frac{\partial J_v}{\partial a_{i_2}}. \quad (50)$$

For $J_v > 0$, the partial derivative of $J_s$ with respect to $a_{i_2}$ is $$\frac{\partial J_s}{\partial a_{i_2}} = (1-\sigma)\left(\frac{\partial J_v}{\partial \alpha_{i_2}}\left(c_i - \frac{c_p - c_i}{e^x - 1}\right) + J_v\left(\frac{(c_p - c_i)\left(e^x\frac{(1-\sigma)}{PS}\frac{\partial J_v}{\partial \alpha_{i_2}}\right)}{(e^x - 1)^2}\right)\right)$$

$$= (1-\sigma)\left(\frac{\partial J_v}{\partial \alpha_{i_2}}\left(c_i - \frac{c_p - c_i}{e^x - 1}\right) + \frac{\partial J_v}{\partial \alpha_{i_2}}\left(\frac{(c_p - c_i)\left(\frac{J_v(1-\sigma)}{PS}e^x\right)}{(e^x - 1)^2}\right)\right)$$

$$= (1-\sigma)\left(\left(c_i - \frac{c_p - c_i}{e^x - 1}\right) + \left(\frac{(c_p - c_i)xe^x}{(e^x - 1)^2}\right)\right)\frac{\partial J_v}{\partial \alpha_{i_2}},$$

$$\frac{\partial J_s}{\partial a_{i_2}} = (1-\sigma)\left(c_i - \frac{c_p - c_i}{e^x - 1} + \frac{(c_p - c_i)xe^x}{(e^x - 1)^2}\right)\frac{\partial J_v}{\partial \alpha_{i_2}}.$$

$$\frac{\partial J_s}{\partial a_{i_2}}$$

can be derived in a similar manner when $J_v < 0$. Thus, we have $$\frac{\partial J_s}{\partial a_{i_2}} = \begin{cases} (1-\sigma)\left(c_i - \frac{c_p - c_i}{e^x - 1} + \frac{(c_p - c_i)xe^x}{(e^x - 1)^2}\right)\frac{\partial J_v}{\partial a_{i_2}} & \text{if } J_v > 0, \\ 0 & \text{if } J_v = 0, \\ (1-\sigma)\left(c_p - \frac{c_p - c_i}{e^x - 1} + \frac{(c_p - c_i)xe^x}{(e^x - 1)^2}\right)\frac{\partial J_v}{\partial a_{i_2}} & \text{if } J_v < 0. \end{cases} \quad (51)$$

The sensitivity equations with respect to $a_{i_2}$ can be obtained as follows $$\frac{d}{dt}\begin{pmatrix}\frac{\partial V_p}{\partial a_{i_2}}\\ \frac{\partial c_p}{\partial a_{i_2}}\\ \frac{\partial V_i}{\partial a_{i_2}}\\ \frac{\partial c_i}{\partial a_{i_2}}\end{pmatrix} = Jac_F\begin{pmatrix}\frac{\partial V_p}{\partial a_{i_2}}\\ \frac{\partial c_p}{\partial a_{i_2}}\\ \frac{\partial V_i}{\partial a_{i_2}}\\ \frac{\partial c_i}{\partial a_{i_2}}\end{pmatrix} + \begin{pmatrix}\frac{\partial F_1}{\partial a_{i_2}}\\ \frac{\partial F_2}{\partial a_{i_2}}\\ \frac{\partial F_3}{\partial a_{i_2}}\\ \frac{\partial F_4}{\partial a_{i_2}}\end{pmatrix} \text{ and so}$$

$$\frac{d}{dt}\left(\frac{\partial V_p}{\partial a_{i_2}}\right) = \frac{\partial}{\partial a_{i_2}}\left(\frac{dV_p}{dt}\right)$$
$$= \frac{\partial}{\partial V_p}(J_v + \kappa - J_{UF})\frac{\partial V_p}{\partial a_{i_2}} +$$
$$\frac{\partial}{\partial c_p}(J_v + \kappa - J_{UF})\frac{\partial c_p}{\partial a_{i_2}} +$$
$$\frac{\partial}{\partial V_i}(J_v + \kappa - J_{UF})\cdot \frac{\partial V_i}{\partial a_{i_2}} +$$
$$\frac{\partial}{\partial c_i}(J_v + \kappa - J_{UF})\frac{\partial c_i}{\partial a_{i_2}} + \frac{\partial}{\partial a_{i_2}}(J_v + \kappa - J_{UF})$$
$$= \frac{\partial J_v}{\partial c_p}\frac{\partial c_p}{\partial a_{i_2}} + \frac{\partial J_v}{\partial c_i}\frac{\partial c_i}{\partial a_{i_2}} + \frac{\partial J_v}{\partial a_{i_2}},$$

$$\frac{d}{dt}\left(\frac{\partial c_p}{\partial a_{i_2}}\right) = \frac{\partial}{\partial a_{i_2}}\left(\frac{dc_p}{dt}\right)$$
$$= \frac{\partial}{\partial V_p}\left(\frac{J_s - c_p(J_v + \kappa - J_{UF})}{V_p}\right)\frac{\partial V_p}{\partial a_{i_2}} +$$
$$\frac{\partial}{\partial c_p}\left(\frac{J_s - c_p(J_v + \kappa - J_{UF})}{V_p}\right)\frac{\partial c_p}{\partial a_{i_2}} +$$
$$\frac{\partial}{\partial V_i}\left(\frac{J_s - c_p(J_v + \kappa - J_{UF})}{V_p}\right)\frac{\partial V_i}{\partial a_{i_2}} +$$
$$\frac{\partial}{\partial c_i}\left(\frac{J_s - c_p(J_v + \kappa - J_{UF})}{V_p}\right)\frac{\partial c_i}{\partial a_{i_2}} +$$
$$\frac{\partial}{\partial a_{i_2}}\left(\frac{J_s - c_p(J_v + \kappa - J_{UF})}{V_p}\right)$$
$$= -\left(\frac{J_s - c_p(J_v + \kappa - J_{UF})}{V_p^2}\right)\frac{\partial V_p}{\partial a_{i_2}} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial a_{i_2}} +$$
$$\frac{1}{V_p}\left(\frac{\partial J_s}{\partial c_i} - c_p\frac{\partial J_v}{\partial c_i}\right)\frac{\partial c_i}{\partial a_{i_2}} + \frac{1}{V_p}\left(\frac{\partial J_s}{\partial a_{i_2}} - c_p\frac{\partial J_v}{\partial a_{i_2}}\right),$$

$$\frac{d}{dt}\left(\frac{\partial V_i}{\partial a_{i_2}}\right) = \frac{\partial}{\partial a_{i_2}}\left(\frac{dV_i}{dt}\right)$$
$$= \frac{\partial}{\partial V_p}(-J_v - \kappa)\frac{\partial V_p}{\partial a_{i_2}} +$$
$$\frac{\partial}{\partial c_p}(-J_v - \kappa)\frac{\partial c_p}{\partial a_{i_2}} +$$
$$\frac{\partial}{\partial V_i}(-J_v - \kappa)\frac{\partial V_i}{\partial a_{i_2}} +$$
$$\frac{\partial}{\partial c_i}(-J_v - \kappa)\frac{\partial c_i}{\partial a_{i_2}} + \frac{\partial}{\partial a_{i_2}}(-J_v - \kappa)$$
$$= -\frac{\partial J_v}{\partial c_p}\frac{\partial c_p}{\partial a_{i_2}} - \frac{\partial J_v}{\partial c_i}\frac{\partial c_i}{\partial a_{i_2}} + \frac{\partial J_v}{\partial a_{i_2}},$$

$$\frac{d}{dt}\left(\frac{\partial c_i}{\partial a_{i_2}}\right) = \frac{\partial}{\partial a_{i_2}}\left(\frac{dc_i}{dt}\right)$$
$$= +\frac{\partial}{\partial V_p}\left(\frac{-J_s + c_i(J_v + \kappa)}{V_i}\right)\frac{\partial V_p}{\partial a_{i_2}} +$$
$$\frac{\partial}{\partial c_p}\left(\frac{-J_s + c_i(J_v + \kappa)}{V_i}\right)\frac{\partial c_p}{\partial a_{i_2}} +$$
$$\frac{\partial}{\partial V_i}\left(\frac{-J_s + c_i(J_v + \kappa)}{V_i}\right)\frac{\partial V_i}{\partial a_{i_2}} +$$
$$\frac{\partial}{\partial c_i}\left(\frac{-J_s + c_i(J_v + \kappa)}{V_i}\right)\frac{\partial c_i}{\partial a_{i_2}} + +$$
$$\frac{\partial}{\partial a_{i_2}}\left(\frac{-J_s + c_i(J_v + \kappa)}{V_i}\right)$$
$$= \frac{1}{V_i}\left(-\frac{\partial J_s}{\partial c_p} + c_i\frac{\partial J_v}{\partial c_p}\right)\frac{\partial c_p}{\partial a_{i_2}} - \left(\frac{-J_s + c_i(J_v + \kappa)}{V_i^2}\right)\frac{\partial V_i}{\partial a_{i_2}} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial a_{i_2}} + \frac{1}{V_i}\left(-\frac{\partial J_s}{\partial a_{i_2}} + c_i\frac{\partial J_v}{\partial a_{i_2}}\right).$$

Sensitivity with Respect to κ

Note that $$\frac{\partial J_v}{\partial \kappa} = 0. \tag{52}$$

With $$x = \frac{J_v(1 - \sigma)}{PS},$$

it follows that $$\frac{\partial}{\partial \kappa}(e^x - 1) = 0, \tag{53}$$

$$\frac{\partial J_s}{\partial \kappa} = \alpha. \tag{54}$$

The sensitivity equations with respect to κ can be obtained as follows $$\frac{d}{dt}\begin{pmatrix}\frac{\partial V_p}{\partial \kappa}\\ \frac{\partial c_p}{\partial \kappa}\\ \frac{\partial V_i}{\partial \kappa}\\ \frac{\partial c_i}{\partial \kappa}\end{pmatrix} = Jac_F \begin{pmatrix}\frac{\partial V_p}{\partial \kappa}\\ \frac{\partial c_p}{\partial \kappa}\\ \frac{\partial V_i}{\partial \kappa}\\ \frac{\partial c_i}{\partial \kappa}\end{pmatrix} + \begin{pmatrix}\frac{\partial F_1}{\partial \kappa}\\ \frac{\partial F_2}{\partial \kappa}\\ \frac{\partial F_3}{\partial \kappa}\\ \frac{\partial F_4}{\partial \kappa}\end{pmatrix}$$

and so

-continued $$\frac{d}{dt}\left(\frac{\partial V_p}{\partial \kappa}\right) = \frac{\partial}{\partial \kappa}\left(\frac{dV_p}{dt}\right)$$
$$= \frac{\partial}{\partial V_p}(J_v + \kappa - J_{UF})\frac{\partial V_p}{\partial \kappa} + \frac{\partial}{\partial c_p}(J_v + \kappa - J_{UF})\frac{\partial c_p}{\partial \kappa} +$$
$$\frac{\partial}{\partial V_i}(J_v + \kappa - J_{UF})\frac{\partial V_i}{\partial \kappa} +$$
$$\frac{\partial}{\partial c_i}(J_v + \kappa - J_{UF})\frac{\partial c_i}{\partial \kappa} + \frac{\partial}{\partial \kappa}(J_v + \kappa - J_{UF})$$
$$= \frac{\partial J_v}{\partial c_p}\frac{\partial c_p}{\partial \kappa} + \frac{\partial J_v}{\partial c_i}\frac{\partial c_i}{\partial \kappa} + \frac{\partial J_v}{\partial \kappa} + 1$$
$$= \frac{\partial J_v}{\partial c_p}\frac{\partial c_p}{\partial \kappa} + \frac{\partial J_v}{\partial c_i}\frac{\partial c_i}{\partial \kappa} + 1,$$

$$\frac{d}{dt}\left(\frac{\partial c_p}{\partial \kappa}\right) = \frac{\partial}{\partial \kappa}\left(\frac{dc_p}{dt}\right)$$
$$= \frac{\partial}{\partial V_p}\left(\frac{J_s - c_p(J_v + \kappa - J_{UF})}{V_p}\right)\frac{\partial V_p}{\partial \kappa} +$$
$$\frac{\partial}{\partial c_p}\left(\frac{J_s - c_p(J_v + \kappa - J_{UF})}{V_p}\right)\frac{\partial c_p}{\partial \kappa} +$$
$$\frac{\partial}{\partial V_i}\left(\frac{J_s - c_p(J_v + \kappa - J_{UF})}{V_p}\right)\frac{\partial V_i}{\partial \kappa} +$$
$$\frac{\partial}{\partial c_i}\left(\frac{J_s - c_p(J_v + \kappa - J_{UF})}{V_p}\right)\frac{\partial c_i}{\partial \kappa} +$$
$$\frac{\partial}{\partial \kappa}\left(\frac{J_s - c_p(J_v + \kappa - J_{UF})}{V_p}\right)$$
$$= -\left(\frac{J_s - c_p(J_v + \kappa - J_{UF})}{V_p^2}\right)\frac{\partial V_p}{\partial \kappa} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial \kappa} +$$
$$\frac{1}{V_p}\left(\frac{\partial J_s}{\partial c_i} - c_p\frac{\partial J_v}{\partial c_i}\right)\frac{\partial c_i}{\partial \kappa} + \frac{1}{V_p}\left(\frac{\partial J_s}{\partial \kappa} - c_p\frac{\partial J_v}{\partial \kappa} - c_p\right)$$
$$= -\left(\frac{J_s - c_p(J_v + \kappa - J_{UF})}{V_p^2}\right)\frac{\partial V_p}{\partial \kappa} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial \kappa} +$$
$$\frac{1}{V_p}\left(\frac{\partial J_s}{\partial c_i} - c_p\frac{\partial J_v}{\partial c_i}\right)\frac{\partial c_i}{\partial \kappa} + \frac{\alpha - c_p}{V_p},$$

$$\frac{d}{dt}\left(\frac{\partial V_i}{\partial \kappa}\right) = \frac{\partial}{\partial \kappa}\left(\frac{dV_i}{dt}\right)$$
$$= +\frac{\partial}{\partial V_p}(-J_v - \kappa)\frac{\partial V_p}{\partial \kappa} + \frac{\partial}{\partial c_p}(-J_v - \kappa)\frac{\partial c_p}{\partial \kappa} +$$
$$\frac{\partial}{\partial V_i}(-J_v - \kappa)\frac{\partial V_i}{\partial \kappa} + \frac{\partial}{\partial c_i}(-J_v - \kappa)\frac{\partial c_i}{\partial \kappa} + \frac{\partial}{\partial \kappa}(-J_v - \kappa)$$
$$= -\frac{\partial J_v}{\partial c_p}\frac{\partial c_p}{\partial \kappa} - \frac{\partial J_v}{\partial c_i}\frac{\partial c_i}{\partial \kappa} - 1,$$

-continued $$\frac{d}{dt}\left(\frac{\partial c_i}{\partial \kappa}\right) = \frac{\partial}{\partial \kappa}\left(\frac{dc_i}{dt}\right)$$
$$= \frac{\partial}{\partial V_p}\left(\frac{-J_s + c_i(J_v + \kappa)}{V_i}\right)\frac{\partial V_p}{\partial \kappa} +$$
$$\frac{\partial}{\partial c_p}\left(\frac{-J_s + c_i(J_v + \kappa)}{V_i}\right)\frac{\partial c_p}{\partial \kappa} +$$
$$\frac{\partial}{\partial V_i}\left(\frac{-J_s + c_i(J_v + \kappa)}{V_i}\right)\frac{\partial V_i}{\partial \kappa} +$$
$$\frac{\partial}{\partial c_i}\left(\frac{-J_s + c_i(J_v + \kappa)}{V_i}\right)\frac{\partial c_i}{\partial \kappa} + \frac{\partial}{\partial \kappa}\left(\frac{-J_s + c_i(J_v + \kappa)}{V_i}\right)$$
$$= \frac{1}{V_i}\left(-\frac{\partial J_s}{\partial c_p} + c_i\frac{\partial J_v}{\partial c_p}\right)\frac{\partial c_p}{\partial \kappa} - \left(\frac{-J_s + c_i(J_v + \kappa)}{V_i^2}\right)\frac{\partial V_i}{\partial \kappa} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial \kappa} + \frac{1}{V_i}\left(-\frac{\partial J_s}{\partial \kappa} + c_i\frac{\partial J_v}{\partial \kappa} + c_i\right)$$
$$= \frac{1}{V_i}\left(-\frac{\partial J_s}{\partial c_p} + c_i\frac{\partial J_v}{\partial c_p}\right)\frac{\partial c_p}{\partial \kappa} - \left(\frac{-J_s + c_i(J_v + \kappa)}{V_i^2}\right)\frac{\partial V_i}{\partial \kappa} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial \kappa} + \frac{-\alpha + c_i}{V_i}.$$

Sensitivity with Respect to $\alpha$

Note that $$\frac{\partial J_v}{\partial \alpha} = 0. \qquad (55)$$

With $$x = \frac{J_v(1-\sigma)}{PS},$$

it follows that $$\frac{\partial}{\partial \alpha}(e^x - 1) = 0, \qquad (56)$$

$$\frac{\partial J_s}{\partial \alpha} = \kappa. \qquad (57)$$

The sensitivity equations with respect to $\alpha$ can be obtained as follows $$\frac{d}{dt}\begin{pmatrix}\frac{\partial V_p}{\partial \alpha}\\ \frac{\partial c_p}{\partial \alpha}\\ \frac{\partial V_i}{\partial \alpha}\\ \frac{\partial c_i}{\partial \alpha}\end{pmatrix} = Jac_F \begin{pmatrix}\frac{\partial V_p}{\partial \alpha}\\ \frac{\partial c_p}{\partial \alpha}\\ \frac{\partial V_i}{\partial \alpha}\\ \frac{\partial c_i}{\partial \alpha}\end{pmatrix} + \begin{pmatrix}\frac{\partial F_1}{\partial \alpha}\\ \frac{\partial F_2}{\partial \alpha}\\ \frac{\partial F_3}{\partial \alpha}\\ \frac{\partial F_4}{\partial \alpha}\end{pmatrix}$$

and so

-continued $$\frac{d}{dt}\left(\frac{\partial V_p}{\partial \alpha}\right) = \frac{\partial}{\partial \alpha}\left(\frac{dV_p}{dt}\right)$$
$$= \frac{\partial}{\partial V_p}(J_v + \kappa - J_{UF})\frac{\partial V_p}{\partial \alpha} + \frac{\partial}{\partial c_p}(J_v + \kappa - J_{UF})\frac{\partial c_p}{\partial \alpha} +$$
$$\frac{\partial}{\partial V_i}(J_v + \kappa - J_{UF})\frac{\partial V_i}{\partial \alpha} +$$
$$\frac{\partial}{\partial c_i}(J_v + \kappa - J_{UF})\frac{\partial c_i}{\partial \alpha} + \frac{\partial}{\partial \alpha}(J_v + \kappa - J_{UF})$$
$$= \frac{\partial J_v}{\partial c_p}\frac{\partial c_p}{\partial \alpha} + \frac{\partial J_v}{\partial c_i}\frac{\partial c_i}{\partial \alpha} + \frac{\partial J_v}{\partial \alpha}$$
$$= \frac{\partial J_v}{\partial c_p}\frac{\partial c_p}{\partial \alpha} + \frac{\partial J_v}{\partial c_i}\frac{\partial c_i}{\partial \alpha},$$

$$\frac{d}{dt}\left(\frac{\partial c_p}{\partial \alpha}\right) = \frac{\partial}{\partial \alpha}\left(\frac{dc_p}{dt}\right)$$
$$= \frac{\partial}{\partial V_p}\left(\frac{J_s - c_p(J_v + \kappa - J_{UF})}{V_p}\right)\frac{\partial V_p}{\partial \alpha} +$$
$$\frac{\partial}{\partial c_p}\left(\frac{J_s - c_p(J_v + \kappa - J_{UF})}{V_p}\right)\frac{\partial c_p}{\partial \alpha} +$$
$$\frac{\partial}{\partial V_i}\left(\frac{J_s - c_p(J_v + \kappa - J_{UF})}{V_p}\right)\frac{\partial V_i}{\partial \alpha} +$$
$$\frac{\partial}{\partial c_i}\left(\frac{J_s - c_p(J_v + \kappa - J_{UF})}{V_p}\right)\frac{\partial c_i}{\partial \alpha} + \frac{\partial}{\partial \alpha}\left(\frac{J_s - c_p(J_v + \kappa - J_{UF})}{V_p}\right)$$
$$= -\left(\frac{J_s - c_p(J_v + \kappa - J_{UF})}{V_p^2}\right)\frac{\partial V_p}{\partial \alpha} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial \alpha} +$$
$$\frac{1}{V_p}\left(\frac{\partial J_s}{\partial c_i} - c_p\frac{\partial J_v}{\partial c_i}\right)\frac{\partial c_i}{\partial \alpha} + \frac{1}{V_p}\left(\frac{\partial J_s}{\partial \alpha} - c_p\frac{\partial J_v}{\partial \alpha}\right)$$
$$= -\left(\frac{J_s - c_p(J_v + \kappa - J_{UF})}{V_p^2}\right)\frac{\partial V_p}{\partial \alpha} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial \alpha} +$$
$$\frac{1}{V_p}\left(\frac{\partial J_s}{\partial c_i} - c_p\frac{\partial J_v}{\partial c_i}\right)\frac{\partial c_i}{\partial \alpha} + \frac{\kappa}{V_p},$$

$$\frac{d}{dt}\left(\frac{\partial V_i}{\partial \alpha}\right) = \frac{\partial}{\partial \alpha}\left(\frac{dV_i}{dt}\right)$$
$$= \frac{\partial}{\partial V_p}(-J_v - \kappa)\frac{\partial V_p}{\partial \alpha} + \frac{\partial}{\partial c_p}(-J_v - \kappa)\frac{\partial c_p}{\partial \alpha} +$$
$$\frac{\partial}{\partial V_i}(-J_v - \kappa)\frac{\partial V_i}{\partial \alpha} + \frac{\partial}{\partial c_i}(-J_v - \kappa)\frac{\partial c_i}{\partial \alpha} + \frac{\partial}{\partial \alpha}(-J_v - \kappa)$$
$$= -\frac{\partial J_v}{\partial c_p}\frac{\partial c_p}{\partial \alpha} - \frac{\partial J_v}{\partial c_i}\frac{\partial c_i}{\partial \alpha},$$

-continued $$\frac{d}{dt}\left(\frac{\partial c_i}{\partial \alpha}\right) = \frac{\partial}{\partial \alpha}\left(\frac{dc_i}{dt}\right)$$
$$= \frac{\partial}{\partial V_p}\left(\frac{-J_s + c_i(J_v + \kappa)}{V_i}\right)\frac{\partial V_p}{\partial \alpha} +$$
$$\frac{\partial}{\partial c_p}\left(\frac{-J_s + c_i(J_v + \kappa)}{V_i}\right)\frac{\partial c_p}{\partial \alpha} +$$
$$\frac{\partial}{\partial V_i}\left(\frac{-J_s + c_i(J_v + \kappa)}{V_i}\right)\frac{\partial V_i}{\partial \alpha} +$$
$$\frac{\partial}{\partial c_i}\left(\frac{-J_s + c_i(J_v + \kappa)}{V_i}\right)\frac{\partial c_i}{\partial \alpha} + \frac{\partial}{\partial \alpha}\left(\frac{-J_s + c_i(J_v + \kappa)}{V_i}\right)$$
$$= \frac{1}{V_i}\left(-\frac{\partial J_s}{\partial c_p} + c_i\frac{\partial J_v}{\partial c_p}\right)\frac{\partial c_p}{\partial \alpha} - \left(\frac{-J_s + c_i(J_v + \kappa)}{V_i^2}\right)\frac{\partial V_i}{\partial \alpha} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial \alpha} + \frac{1}{V_i}\left(-\frac{\partial J_s}{\partial \alpha} + c_i\frac{\partial J_v}{\partial \alpha}\right)$$
$$= \frac{1}{V_i}\left(-\frac{\partial J_s}{\partial c_p} + c_i\frac{\partial J_v}{\partial c_p}\right)\frac{\partial c_p}{\partial \alpha} - \left(\frac{-J_s + c_i(J_v + \kappa)}{V_i^2}\right)\frac{\partial V_i}{\partial \alpha} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial \alpha} - \frac{\kappa}{V_i}.$$

Sensitivity with Respect to $J_{UF}$

Note that $$\frac{\partial J_v}{\partial J_{UF}} = 0. \tag{58}$$

With $$x = \frac{J_v(1 - \sigma)}{PS},$$

it follows that $$\frac{\partial}{\partial J_{UF}}(e^x - 1) = 0, \tag{59}$$

$$\frac{\partial J_s}{\partial J_{UF}} = 0. \tag{60}$$

The sensitivity equations with respect to $J_{UF}$ can be obtained as follows $$\frac{d}{dt}\begin{pmatrix}\frac{\partial V_p}{\partial J_{UF}}\\\frac{\partial c_p}{\partial J_{UF}}\\\frac{\partial V_i}{\partial J_{UF}}\\\frac{\partial c_i}{\partial J_{UF}}\end{pmatrix} = Jac_F\begin{pmatrix}\frac{\partial V_p}{\partial J_{UF}}\\\frac{\partial c_p}{\partial J_{UF}}\\\frac{\partial V_i}{\partial J_{UF}}\\\frac{\partial c_i}{\partial J_{UF}}\end{pmatrix} + \begin{pmatrix}\frac{\partial F_1}{\partial J_{UF}}\\\frac{\partial F_2}{\partial J_{UF}}\\\frac{\partial F_3}{\partial J_{UF}}\\\frac{\partial F_4}{\partial J_{UF}}\end{pmatrix}$$

and so

-continued $$\frac{d}{dt}\left(\frac{\partial V_p}{\partial J_{UF}}\right) = \frac{\partial}{\partial J_{UF}}\left(\frac{dV_p}{dt}\right)$$
$$= \frac{\partial}{\partial V_p}(J_v + \kappa - J_{UF})\frac{\partial V_p}{\partial J_{UF}} + \frac{\partial}{\partial c_p}(J_v + \kappa - J_{UF})\frac{\partial c_p}{\partial J_{UF}} +$$
$$\frac{\partial}{\partial V_i}(J_v + \kappa - J_{UF})\frac{\partial V_i}{\partial J_{UF}} +$$
$$\frac{\partial}{\partial c_i}(J_v + \kappa - J_{UF})\frac{\partial c_i}{\partial J_{UF}} + \frac{\partial}{\partial J_{UF}}(J_v + \kappa - J_{UF})$$
$$= \frac{\partial J_v}{\partial c_p}\frac{\partial c_p}{\partial J_{UF}} + \frac{\partial J_v}{\partial c_i}\frac{\partial c_i}{\partial J_{UF}} - 1,$$

$$\frac{d}{dt}\left(\frac{\partial c_p}{\partial J_{UF}}\right) = \frac{\partial}{\partial J_{UF}}\left(\frac{dc_p}{dt}\right)$$
$$= \frac{\partial}{\partial V_p}\left(\frac{J_s - c_p(J_v + \kappa - J_{UF})}{V_p}\right)\frac{\partial V_p}{\partial J_{UF}} +$$
$$\frac{\partial}{\partial c_p}\left(\frac{J_s - c_p(J_v + \kappa - J_{UF})}{V_p}\right)\frac{\partial c_p}{\partial \alpha} +$$
$$\frac{\partial}{\partial V_i}\left(\frac{J_s - c_p(J_v + \kappa - J_{UF})}{V_p}\right)\frac{\partial V_i}{\partial J_{UF}} +$$
$$\frac{\partial}{\partial c_i}\left(\frac{J_s - c_p(J_v + \kappa - J_{UF})}{V_p}\right)\frac{\partial c_i}{\partial J_{UF}} +$$
$$\frac{\partial}{\partial J_{UF}}\left(\frac{J_s - c_p(J_v + \kappa - J_{UF})}{V_p}\right)$$
$$= -\left(\frac{J_s - c_p(J_v + \kappa - J_{UF})}{V_p^2}\right)\frac{\partial V_p}{\partial J_{UF}} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial J_{UF}} +$$
$$\frac{1}{V_p}\left(\frac{\partial J_s}{\partial c_i} - c_p\frac{\partial J_v}{\partial c_i}\right)\frac{\partial c_i}{\partial J_{UF}} + \frac{1}{V_p}\left(\frac{\partial J_s}{\partial J_{UF}} - c_p\frac{\partial J_v}{\partial J_{UF}} + c_p\right)$$
$$= -\left(\frac{J_s - c_p(J_v + \kappa - J_{UF})}{V_p^2}\right)\frac{\partial V_p}{\partial \alpha} +$$
$$\frac{1}{V_p}\left(\frac{\partial J_s}{\partial c_p} - c_p\frac{\partial J_v}{\partial c_p} - (J_v + \kappa - J_{UF})\right)\frac{\partial c_p}{\partial \alpha} +$$
$$\frac{1}{V_p}\left(\frac{\partial J_s}{\partial c_i} - c_p\frac{\partial J_v}{\partial c_i}\right)\frac{\partial c_i}{\partial \alpha} + \frac{c_p}{V_p},$$

$$\frac{d}{dt}\left(\frac{\partial V_i}{\partial J_{UF}}\right) = \frac{\partial}{\partial J_{UF}}\left(\frac{dV_i}{dt}\right)$$
$$= \frac{\partial}{\partial V_p}(-J_v - \kappa)\frac{\partial V_p}{\partial J_{UF}} + \frac{\partial}{\partial c_p}(-J_v - \kappa)\frac{\partial c_p}{\partial J_{UF}} +$$
$$\frac{\partial}{\partial V_i}(-J_v - \kappa)\frac{\partial V_i}{\partial J_{UF}} + \frac{\partial}{\partial c_i}(-J_v - \kappa)\frac{\partial c_i}{\partial J_{UF}} + \frac{\partial}{\partial J_{UF}}(-J_v - \kappa)$$
$$= -\frac{\partial J_v}{\partial c_p}\frac{\partial c_p}{\partial J_{UF}} - \frac{\partial J_v}{\partial c_i}\frac{\partial c_i}{\partial J_{UF}},$$

$$\frac{d}{dt}\left(\frac{\partial c_i}{\partial J_{UF}}\right) = \frac{\partial}{\partial J_{UF}}\left(\frac{dc_i}{dt}\right)$$
$$= \frac{\partial}{\partial V_p}\left(\frac{-J_s + c_i(J_v + \kappa)}{V_i}\right)\frac{\partial V_p}{\partial J_{UF}} +$$
$$\frac{\partial}{\partial c_p}\left(\frac{-J_s + c_i(J_v + \kappa)}{V_i}\right)\frac{\partial c_p}{\partial J_{UF}} +$$
$$\frac{\partial}{\partial V_i}\left(\frac{-J_s + c_i(J_v + \kappa)}{V_i}\right)\frac{\partial V_i}{\partial J_{UF}} +$$
$$\frac{\partial}{\partial c_i}\left(\frac{-J_s + c_i(J_v + \kappa)}{V_i}\right)\frac{\partial c_i}{\partial J_{UF}} + \frac{\partial}{\partial J_{UF}}\left(\frac{-J_s + c_i(J_v + \kappa)}{V_i}\right)$$
$$= \frac{1}{V_i}\left(-\frac{\partial J_s}{\partial c_p} + c_i\frac{\partial J_v}{\partial c_p}\right)\frac{\partial c_p}{\partial J_{UF}} - \left(\frac{-J_s + c_i(J_v + \kappa)}{V_i^2}\right)\frac{\partial V_i}{\partial J_{UF}} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial J_{UF}} + \frac{1}{V_i}\left(-\frac{\partial J_s}{\partial J_{UF}} + c_i\frac{\partial J_v}{\partial J_{UF}}\right)$$
$$= \frac{1}{V_i}\left(-\frac{\partial J_s}{\partial c_p} + c_i\frac{\partial J_v}{\partial c_p}\right)\frac{\partial c_p}{\partial J_{UF}} - \left(\frac{-J_s + c_i(J_v + \kappa)}{V_i^2}\right)\frac{\partial V_i}{\partial J_{UF}} +$$
$$\frac{1}{V_i}\left(-\frac{\partial J_s}{\partial c_i} + c_i\frac{\partial J_v}{\partial c_i} + (J_v + \kappa)\right)\frac{\partial c_i}{\partial J_{UF}}.$$

The invention claimed is:

1. A method, comprising:

receiving, by a processing system, measurements of a blood-related parameter corresponding to a patient undergoing hemodialysis treatment;

estimating, by the processing system, values of hemodialysis treatment-related parameters by applying a vascular refill model based on the received measurements of the blood-related parameter, wherein the hemodialysis treatment-related parameters are indicative of an effect of vascular refill on the patient caused by the hemodialysis treatment and include a filtration coefficient ($L_p$) and a hydrostatic capillary pressure ($P_c$);

determining, by the processing system, based on the estimated values of the hemodialysis treatment-related parameters, a hemodialysis treatment-related operation; and facilitating, by the processing system, performance of the hemodialysis treatment-related operation;

wherein the vascular refill model is a two-compartment model based on a first compartment corresponding to blood plasma in the patient's body, a second compartment based on interstitial fluid in the patient's body, and a semi-permeable membrane separating the first compartment and the second compartment;

wherein the dynamics of the two-compartment model are described by the following system of equations:

$$\begin{cases} \frac{dV_p}{dt} = J_v + \kappa - J_{UF} \\ \frac{dc_p}{dt} = \frac{J_s - c_p(J_v + \kappa - J_{UF})}{V_p}, \\ \frac{dV_i}{dt} = -J_v - \kappa, \\ \frac{dc_i}{dt} = \frac{-J_s + c_i(J_v + \kappa)}{V_i}, \end{cases}$$

-continued where $$J_v = L_p(\sigma((a_{p_1}c_p + a_{p_2}c_p^2) - (a_{i_1}c_i + a_{i_2}c_i^2)) - (P_c - P_i)),$$

$$J_s = \begin{cases} J_v(1-\sigma)\left(c_i - \dfrac{c_p - c_i}{e^x - 1}\right) + \alpha\kappa & \text{if } J_v > 0, \\ \alpha\kappa & \text{if } J_v = 0, \\ J_v(1-\sigma)\left(c_p - \dfrac{c_p - c_i}{e^x - 1}\right) + \alpha\kappa & \text{if } J_v < 0, \end{cases}$$

and $$x = \frac{J_v(1-\sigma)}{PS},$$

wherein $V_p$ corresponds to the first compartment, $J_v$ corresponds to the amount of fluid crossing the membrane at a certain time, $\kappa$ corresponds to a constant lymph flow from interstitum to plasma, $J_{UF}$ corresponds to ultrafiltration rate, $J_s$ corresponds to net protein flux, $c_p$ corresponds to a protein concentration in plasma, $c_i$ corresponds to a protein concentration in interstitum, $V_i$ corresponds to the second compartment, $\sigma$ corresponds to the osmotic reflection coefficient, $P_i$ corresponds to hydrostatic interstitial pressure, $\alpha$ corresponds to a constant protein concentration of the constant lymph flow, x corresponds to a Peclet number describing convective flux relative to diffusive capacity of the membrane, and PS corresponds to a permeability-surface area product.

2. The method according to claim 1, wherein the hemodialysis treatment-related operation comprises adjustment of a rate of ultrafiltration for the patient undergoing hemodialysis treatment.

3. The method according to claim 1, wherein the hemodialysis treatment-related operation comprises stoppage of the hemodialysis treatment for the patient.

4. The method according to claim 1, wherein the hemodialysis treatment-related operation comprises generating an alert.

5. The method according to claim 1, wherein the hemodialysis treatment-related operation comprises providing a notification indicating the estimated values of the hemodialysis treatment-related parameters.

6. The method according to claim 5, wherein the notification is displayed on a screen.

7. The method according to claim 1, wherein the measurements of the blood-related parameter are hematocrit measurements or relative blood volume measurements.

8. The method according to claim 1, wherein the hemodialysis treatment-related parameters further include one or more of the group consisting of:
hydrostatic interstitial pressure ($P_i$);
a systemic capillary reflection coefficient ($\sigma$);
constant protein concentration ($\alpha$); and
constant lymph flow rate ($\kappa$).

9. The method according to claim 1, wherein the vascular refill model defines short-term dynamics of vascular refill with respect to a time period of about an hour.

10. The method according to claim 1, further comprising:
receiving, by the processing system, an ultrafiltration rate set by a dialysis machine providing the hemodialysis treatment to the patient;
wherein estimating the values of the hemodialysis treatment-related parameters by applying the vascular refill model is further based on the received ultrafiltration rate.

11. The method according to claim 1, wherein estimating the values of the hemodialysis treatment-related parameters by applying the vascular refill model is further based on previously estimated values of the hemodialysis treatment-related parameters corresponding to the patient obtained from a database.

12. The method according to claim 1, wherein estimating the values of the hemodialysis treatment-related parameters by applying the vascular refill model is further based on initial default values for the hemodialysis treatment-related parameters.

13. The method according to claim 1, wherein applying the vascular refill model includes iteratively solving an inverse problem to compute the estimated values of the hemodialysis treatment-related parameters.

14. The method according to claim 1, further comprising:
determining a quality level of the received measurements; and
selecting one or more types of hemodialysis treatment-related parameters to estimate based on the determined quality level.

15. A non-transitory processor-readable medium having processor-executable instructions stored thereon, the processor-executable instructions, when executed by a processor, being configured to facilitate performance of the following steps:
receiving, by a processing system, measurements of a blood-related parameter corresponding to a patient undergoing hemodialysis treatment;
estimating, by the processing system, values of hemodialysis treatment-related parameters by applying a vascular refill model based on the received measurements of the blood-related parameter, wherein the hemodialysis treatment-related parameters are indicative of an effect of vascular refill on the patient caused by the hemodialysis treatment and include a filtration coefficient ($L_p$) and a hydrostatic capillary pressure ($P_c$);
determining, by the processing system, based on the estimated values of the hemodialysis treatment-related parameters, a hemodialysis treatment-related operation; and
facilitating, by the processing system, performance of the hemodialysis treatment-related operation;
wherein the vascular refill model is a two-compartment model based on a first compartment corresponding to blood plasma in the patient's body, a second compartment based on interstitial fluid in the patient's body, and a semi-permeable membrane separating the first compartment and the second compartment;
wherein the dynamics of the two-compartment model are described by the following system of equations:

$$\begin{cases} \dfrac{dV_p}{dt} = J_v + \kappa - J_{UF} \\ \dfrac{dc_p}{dt} = \dfrac{J_s - c_p(J_v + \kappa - J_{UF})}{V_p}, \\ \dfrac{dV_i}{dt} = -J_v - \kappa, \\ \dfrac{dc_i}{dt} = \dfrac{-J_s + c_i(J_v + \kappa)}{V_i}, \end{cases}$$

-continued where $$J_v = L_p(\sigma((a_{p_1} c_p + a_{p_2} c_p^2) - (a_{i_1} c_i + a_{i_2} c_i^2)) - (P_c - P_i)),$$

$$J_s = \begin{cases} J_v(1-\sigma)\left(c_i - \dfrac{c_p - c_i}{e^x - 1}\right) + \alpha\kappa & \text{if } J_v > 0, \\ \alpha\kappa & \text{if } J_v = 0, \\ J_v(1-\sigma)\left(c_p - \dfrac{c_p - c_i}{e^x - 1}\right) + \alpha\kappa & \text{if } J_v < 0, \end{cases}$$

and $$x = \frac{J_v(1-\sigma)}{PS},$$

wherein $V_p$ corresponds to the first compartment, $J_v$ corresponds to the amount of fluid crossing the membrane at a certain time, $\kappa$ corresponds to a constant lymph flow from interstitum to plasma, $J_{UF}$ corresponds to ultrafiltration rate, $J_s$ corresponds to net protein flux, $c_p$ corresponds to a protein concentration in plasma, $c_i$ corresponds to a protein concentration in interstitum, $V_i$ corresponds to the second compartment, $\sigma$ corresponds to the osmotic reflection coefficient, $P_i$ corresponds to hydrostatic interstitial pressure, $\alpha$ corresponds to a constant protein concentration of the constant lymph flow, x corresponds to a Peclet number describing convective flux relative to diffusive capacity of the membrane, and PS corresponds to a permeability-surface area product.

16. The non-transitory processor-readable medium according to claim 15, wherein the hemodialysis treatment-related parameters further include one or more of the group consisting of:
  hydrostatic interstitial pressure ($P_i$);
  a systemic capillary reflection coefficient ($\sigma$);
  constant protein concentration ($\alpha$); and
  constant lymph flow rate ($\kappa$).

17. A system, comprising:
  a monitoring device configured to obtain measurements of a blood-related parameter corresponding to a patient undergoing hemodialysis treatment; and
  a processing system configured to:
    receive the measurements of the blood-related parameter corresponding to the patient undergoing hemodialysis treatment from the monitoring device;
    estimate values of hemodialysis treatment-related parameters by applying a vascular refill model based on the received measurements of the blood-related parameter, wherein the hemodialysis treatment-related parameters are indicative of an effect of vascular refill on the patient caused by the hemodialysis treatment and include a filtration coefficient ($L_p$) and a hydrostatic capillary pressure ($P_c$);
    determine, based on the estimated values of the hemodialysis treatment-related parameters, a hemodialysis treatment-related operation; and
    facilitate performance of the hemodialysis treatment-related operation;
    wherein the vascular refill model is a two-compartment model based on a first compartment corresponding to blood plasma in the patient's body, a second compartment based on interstitial fluid in the patient's body, and a semi-permeable membrane separating the first compartment and the second compartment;
    wherein the dynamics of the two-compartment model are described by the following system of equations:

$$\begin{cases} \dfrac{dV_p}{dt} = J_v + \kappa - J_{UF} \\ \dfrac{dc_p}{dt} = \dfrac{J_s - c_p(J_v + \kappa - J_{UF})}{V_p}, \\ \dfrac{dV_i}{dt} = -J_v - \kappa, \\ \dfrac{dc_i}{dt} = \dfrac{-J_s + c_i(J_v + \kappa)}{V_i}, \end{cases}$$

where $$J_v = L_p(\sigma((a_{p_1} c_p + a_{p_2} c_p^2) - (a_{i_1} c_i + a_{i_2} c_i^2)) - (P_c - P_i)),$$

$$J_s = \begin{cases} J_v(1-\sigma)\left(c_i - \dfrac{c_p - c_i}{e^x - 1}\right) + \alpha\kappa & \text{if } J_v > 0, \\ \alpha\kappa & \text{if } J_v = 0, \\ J_v(1-\sigma)\left(c_p - \dfrac{c_p - c_i}{e^x - 1}\right) + \alpha\kappa & \text{if } J_v < 0, \end{cases}$$

and $$x = \frac{J_v(1-\sigma)}{PS},$$

wherein $V_p$ corresponds to the first compartment, $J_v$ corresponds to the amount of fluid crossing the membrane at a certain time, K corresponds to a constant lymph flow from interstitum to plasma, $J_{UF}$ corresponds to ultrafiltration rate, $J_s$ corresponds to net protein flux, $c_p$ corresponds to a protein concentration in plasma, $c_i$ corresponds to a protein concentration in interstitum, $V_i$ corresponds to the second compartment, $\sigma$ corresponds to the osmotic reflection coefficient, $P_i$ corresponds to hydrostatic interstitial pressure, $\alpha$ corresponds to a constant protein concentration of the constant lymph flow, x corresponds to a Peclet number describing convective flux relative to diffusive capacity of the membrane, and PS corresponds to a permeability-surface area product.

18. The system according to claim 17, further comprising:
  a data storage configured to communicate with the processing system and to receive and store the estimated values of the hemodialysis treatment-related parameters.

19. The system according to claim 17, wherein the hemodialysis treatment-related parameters further include one or more of the group consisting of:
  hydrostatic interstitial pressure ($P_i$);
  a systemic capillary reflection coefficient ($\sigma$);
  constant protein concentration ($\alpha$); and
  constant lymph flow rate ($\kappa$).

* * * * *

UNITED STATES PATENT AND TRADEMARK OFFICE
CERTIFICATE OF CORRECTION

Page 1 of 2

PATENT NO. : 10,569,000 B2
APPLICATION NO. : 15/309727
DATED : February 25, 2020
INVENTOR(S) : Aurelio A. De los Reyes, V et al.

It is certified that error appears in the above-identified patent and that said Letters Patent is hereby corrected as shown below:

In the Claims

Claim 1, Column 51, Line 19, the text:
"from interstitum"
Should read:
--from interstitium--

Claim 1, Column 51, Line 23, the text:
"interstitum,"
Should read:
--interstitium,--

Claim 15, Column 53, Line 19, the text:
"from interstitum"
Should read:
--from interstitium--

Claim 15, Column 53, Line 23, the text:
"interstitum,"
Should read:
--interstitium,--

Claim 17, Column 54, Line 35, the text:
"from interstitum"
Should read:
--from interstitium--

Signed and Sealed this
Fourteenth Day of April, 2020

Andrei Iancu
*Director of the United States Patent and Trademark Office*

CERTIFICATE OF CORRECTION (continued)
U.S. Pat. No. 10,569,000 B2

Claim 17, Column 54, Line 39, the text:
"interstitum,"
Should read:
--interstitium,--